US012053475B2

(12) United States Patent
Beech et al.

(10) Patent No.: US 12,053,475 B2
(45) Date of Patent: Aug. 6, 2024

(54) TRPC ION CHANNEL INHIBITORS FOR USE IN THERAPY

(71) Applicant: UNIVERSITY OF LEEDS, Leeds (GB)

(72) Inventors: David John Beech, Leeds (GB); Richard James Foster, Leeds (GB); Sin Ying Cheung, Stanford, CA (US); Baptiste Michel Rode, Bordeaux (FR)

(73) Assignee: University of Leeds, Leeds (GB)

( * ) Notice: Subject to any disclaimer, the term of this patent is extended or adjusted under 35 U.S.C. 154(b) by 199 days.

(21) Appl. No.: 17/451,148

(22) Filed: Oct. 15, 2021

(65) Prior Publication Data

US 2022/0031706 A1 Feb. 3, 2022

Related U.S. Application Data

(63) Continuation of application No. 16/483,217, filed as application No. PCT/GB2018/050369 on Feb. 9, 2018, now abandoned.

(30) Foreign Application Priority Data

Feb. 9, 2017 (GB) ..................... 1702160

(51) Int. Cl.
*A61K 31/522* (2006.01)
*A61K 31/4184* (2006.01)
*A61K 31/713* (2006.01)
*A61P 3/04* (2006.01)
*A61P 3/10* (2006.01)

(52) U.S. Cl.
CPC ........ *A61K 31/522* (2013.01); *A61K 31/4184* (2013.01); *A61K 31/713* (2013.01); *A61P 3/04* (2018.01); *A61P 3/10* (2018.01)

(58) Field of Classification Search
CPC .............. A61K 31/522; A61K 31/4184; A61K 31/713; A61P 3/04; A61P 3/10
See application file for complete search history.

(56) References Cited

U.S. PATENT DOCUMENTS

| 2,689,853 A | 9/1954 | Schenck et al. |
| 2006/0034763 A1 | 2/2006 | Chen et al. |
| 2014/0275071 A1 | 9/2014 | Chenard et al. |
| 2014/0275528 A1 | 9/2014 | Chenard et al. |

FOREIGN PATENT DOCUMENTS

| GB | 703273 A | 2/1954 |
| JP | 2013-095693 A | 5/2013 |
| WO | WO 03/057843 A2 | 7/2003 |
| WO | WO 2010/107739 A2 | 9/2010 |
| WO | WO 2011/022638 A1 | 2/2011 |
| WO | WO 2014/143799 A2 | 9/2014 |
| WO | WO 2015/171598 A1 | 11/2015 |
| WO | WO 2016/086008 A1 | 6/2016 |
| WO | WO 2016/130385 A2 | 8/2016 |
| WO | WO 2017/004454 A1 | 1/2017 |

OTHER PUBLICATIONS

Liu et al (The Role of Transient Receptor Potential Channels in Metabolic Syndrome) Hypertens Res vol. 31, No. 11 (2008) 7 pages.
Hu et al. (Canonical Transient Receptor Potential Channels Expression is Elevated in a Porcine Model of Metabolic Syndrome) Mol Endocrinol, May (2009), 23(5):689-699, 11 pages.
Logothetis et al. (Channelopathies linked to plasma membrane phosphoinositides) Pflugers Arch—Eur J Physiol (2010) 460:321-341, 21 pages.
Zhu et al. (TRP channels and their implications in metabolic diseases) Pflugers Arch—Eur J Physiol (2011) 461:211-223, 13 pages.
Minard et al. (Remarkable Progress with Small-Molecule Modulation of TRPC1/4/5 Channels: Implications for Understanding the Channels in Health and Disease) Cells (2018) 7, 52:doi:10.3390/cells7060052, 20 pages.
European Application No. 18705479 Search Results Under Rule 164(2)(b) EPC; Jun. 16, 2022, 6 pages.
Interantional Search Report and Written Opinion of PCT/GB2018/050369 mailed Jul. 11, 2018, 28 pages.
Search Report under Section 17 of Application No. GB1702160.1 dated Nov. 24, 2017; 6 pages.
Beck et al., "Conserved Gating Elements in TRPC4 and TRPC5 Channels", The Journal of Biological Chemistry, Jul. 5, 2013, vol. 288, No. 27, pp. 19471-19483.
Beech et al., "Characteristics of Transient Receptor Potential Canonical Calcium-Permeable Channels and Their Relevance to Vascular Physiology and Disease", Official Journal of the Japanese Circulation Society, Circulation Journal, vol. 77, Mar. 2013, pp. 571-579.
Bon et al., "In pursuit of small molecule chemistry for calcium-permeable non-selective TRPC channels—mirage or pot of gold?", British Journal of Pharmacology, 2013, vol. 170, pp. 459-474.
Chen et al., "Resveratrol improves insulin resistance, glucose and lipid metabolism in patients with non-alcoholic fatty liver disease: A randomized controlled trial", Digestive and Liver Disease, W.B., Saunders, GB, vol. 47, No. 3, Dec. 16, 2014, pp. 226-232.
Gao et al., "TrpC5 Mediates Acute Leptin and Serotonin Effects via Pomc Neurons", Cell Reports 18, Jan. 17, 2017, pp. 583-592.
Hu et al., "Canonical Transient Receptor Potential Channels Expression is Elevated in a Porcine Model of Metabolic Syndrome", Molecular Endocrinology, (2009), 23, pp. 689-699.

(Continued)

*Primary Examiner* — Bruck Kifle
(74) *Attorney, Agent, or Firm* — Shackelford, McKinley & Norton, LLP

(57) ABSTRACT

Described herein are inhibitors Transient Receptor Potential Canonical (TRPC) ion channels comprising TRPC4 protein and/or TRPC5 protein for use in combating obesity and other medical conditions including insulin resistance associated with Type II diabetes or development of Type II diabetes (pre-diabetes), metabolic syndrome, non-alcoholic fatty liver disease (NAFLD) and non-alcoholic steatohepatitis (NASH). Also disclosed is the use of the inhibitors for cosmetic purposes, such as cosmetic weight loss.

12 Claims, 18 Drawing Sheets

(56) References Cited

OTHER PUBLICATIONS

Just et al., "Treatment with HC-070, a potent inhibitor of TRPC4 and TRPC5, leads to anxiolytic and antidepressant effects in mice", PLoS ONE 13(1): e0191225; https://doi.org/10.1371/journal.pone.0191225.
Kubota et al., "Adiponectin Stimulates AMP-Activated Protein Kinase in the Hypothalamus and Increases Food Intake", Cell Metabolism, Jul. 2007, vol. 6, pp. 55-68.
Kumar et al., "Anti-obesity effects of galangin, a pancreatic lipase inhibitor in cafeteria diet fed female rats", Pharmaceutical Biology, Swets and Eitlinger, Lisse, NL, Jun. 1, 2013, pp. 607-613.
Miller et al., "Identification of ML204, a Novel Potent Antagonist That Selectively Modulates Native TRPC4/C5 Ion Channels", The Journal of Biological Chemistry, Sep. 23, 2011, vol. 286, No. 38, pp. 33436-33446, doi: 10.1074/jbc.M111.274167 and supplementary materails at http://www.jbc.org/contentisuppl/2011 /07/26/M111.274167.DC1.html; 12 pages.
Naylor et al., "TRPC5 Channel Sensitivities to Antioxidants and Hydroxylated Stilbenes", Journal of Biological Chemistry, vol. 286, No. 7, Feb. 18, 2011, pp. 5078-5086.
Naylor et al., "Natural and synthetic flavonoid modulation of TRPC5 channels: Natural and synthetic flavonoid modulation of TRPC5 channels", British Journal of Pharmacology, vol. 173, No. 3, Jan. 13, 2016, pp. 562-574.
Rode et al., "Impact of TRPC channels on body weight", The Faseb Journal, Federation of American Societies for Experimental Biology, US, vol. 28, No. 1, Suppl. S, Mar. 31, 2014, p. 1057.9.
Sivakumar et al., "Dose-dependent effect of galangin on fructose-mediated insulin resistance and oxidative events in rat kidney", Redox Report, vol. 15, No. 5, Oct. 1, 2010, pp. 224-232.
Sukumar et al., "Constitutively-active TRPC channels of adipocytes confer a mechanism for sensing dietary fatty acids and regulating adiponectin", Circ Research, Jul. 6, 2012; 111(2), pp. 191-200. doi:10.1161/CIRCRESAHA.112.270751 and Supplemental materials, 18 pages.
Westlund et al., "A Rat Knockout Model Implicates Trpc4 Invisceral Pain Sensation", Neuroscience, 2014, vol. 262, pp. 165-175.
Xu et al., "Generation of functional ion-channel tools by E3 targeting", Advance Online Publication, Nature Biotechnology, Received Jul. 18; accepted Aug. 17; published online Sep. 18, 2005; doi:10.1038/nbt1148.
Zhou et al., "A small-molecule inhibitor of TRPC5 ion channels suppresses progressive kidney disease in animal models", Science, Dec. 8, 2017, vol. 358, pp. 1332-1336.
Examination Report for European patent application No. 18705479.6, mailed on Jan. 24, 2024.
Bishnoi M et al: "Expression of multiple Transient Receptor Potential channel genes in murine 3T3-L 1 cell lines and adipose tissue", Pharmacological Reports, vol. 65, May 1, 2013 (May 1, 2013), pp. 751-755, XP55930631, ISSN: 1734-1140.
M. Miller et al: "Identification of ML204, a Novel Potent Antagonist That Selectively Modulates Native TRPC4/C5 Ion Channels", Journal of Biological Chemistry, vol. 286, No. 38, Sep. 23, 2011 (Sep. 23, 2011), pp. 33436-33446, XP55053586, ISSN: 0021-9258, DOI: 10.1074/jbc.M111.274167.
Hussein N Rubaiy: "Treasure troves of pharmacological tools to study transient receptor potential canonical 1/4/5 channels", British Journal of Pharmacology, vol. 176, No. 7, Mar. 6, 2019 (Mar. 6, 2019), pp. 832-846, XP071172128, ISSN: 0007-1188, DOI: 10.1111/BPH.14578.
J. M. Richter et al: "Clemizole Hydrochloride is a Novel and Potent Inhibitor of Transient Receptor Potential Channel TRPC5", Molecular Pharmacology, vol. 86, No. 5, Aug. 19, 2014 (Aug. 19, 2014), pp. 514-521, XP55519879, DOI: 10.1124/mol.114.093229.

TRPC ION CHANNEL INHIBITORS FOR USE IN THERAPY

CROSS-REFERENCE TO RELATED APPLICATIONS

This application is a continuation of U.S. patent application Ser. No. 16/483,217, filed Aug. 2, 2019, which is a national-stage filing under 37 USC 371(c) of International Application No. PCT/GB2018/050369, filed Feb. 9, 2018, which claims priority to, and the benefit of, United Kingdom Patent Application No. GB1702160.1, filed Feb. 9, 2017, the entire contents of each of which are herein incorporated by reference in their entirety for all purposes.

FIELD OF THE INVENTION

The invention relates to direct inhibitors of Transient Receptor Potential Canonical (TRPC) ion channels comprising TRPC4 protein and/or TRPC5 protein as present in adipocytes for use especially in combating obesity (reducing obesity or inhibiting on-set of obesity); this may be for therapeutic purpose or cosmetic weight loss. More particularly, such an inhibitor may target expression or function of TRPC4 and/or TRPC 5 so as to affect ion channel activity or formation. It is envisaged that such use may also extend to the treatment or prophylaxis of insulin resistance associated with Type II diabetes or development of Type II diabetes (pre-diabetes), metabolic syndrome, non-alcoholic fatty liver disease (NAFLD) and non-alcoholic steatohepatitis (NASH).

BACKGROUND OF THE INVENTION

Obesity is now a deadly global pandemic. Worldwide obesity has more than doubled since 1980. In 2014, 39% of adults over 18 were considered overweight and 13% (over 600 million adults) were obese according to the World Health Organisation. Even a modest degree of obesity, particularly if the excess fat is located in the abdomen, increases the risks for Type II diabetes, cardiovascular diseases, stroke and some forms of cancer. The economic cost of obesity is estimated to be $2 trillion annually or roughly 2.8 percent of global GDP according to the McKinsey Global Institute. Methods for managing body weight by dietary restriction and/or by exercise are largely ineffective as few people stick to dietary regimens for a long time, and compliance to regular exercise is equally poor. The result is generally a transient phase of weight loss (or weight stability) followed by a return on the trajectory towards obesity. These failures have highlighted the need for safe anti-obesity therapies.

In humans and many other mammals, fat is stored in adipose tissues. Adipose tissues are classified into two types-white adipose tissue (i.e., "white fat") and brown adipose tissue (i.e., "brown fat"). After food consumption, excess calories are stored as fat in adipocytes of white fat. By contrast, brown fat stores little fat, instead burning it to produce heat and regulate body temperature.

White fat adipocytes have previously been shown to present ion channels formed by Transient Receptor Potential Canonical (TRPC) proteins which have been linked to modulation of adiponectin, an adipokine signalling molecule which has been implicated in increasing insulin sensitivity, decreasing inflammation and protecting against atherosclerosis and myocardial decline. Decreased concentrations of adiponection occur in obesity-induced insulin resistance and are associated with endothelial dysfunction, Type II diabetes and hypertension. As further expanded upon below, more recently TRPC1 and TRPC 5 have been shown to be up-regulated in murine adipocytes as they mature leading to constitutively-active $Ca^{2+-}$-permeable channels. Moreover, constitutive $Ca^{2+}$ influx through TRPC5-comprising channels has been linked to suppression of adiponectin generation (Sukumar et al. (2012) Circ. Res. 111, 191-200).

TRPC channels are a subfamily of the $Ca^{2+}$ permeable channels formed by Transient Receptor Potential (TRP) proteins. TRP proteins are classified into sub-families based on amino acid sequence. The canonical (C) sub-family is one such family which contains six members in humans (TRPC1, 3-7); the additional TRPC 2 protein found in other mammals is not expressed in humans due correspondence with a pseudo-gene. TRPC1, TRPC4 and TRPC5 are considered to form a sub-group and TRPC3, TRPC6 and TRPC7 another sub-group. At the proximal C-terminus of proteins of the TRPC sub-family is a TRP box motif containing the invariant EWKFAR sequence and near the N-terminus between 3 and 4 ankyrin repeats. Each TRP protein is considered to have 6 membrane-spanning segments and intracellular N- and C-termini. To form trans-membrane ion channels, TRP proteins assemble together around a central ion-selectivity filter and gate, most likely as a group of 4 TRP proteins. All known TRPC channels are non-selective cationic channels that can enable entry into cells of both $Ca^{2+}$ and $Na^+$ The specific TRP proteins that form an individual channel may be identical (homomers) or different (heteromers). TRPCs are recognised to be promiscuous in forming heteromers and there is even evidence that this extends outside the TRPC subfamily to TRPV4 and TRPP2. Much remains to be determined about the compositions of native TRPC-containing channels and the functional significance of TRPC heteromerization. TRPC1 has been suggested to be an oddity amongst TRPC proteins in that it forms ion channels poorly or not at all when expressed alone in vitro in heterologous systems. In contrast other TRPCs form plasma membrane channels quite readily when expressed alone (i.e. they form functional homomers). TRPC1 is thought probably only to be a component of heteromeric ion channels with other TRPCs. Although some studies have shown signals when TRPC1 is expressed alone, the signals have generally been small and could be explained by TRPC1 forming heteromers with endogeneous TRPs of the expression system. [Beech (2013) Circ. J. 77, 570-579: Characteristics of Transient Receptor Potential Canonical Calcium Permeable Channels and Their relevance to Vascular Physiology and Disease; Bon and Beech (2013) Brit. J. Pharmacol. 170, 459-474, Review: In pursuit of small molecule chemistry for calcium-permeable non-selective TRPC channels-mirage or pot of gold?]. Thus up to now it has been recognised that mature adipocytes may have functional TRPC5-containing ion channels which are either homomeric or additionally include TRPC1. Detection of TRPC4 mRNA by RT-PCR has been reported in immature human adipocytes (Hu et al. (2009) Characterization of calcium signalling pathways in human preadipocytes J Cell. Physiol. 220, 765-770) but no role for TRPC4 in mature adipocytes has previously been recognised. In the above noted studies of Sukumar et al., no TRPC4 mRNA was detected in mouse 3T3-L1 cells, which were employed as an extensively characterised model of in vivo adipocytes. In contrast, marked up-regulation of TRPC1 mRNA (15.5 times) and TRPC5 mRNA (almost 40 times) was observed in differentiated mature 3LT3-L1 cells.

TRPC4 and TRPC5 proteins share about 65% sequence identity. The proteins were initially identified by their sequence similarity with the *D. melanogaster* TRP protein (40% sequence identity), the founding member of the TRP superfamily of proteins. TRPC4 is recognised to be expressed in a broad range of tissues, including brain, peripheral sensory neurones, endothelium, and intestinal smooth muscle. In smooth muscle cells, TRPC4 channels are gated by muscarinic acetylcholine receptors and contribute more than 80% to the muscarinic receptor-induced cation current. In these cells, TRPC4 channels couple muscarinic receptors to smooth muscle cell depolarization, voltage-activated $Ca^{2+}$ influx, and contraction, and thereby accelerate small intestinal motility. TRPC5 has previously been suggested to be predominantly expressed in the brain. Although channel properties are similar to those of TRPC4, TRPC5 channels are cold-sensitive and can be activated by a variety of additional stimuli, including a rise of cytosolic $Ca^{2+}$ [Beck et al. (2013) J. Biol. Chem. 288, 19471-19483].

The amino acid sequence for human TRPC 4 can be found in UniProtKB database as entry Q9UBN4.

The amino acid sequence for human TRPC5 can be found in the UniProtKB database as entry Q9UL62.

Based on the observation that antibody inhibition of TRPC5-containing channels in isolated 3T3-L1 cells led to increased secretion of adiponectin, Sukumar et al. went on to investigate the role of TRPC5-containing channels in vivo. For this purpose transgenic mice were employed capable of expressing a faulty TRPC5 protein (DNT5) which disrupts ion channel function under the control of a doxycycline-regulated transgene. As predicted, DNT5 expression occurred in adipose tissue of doxycycline-treated double transgenic mice. Such mice and controls were either fed for 6 weeks chow diet or a high-fat diet which induced inflammatory indicators but not obesity. The double transgene mice had as expected increased circulating adiponectin which was linked to anti-inflammatory effects but showed no difference in weight or well-being compared to control mice. Hence the study did not investigate excess weight gain or its consequences. Furthermore, Kubota et al. (2007) Cell. Metabolism 6, 55-68 had previously reported linkage of increased adiponectin to increased food intake in mice which directly points away from consideration of inhibition of TRPC5-comprising channels as a means of reducing excess weight gain.

Moreover, the same studies of Sukumar et al. also showed no effect of the DNT5 mutant protein in fat-fed mice on plasma insulin consistent with the animals not being insulin-resistant. Hence, nothing could be gleaned from such studies concerning value of inhibiting TRPC5-containing channels in relation to insulin resistance associated with Type II diabetes.

Hu et al. (2009) Mol. Endrocrinol. 23, 689-699 reported increased TRPC1, TRPC5 and TRPC6 expression in adrenal medulla in pigs with metabolic syndrome. However, no information is provided on the functional implications of those observations for treatment of metabolic syndrome per se. Increases in protein expression can reflect a role of a mechanism in driving a condition or an attempt by the system to overcome the condition. It is therefore not possible to glean from those studies that inhibition of TRPC5-containing channels would be beneficial, adverse or lacking in effect in metabolic syndrome.

As noted above, anti-murine TRPC5 antibodies are known which will block function of TRPC5-containing ion channels in differentiated 3T3-L1 cells. Sukumar et al ibid also reported knock down of TRPC1 and TRPC5 expression in such cells as model adipocytes using siRNAs. The same disclosure additionally reports identification of various dietary fatty acids, e.g. linolenic acid, as inhibitors of function of human TRPC-5 homomeric or TRPC1/5 heteromeric channels as expressed in HEK293 cells. Screening using HEK239 cells expressing TRPC5 has identified other natural products as inhibitors of TRPC5 ion channel function, more particularly galangin (a natural product from ginger), resveratrol (a red wine component and vitamin C [Naylor et al. (2016) Brit. J. Pharmacol. 173, 562-574; Naylor et al. (2011) J. Biol. Chem. 286, 5078-5086]. However, such studies do not add to the pool of information on therapeutic value of inhibiting TRPC channels.

Various small molecule inhibitors of TRPC5-containing channels which target TRPC5 have also been identified, see for example WO 2014/143799, WO 2016/023826, WO 2016/023825, WO 2016/023831, WO 2016/023830 and WO 2016/023832 which discloses such inhibitors as having value as anxiolytic agents. Various agents, including small molecules, have also been reported as inhibitors of TRPC4 ion channel function, see for example WO2011/022638 which teaches various such inhibitors, but only in the context of treatment of neuropathic pain, including such pain associated with diabetes. Miller et al. (2011) J. Biol. Chem. 286, 33436-33446 reports identification of a compound ML204 as a relatively selective TRPC4/C5 antagonist which displays at least 20-fold higher selectivity for TRPC4 over a collection of other ion channels including TRPC6 and members of other TRP sub-families, but only in the context of provision of a further research tool for investigating functional significance of TRPC4/C5-containing channels. Westlund et al. (2014) Neuroscience 262, 165-175 reports that rats with a TRPC4 knock-out mutation or treated with ML204 have higher tolerance to visceral pain. For further information on inhibitors of TRPC4 and/or TRPC5 reference may also be made to Bon and Beech (2013) ibid. However, no teaching is provided which would direct consideration of any such inhibitor in relation to weight control or insulin resistance.

SUMMARY OF THE INVENTION

The present inventors have now found that genetically-modified mice in which the TRPC4 protein or TRPC5 protein is absent, designated as TRPC4 knockout mice ($C4^{KO}$) and TRPC5 knockout mice ($C5^{KO}$) respectively, have improved weight control when on a high fat diet providing excess calorie intake over an 8 week period compared to control wild-type littermates on the same diet. The control mice gained excess total fat and fat pad weights as expected. In contrast, the $C4^{KO}$ and $C5^{KO}$ mice on the high fat diet were after the same period strikingly similar to mice on chow diet, showing only normal weight gain as the mice matured. $C4^{KO}$ and $C5^{KO}$ mice on chow diet showed no significant difference in body weight or fat pad weight to littermate controls. Evidence as presented herein suggests that the anti-obesity effect of TRPC4 knockout or TRPC5 knockout may be explained by white adipocytes shifting to a thermogenic ("energy-burning") phenotype, commonly referred to as adipocyte beiging.

A new approach to combating obesity and other conditions associated with obesity such as insulin resistance is thus proposed relying on inhibition of TRPC4 and/or TRPC5-containing channels, more particularly such channels as present in adipocytes. It is envisaged that such channels may also include heteromeric channels including TRPC1. The terms TRPC4, TRPC5 and TRPC1 as used herein will be understood to include any native form of those proteins as occurs in ion channels present in adipocytes, including adipocytes of human white adipose tissue.

Accordingly in one aspect, the present invention provides an inhibitor which directly targets a TRPC ion channel comprising TRPC4 and/or TRPC5 as present in adipocytes for use in the treatment or prophylaxis of a condition selected from obesity, insulin resistance, metabolic syndrome, non-alcoholic fatty liver disease (NAFLD) and non-alcoholic steatohepatitis (NASH).

In a further aspect there is provided cosmetic use of an inhibitor which directly targets a TRPC ion channel comprising TRPC4 and/or TRPC5 as present in adipocytes to reduce or inhibit excess weight gain. Such use will be understood to encompass non-therapeutic use of a suitable inhibitor e.g. where a suitable inhibitor is supplied as a non-prescription over-the-counter aid to weight reduction or prevention of excess weight gain.

The inhibitor may be any agent which acts directly on a TRPC ion channel comprising TRPC4 and/or TRPC5 as present in adipocytes, suitably the inhibitor is a small molecule inhibitor. The inventors have found that the compound disclosed as Example 31 in WO 2014/143799 (also designated herein as "C31") is a potent TRPC4 and TRPC5 inhibitor and is therefore suitable for any of the uses disclosed herein.

The present invention also provides certain novel compounds. The novel compounds are suitable for use in inhibiting TRPC4 and/or TRPC5 ion channels, more particularly the novel compounds may be for any of the uses described herein, particularly the novel compounds are inhibitors which directly target a TRPC ion channel comprising TRPC4 and/or TRPC5 as present in adipocytes for use in the treatment or prophylaxis of a condition selected from obesity, insulin resistance, metabolic syndrome, non-alcoholic fatty liver disease (NAFLD) and non-alcoholic steatohepatitis (NASH). A specific novel compound of the invention is a compound of the formula (IXa), or a pharmaceutically acceptable salt thereof (also designated herein as "DE2").

BRIEF DESCRIPTION OF THE DRAWINGS

Embodiments of the invention are further described hereinafter with reference to the accompanying drawings, in which.

DETAILED DESCRIPTION

Figure 1:
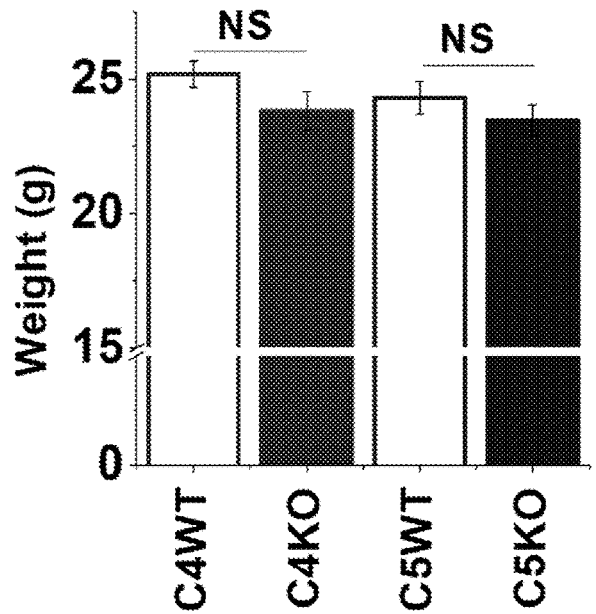
FIG. 1 demonstrates that TRPC4 knockout mice and TRPC5 knockout mice demonstrated normal body weight on a chow diet. (A) Body weight (mean±SEM, n=6). (B) Subcutaneous white adipose tissue (scWAT) fat pad weight (mean±SEM, n=6). NS indicates not statistically significantly different. C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice.
Figure 1:
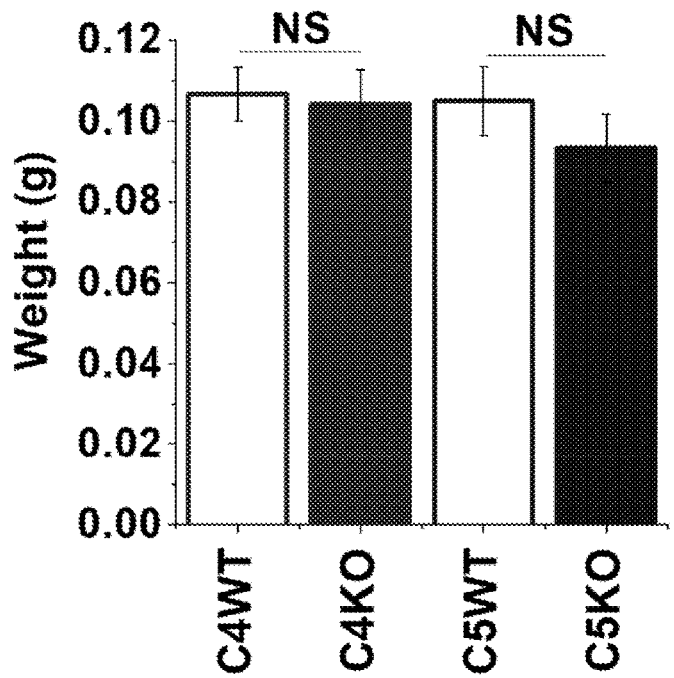

The present invention relates to an inhibitor which directly targets a transient receptor potential canonical (TRPC) ion channel comprising TRPC4 and/or TRPC5 as present in adipocytes for use in the treatment or prophylaxis of a condition selected from: obesity, insulin resistance, metabolic syndrome, non-alcoholic fatty liver disease (NAFLD) and non-alcoholic steatohepatitis (NASH). It is envisaged that the use of such an inhibitor may extend to the treatment or prophylaxis of insulin resistance associated with Type II diabetes or development of Type II diabetes (pre-diabetes).

The TRPC inhibitors described herein are capable of inhibiting a TRPC ion channel, as present in adipocytes, comprising TRCP4 or TRPC5. Optionally, such an inhibitor will directly target a TRPC ion channel, as present in adipocytes, comprising TRPC4. Optionally, such an inhibitor will directly target a TRPC ion channel, as present in adipocytes, comprising TRPC5. Also, it will be understood that ion channels comprising TRPC4, TRPC5 or both TRPC4 and TRPC5 may also include other channel proteins, in particular other TRPC proteins. Accordingly, it will be appreciated that the TRPC inhibitor may also be capable of inhibiting an ion channel wherein the TRPC ion channel further comprises another TRPC protein, for example TRPC1. Optionally, such an inhibitor will directly target a TRPC ion channel, as present in adipocytes, wherein the channel comprises TRPC4, TRPC5 and TRPC1.

A TRPC channel which is directly targeted by the inhibitors described herein may be a homomeric channel or a heteromeric channel. When the channel is a homomeric channel it may comprise four TRPC4 proteins or four TRPC5 proteins. When the ion channel is a heteromeric channel, the channel comprises (i) at least one TRPC4 and three other TRP proteins, at least one of which is not TRPC4; or (ii) at least one TRPC5 and three other TRP proteins, at least one of which is not TRPC5. In embodiments the ion channel may optionally comprise TRPC4 and TRPC5. Alternatively, the channel may optionally comprise TRPC4 and TRPC1 or TRPC5 and TRPC1. Optionally the channel may comprise TRPC4, TRPC5 and TRPC1. Accordingly, the heteromeric channel is intended to encompass any TRPC ion channel provided that the channel includes at least one TRPC 4 or one TRPC 5 protein as a component of the ion channel. Representative examples of heteromeric channels, include, but are not limited to, for example the ion channel may comprise one TRPC4 and three TRPC1; two TRPC4 and two TRPC1; three TRPC4 and one TRPC1; one TRPC5 and three TRPC1; two TRPC5 and two TRPC1; three TRPC5 and one TRPC1; one TRPC4 and three TRPC5; two TRPC4 and two TRPC5; three TRPC4 and one TRPC5; one TRPC4 and three other TRP proteins, two TRPC 4 and two other TRP proteins; three TRPC4 and one other TRP protein; two TRPC5, one TRPC1 and one other TRP protein; or one TRPC4, one TRPC5, one TRPC1 and one other TRP protein etc.

It will be appreciated that an inhibitor operated in accordance with the invention may inhibit the function or expression of TRPC4 and/or TRPC5. Preferably, an inhibitor operated in accordance with the invention may inhibit the function or expression of TRPC4 and/or TRPC5. TRPC4 is a known protein encoded by the TRPC4 gene. The amino acid sequence for human TRPC4 may be found in the UniProtKB database as entry Q9UBN4. TRPC5 is a known protein encoded by the TRPC5 gene. The amino acid sequence for human TRPC5 may be found in the UniProtKB database as entry Q9UL62. Reference to the ion channel "as present in adipocytes" refers to the form of the ion channel present in adipocytes and includes natural variants of the channels, including, for example splice variants and/or naturally occurring variants of the TRPC proteins forming the ion channel. It is to be understood that the ion channels comprising TRPC4 and/or TRPC5 are formed in adipocyte cells. However, such channels may also be present in other tissues. The inhibitor may therefore act on channels present in adipocytes or other tissues to provide the therapeutic and cosmetic effects described herein, for example the treatment of obesity.

The "TRPC inhibitor" refers to any agent which acts directly on a TRPC ion channel, as present in adipocytes, comprising TRPC4 and/or TRPC5 to inhibit the function of the ion channel. A TRPC inhibitor in accordance with the invention may inhibit the function or expression of TRPC4 and/or TRPC5. Inhibition of the ion channel by the TRPC inhibitor may include, for example, inhibiting or preventing the association of the TRP proteins which form the TRPC ion channel comprising TRPC4 and/or TRPC5. The inhibitor may act to inhibit the ion channel function. For example, the inhibitor may bind to the TRPC ion channel such that it blocks completely or reduces transport of cations ($Ca^{2+}$ and $Na^{+}$) into or out of the ion channel. Alternatively it might act allosterically to modulate the gating and opening probability of the channel. The inhibitor may be any agent which acts directly on a TRPC ion channel comprising TRPC4 and/or TRPC5 as present in adipocytes, suitably the inhibitor is a small molecule inhibitor. Particularly advantageously, the inventors have found that the compound disclosed as Example 31 in WO 2014/143799 (also designated herein "C31") is a potent TRPC4 and TRPC5 inhibitor and is therefore suitable for any of the uses disclosed herein.

The present invention has shown that when expression of TRPC4 or TRPC5 is inhibited, upon exposure to calorific excess in the form of a high fat diet: excess weight gain may be reduced, markers of inflammation in adipose tissue may be reduced; thermogenesis and mitochondrial respirations in adipose tissue may be increased; a protective effect against insulin resistance and glucose intolerance may be seen; weight gain in the liver may be decrease and ectopic fat in the liver may be reduced.

Advantageously, the inventors have discovered that mutations in the genes encoding TRPC4 and TRPC5 result in protection against hyperglycaemia, insulin-resistance, systemic and adipose tissue inflammation and steatosis associated with excess calorie intake.

Accordingly, the invention provides a TRPC inhibitor, wherein the inhibitor is a siRNA or antisense oligonucleotide. Where the inhibitor is a siRNA or antisense oligonucleotide, the inhibitor may inhibit expression of TRPC4 protein, TRPC5 protein or both.

Accordingly, the present invention provides an inhibitor which may be used to eliminate or reduce expression of TRPC4 and/or TRPC5 in adipocytes, wherein adipocytes are transformed with the polynucleotide in an antisense orientation such that there is reduction in, or elimination of, expression or level of native TRPC4 or TRPC5 polypeptide in such cells compared to untransformed cells. In accordance with the present invention, antisense polynucleotides have polynucleotide sequences which hybridize under stringent conditions to the nucleotide sequences encoding TRPC4 or TRPC5. Such sequences may be useful in down-regulating expression of TRPC4 and/or TRPC5. Whilst in certain embodiments, TRPC4 or TRPC5 may be down-regulated (suppressed) in adipocytes cells, it is envisaged that it may in certain circumstances be desirable to down-regulate both TRPC4 and TRPC5.

Accordingly, it will be understood that a suitable inhibitor may be capable of specifically reducing or eliminating expression of TRPC4 and/or TRPC5 in a sequence-specific manner. Such expression control may, for example, suitably be exerted at either the transcript or protein level. Accordingly, a TRPC4 or TRPC5 inhibitor may suitably be a small interfering RNA (siRNA) or antisense oligonucleotide which specifically targets, and inhibits expression of TRPC4 or TRPC5 respectively. For example such an inhibitor may operate to reduce or eliminate TRPC4 or TRPC5 mRNA transcript or protein accumulation in adipocytes. Conveniently, where it is desired to reduce or eliminate the expression of both TRPC4 and TRPC5, more than one inhibitor, each specifically targeting either TRPC4 or TRPC5 may be deployed. In preferred aspects, the inhibition of, and/or reduction in TRPC4 and/or TRPC5 expression may take place specifically in adipocytes, for example by using an siRNA construct the expression of which is driven by an adipocyte-specific promoter e.g. the PdgfRα or Adiponectin promoter.

The invention provides a TRPC inhibitor as defined herein, wherein the inhibitor is an antibody or an antigen-binding fragment thereof or a nanobody, affimer or adhiron. The antibody or antigen-binding fragment thereof may interact directly with the TRPC4 or TRPC5 proteins to prevent or inhibit the formation of the TRPC ion channel and/or which acts to directly inhibit the function of the ion channel for example by binding to the ion channel such that the transport of cations into or out of the channel is inhibited or prevented. In preferred embodiments, the inhibitor may be a monoclonal antibody or the antigen-binding fragment of an antibody is a fragment of a monoclonal antibody. Monoclonal antibody (mAb) as used herein refers to a highly-specific antibody directed against a single antigenic site, obtained from a population of substantially homogeneous antibodies, i.e., the individual antibodies comprising the population are identical except for possible naturally occurring mutations that may be present in minor amounts. Such monoclonal antibodies may be synthesised by methods which are well known in the art, for example by hybridoma culture, or by recombinant DNA methods. Such a monoclonal antibody may be a chimeric antibody (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Preferably, such an antibody binds TRPC4 and/or TRPC5. Preferably such an antibody is humanised, i.e. an antibody from a non-human species whereby the protein sequences have been modified to increase their similarity to antibody variants produced naturally in humans. An antibody for use in accordance with the invention may be, for example, an antibody that targets the E3 loop of a relevant TRPC ion channel forming protein to suppress channel function as discussed in Beech (2013) Circul. J. 77, 570-579.

Such an antibody may also usefully be provided as a conjugate, i.e. a heterogeneous molecule formed by the covalent attachment of one or more antibody fragment(s) to one or more polymer molecule(s).

In some embodiments the TRPC inhibitor is a small molecule of 2000 daltons or less. Suitable small molecule inhibitors for the uses and methods of the invention include, but are not limited to any of the small molecules set out herein.

Surprisingly the inventors have discovered that mutations in the genes encoding TRPC4 and TRPC5 result in an inability to gain excess total body weight and fat pad weight on high fat diet. Accordingly, the invention also provides a TRPC inhibitor, wherein the TRPC inhibitor is for use in the treatment or prophylaxis of obesity. Optionally, the TRPC inhibitor may be used in treatment or prevention of abdominal obesity. Typically, the TRPC inhibitor may be used in the treatment of adiposity. Optionally, TRPC inhibitor may be used in preventing the accumulation of visceral fat or reducing the amount of visceral fat in a subject treated with the inhibitor. Optionally, the TRPC inhibitor may be used in preventing the accumulation of subcutaneous fat or reducing the amount of subcutaneous fat in a subject treated with the inhibitor.

The TRPC inhibitors described herein may also be used in preventing the accumulation of ectopic fat or reducing the amount of ectopic fat in a subject. In particular, the TRPC inhibitor described herein may be used in preventing the accumulation of ectopic fat or reducing the amount of ectopic fat in the liver of a subject.

Optionally, the TRPC inhibitor may be used in the treatment or prophylaxis of insulin resistance in a subject. Commonly, the TRPC inhibitor may be used in the treatment or prophylaxis of insulin resistance in an obese subject. Typically, the insulin resistance is associated with Type II diabetes or prediabetes.

Accordingly, said inhibitor may be for use in the treatment or prophylaxis of metabolic syndrome. Where the inhibitor is for use for use in the treatment or prophylaxis of metabolic syndrome, the treatment of metabolic syndrome may comprise reducing abdominal obesity and/or reducing fasting blood glucose concentration. In certain embodiments the metabolic syndrome may be a syndrome that is not associated with the reduction of glucose levels.

The effect inhibitor may also be beneficial in the treatment of conditions associated with the conditions controlled by use of the inhibitor. For example control of obesity, ectopic fat, insulin-resistance and/or inflammation resulting from the use of the inhibitor may also provide beneficial effects in diseases and conditions associated with those conditions. Accordingly the inhibitor may be for use in the treatment or prevention of a disease or medical condition associated with obesity, excess ectopic fat, insulin-resistance and/or inflammatory cytokines arising from adipocytes. In embodiments the inhibitor is for use in the treatment or prevention of a condition selected from: coronary artery disease, cerebral artery disease, peripheral vascular disease, heart failure, dyslipidaemia, diabetic retinopathy, diabetic nephropathy diabetic neuropathy and cancer.

Additionally, it has been discovered that mutations in the genes encoding TRPC4 and TRPC5 result in greater expression of the mitochondrial proteins UCP1 and Cytochrome C in white adipose tissue indicating an increase in thermogenesis and that inhibition of the proteins encoded by these genes has a similar effect.

Accordingly, the invention also provides a TRPC inhibitor as defined herein, wherein the inhibitor reduces expression of TNFα or IL6 in adipose tissue in the subject treated with said inhibitor. Optionally, the inhibitor may reduce the expression of TNFα and IL6 in adipose tissue in the subject treated with said inhibitor.

Accordingly, the invention also provides a TRPC inhibitor, wherein the inhibitor increases mitochondrial respiration in adipose tissue in the subject treated with said inhibitor.

Accordingly, the invention also provides a TRPC inhibitor, wherein the inhibitor increases thermogenesis in adipose tissue in the subject treated with said inhibitor.

The inventors have previously found that elevated levels of TRPC1 and TRPC5 are negatively correlated with levels of adiponectin and in particular that levels of TRPC1 and TRPC5 are elevated in adipose tissue of subjects which display metabolic syndrome or major cardiovascular diseases. Consequently, measurement of TRPC1 levels may be of use in screening for subjects for which the TRPC inhibitor may be particularly effective. Accordingly, in any aspect of the invention, optionally, a TRPC inhibitor as defined herein may usefully be administered to a subject with elevated levels of TRPC1 in adipose tissue relative to a control level in order to treating or prevent a condition selected from; obesity, insulin resistance, metabolic syndrome, non-alcoholic fatty liver disease (NAFLD) and non-alcoholic steatohepatitis (NASH). It is envisaged that such use may also extend to the treatment or prophylaxis of insulin resistance associated with Type II diabetes or development of Type II diabetes (pre-diabetes).

The invention therefore further provides a TRPC inhibitor as herein before defined, wherein the inhibitor is administered to a subject predetermined to have an elevated level in adipose tissue relative to control of one or more screening targets selected from TRPC1 mRNA and/or protein, TRPC4 mRNA and/or protein and TRPC5 mRNA and/or protein.

The invention further provides a method of identifying a subject having an elevated level in adipose tissue relative to control of one or more screening targets selected from TRPC1 mRNA and/or protein, TRPC4 mRNA and/or protein and TRPC5 mRNA and/or protein. which comprises:
  a. determining the level of one or more screening targets selected from TRPC1 protein and/or mRNA, TRPC4 mRNA and/or protein and or TRPC5 mRNA and/or protein in a sample of adipose tissue from a subject; and
  b. selecting said subject for administration of the inhibitor if the level of said screening target exceeds a control level.

In certain aspects the method may optionally comprise determining the level of TRPC4 protein or mRNA in a sample of adipose tissue from a subject; and/or optionally determining the level of TRPC5 protein or mRNA in a sample of adipose tissue from a subject; and administering the inhibitor to the subject if the level of TRPC1 and TRPC4 exceed control levels, or if the level of TRPC1 and TRPC5 exceed control levels, or the level of TRPC1, TRPC4 and TRPC5 exceed control levels.

Specifically determining the level of TRPC1, TRPC4 and/or TRPC5 protein or mRNA in a sample of adipose tissue from a subject may conveniently be achieved by methods and devices which are well known in the art. For example by qPCR, microarray, Northern Blotting or Next generation sequencing where the target is mRNA, or e.g. Western Blotting, ELISA or mass spectrometry where the target is protein. Suitably the method may comprise the use of specific binding partners which selectively bind to a target molecule indicative of the presence or expression of a polynucleotide or polypeptide as hereinbefore defined. Target molecules may suitably be RNA molecules, DNA molecules, cDNA molecules or alternatively proteins or polypeptides encoded by a polynucleotide as hereinbefore defined. A variety of suitable array or chip-based or liquid-based capture technologies are well known in the art and suitable for the purpose.

Suitably the method may comprise using at least one binding partner selected from the group consisting of: complementary nucleic acids; aptamers; antibodies or antibody fragments. Suitable classes of binding partners for any given polynucleotide or protein will be apparent to the skilled person.

The method will be adapted to detect and quantify the levels of said polynucleotides or proteins present in the adipose tissue sample. This may be with reference to a positive control or alternatively with reference to an internal standard.

Preferably, the adipose tissue sample is an extract or lysate from an adipose cell or tissue. The adipose tissue sample may suitably be homogenized, processed, buffered and/or purified prior to quantification of the levels of TRPC1. Suitably the levels of the target molecules in the biological sample may be detected by direct assessment of binding between the target molecules and binding partners.

Advantageously, the present invention provides a compound as defined herein for use in therapy. The present invention further provides that any of the compounds defined herein may be used as a TRPC inhibitor for use in the treatment or prophylaxis of a condition selected from: obesity, insulin resistance, metabolic syndrome, non-alcoholic fatty liver disease (NAFLD) and non-alcoholic steatohepatitis (NASH). It is envisaged that the use of such an inhibitor may also extend to the treatment or prophylaxis of insulin resistance associated with Type II diabetes or development of Type II diabetes (pre-diabetes).

The present invention also provides for the cosmetic use of a TRPC inhibitor as defined herein, which directly targets TRPC ion channels comprising TRPC4 and/or TRPC5 as present in adipocytes to reduce or inhibit excess weight gain. Such use will be understood to encompass non-therapeutic use of a suitable inhibitor e.g. where a suitable inhibitor is supplied as a non-prescription over-the-counter aid to weight reduction or prevention of excess weight gain.

Such a TRPC inhibitor may therefore appropriately be formulated for cosmetic use, for example in tablet form. Such cosmetic compositions may contain the formulation in sufficient amounts to inhibit expression of TRPC4 and/or TRPC5 in adipocytes and a pharmaceutically acceptable carrier or excipient. Particularly, a cosmetic composition containing the formulation can be used to reduce or inhibit excess weight gain.

In one embodiment the inhibitor is a 2-aminoquinoline of the formula (I), or a pharmaceutically acceptable salt thereof:

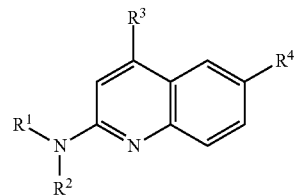

(I)

wherein
$R^1$ and $R^2$ are independently H or $C_{1-4}$ alkyl, or $R^1$ and $R^2$ together with the nitrogen to which they are attached form a 4 to 7 membered heterocyclyl, for example pyrrolidinyl, piperidinyl, piperazine, or homopiperidinyl;
$R^3$ is $C_{1-4}$ alkyl; and
$R^4$ is H, halo or $C_{1-4}$ alkyl.

In this embodiment a particular compound of the Formula (I) is ML204:

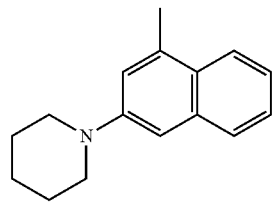

ML204

In another embodiment the inhibitor is a 3,5-bis(trifluoromethyl)pyrazole derivative, for example Pyr2 (BTP2, YM-58483):

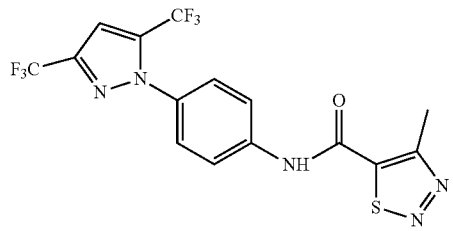

Pyr2 (BTP2, YM-58483)

In another embodiment the inhibitor is a steroid, for example pregnenolone or pregnanolone.

In another embodiment the inhibitor is a piperazine or piperidine derivative, for example BD1063, BD1047 or 4-IBP:

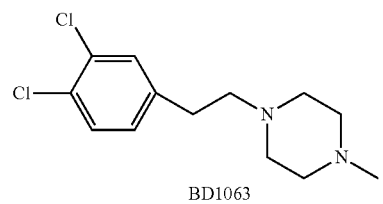

BD1063

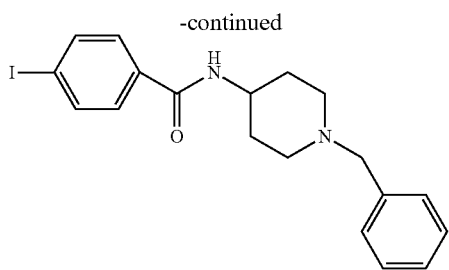

4-IBP

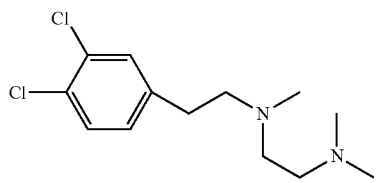

BD1047

In another embodiment the inhibitor is M084:

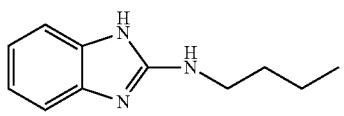

M084

In another embodiment the inhibitor is an N-phenylanthranilic acid derivative, for example flufenamic acid, mefenamic acid, niflumic acid, diclofenac or N-(p-amylcinnamoyl)anthranilic acid.

In an embodiment the inhibitor is a compound disclosed in WO 2014/143799. In this embodiment the inhibitor may be any one of the compound disclosed in the Examples of WO 2014/143799, which are described as TRPC5 inhibitors therein, or a pharmaceutically acceptable salt thereof. The inhibitor may be any of Compounds 1 to 640 described in Table A of WO 2014/143799, or a pharmaceutically acceptable salt thereof.

In embodiments the inhibitor is a compound of the Formula (II), or a pharmaceutically acceptable salt thereof:

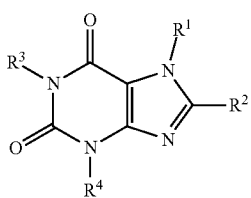

(II)

wherein:
$R^1$ is $C_{1-6}$ alkyl, $C_{2-6}$ alkenyl or $C_{2-6}$ alkynyl, each of which is optionally substituted with 1-4 $R^5$;
$R^2$ is $C_{1-6}$ alkyl, $C_{1-6}$ heteroalkyl, $C_{2-6}$ alkenyl, $C_{2-6}$ alkynyl, $C_{1-6}$ haloalkyl, halo, $C_{1-6}$ haloalkoxy, hydroxyl, $C_{1-6}$ alkoxy, $C_{3-7}$ cycloalkyloxy, $C_{6-10}$ aryl, $C_{6-10}$ aryloxy, $C_{7-16}$ arylalkoxy, amino, $C_{1-6}$ akylamino, $C_{2-12}$ dialkylamino, —S(O)$_x$R' (wherein x is 0, 1 or 2 and each R' is independently H or $C_{1-6}$ alkyl), heterocycloalkyl, heteroaryl, heteroaryloxy, sulfonamidyl, amido, urea, sulfonylurea, acyl, nitro, cyano,
wherein each $C_{1-6}$ alkyl, $C_{1-6}$ heteroalkyl, $C_{2-6}$ alkenyl, $C_{2-6}$ alkynyl, $C_{1-6}$ haloalkyl, $C_{1-6}$ haloalkoxy, hydroxyl, $C_{1-6}$ alkoxy, $C_{3-7}$ cycloalkyloxy, $C_6$-10 aryl, $C_{6-10}$ aryloxy, $C_{7-16}$ arylalkoxy, amino, $C_{1-6}$ akylamino, $C_{2-12}$ dialkylamino, —S(O)$_x$R', heterocycloalkyl, heteroaryl, heteroaryloxy, sulfonamidyl, amido, urea, sulfonylurea, acyl, is optionally substituted with 1-3 $R^6$;
$R^3$ is $C_{1-6}$ alkyl, $C_{1-6}$ heteroalkyl, $C_{3-7}$ cycloalkyl, $C_{2-6}$ alkenyl, $C_{2-6}$ alkynyl, $C_{2-6}$ hydroxyalkyl, or $C_{1-6}$ alkoxy, each of which is optionally substituted with 1-4 $R^7$;
$R^4$ is $C_{1-6}$ alkyl, $C_{1-6}$ heteroalkyl, $C_{2-6}$ alkenyl or $C_{2-6}$ alkynyl, each of which is optionally substituted with 1-4 $R^8$;
$R^5$, $R^6$, $R^7$, and $R^8$ are each independently hydrogen, $C_{1-6}$ alkyl, $C_{1-6}$ heteroalkyl, halo, $C_{1-6}$ haloalkyl, $C_{1-6}$ haloalkoxy, hydroxyl, $C_{1-6}$ alkoxy, amino, $C_{1-6}$ alkylamino, $C_{2-12}$ dialkylamino, cyano, nitro, amido, $C_{1-6}$ alkylamido, $C_{2-12}$ dialkylamido, —S(O)$_x$R' (wherein x is 0, 1 or 2), —C(O)OR', —C(O)R', $C_{3-7}$ cycloalkyl, $C_{6-10}$ aryl, heterocycloalkyl, or heteroaryl, wherein each R' is independently H or $C_{1-6}$ alkyl,
wherein each of $C_{1-6}$ alkyl, $C_{1-6}$ heteroalkyl, $C_{1-6}$ haloalkyl, $C_{1-6}$ haloalkoxy, hydroxyl, $C_{1-6}$ alkoxy, amino, $C_{1-6}$ alkylamino, $C_{2-12}$ dialkylamino, amido, $C_{1-6}$ alkylamido, $C_{2-12}$ dialkylamido, —C(O)O—$C_{1-6}$ alkyl, $C_{3-7}$ cycloalkyl, $C_{6-10}$ aryl, heterocycloalkyl, or heteroaryl is optionally substituted with 1-3 $R^9$; and
each $R^9$ is independently $C_{1-6}$ alkyl, $C_{1-6}$ heteroalkyl, $C_{1-6}$ haloalkyl, $C_{1-6}$ haloalkoxy, heterocycloalkyl, $C_{6-10}$ aryl, heteroaryl, $C_{4-10}$ cycloalkylalkyl, heterocycloalkyl-$C_{1-6}$ alkyl, $C_{7-16}$ arylalkyl, heteroaryl-$C_{1-6}$ alkyl, halo, hydroxyl, $C_{1-6}$ alkoxy, $C_{6-10}$ aryloxy, $C_{7-16}$ arylalkoxy, $C_{2-8}$ alkoxyalkoxy, amino, $C_{1-6}$ akylamino, $C_{2-12}$ dialkylamino, $C_{1-6}$ alkyl-amino-$C_{1-6}$ alkyl, $C_{1-6}$ alkyl-amino-$C_{2-12}$ dialkyl, —S(O)$_x$R' (wherein x is 0, 1 or 2), sulfonamidyl, amido, urea, sulfonylurea, acyl, —C(O)—$C_{1-6}$ alkyl, —C(O)—$C_{6-10}$ aryl, —NHC(O)—$C_{1-4}$ alkyl, —NHC(O)—$C_{6-10}$ aryl, —C(O)NR'R', —C(O)NH—$C_{6-10}$ aryl, —C(O)OR', —OC(O)R', acyl, nitro, or cyano.

In embodiments $R^1$ is $C_{1-6}$ alkyl optionally substituted by $R^5$.

In embodiments $R^2$ is selected from $C_{1-6}$ alkyl, $C_{1-6}$ alkoxy, amino, $C_{1-6}$ alkylamino, di-$C_{1-6}$ alkylamino, $C_{1-6}$ alkyl-S(O)$_2$—, $C_{6-10}$ aryl, $C_6$10 aryloxy, 5-6 membered heteroaryloxy, wherein any aryl or heteroaryl is optionally substituted by halo, $C_{1-4}$ alkyl, $C_{1-4}$ haloalkyl, $C_{1-4}$ alkoxy or $C_{1-4}$ haloalkoxy.

In embodiments $R^3$ is selected from $C_{1-6}$ alkyl, hydroxy$C_{2-6}$ alkyl or $C_{1-6}$ alkoxy.

In embodiments $R^4$ is $C_{1-6}$ alkyl.

In embodiments $R^5$ is $C_{3-6}$ cycloalkyl, 4-7 membered heterocyclyl, $C_{6-10}$ aryl, $C_{6-10}$ aryloxy, 5-6 membered heteroaryloxy, wherein any cycloalkyl, heterocyclyl, aryl or heteroaryl is optionally substituted by halo, $C_{1-4}$ alkyl, $C_{1-4}$ haloalkyl, $C_{1-4}$ alkoxy or $C_{1-4}$ haloalkoxy.

The compound of formula (II) may be a compound of the formula (III), or a pharmaceutically acceptable salt thereof:

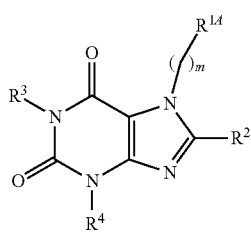

(III)

wherein
- $R^{1A}$ is phenyl or a 5 or 6 membered heteroaryl, which aryl or heteroaryl is optionally substituted by 1 or 2 substituents independently selected from halo, $C_{1-6}$ alkyl, $C_{1-6}$ haloalkyl and $C_{1-6}$ haloalkoxy;
- $R^2$ is $C_{1-6}$ alkoxy, or $C_{6-10}$ aryloxy substituted by 1-3 $R^6$;
- $R^3$ is hydroxy-$C_{1-6}$ alkyl or $C_{1-6}$ heteroalkyl;
- $R^4$ is $C_{1-6}$ alkyl;
- each $R^6$ is independently selected from halo, $C_{1-6}$ alkyl, $C_{1-6}$ haloalkyl or $C_{1-6}$ haloalkoxy; and
- m is 1, 2 or 3.

It may be that $R^{1A}$ is selected from phenyl, thiazolyl, oxazolyl and pyridyl, each of which is optionally substituted by 1 or 2 substituents independently selected from halo, $C_{1-6}$ alkyl and $C_{1-6}$ haloalkyl. Preferably, $R^{1A}$ is phenyl optionally substituted by 1 or 2 substituents independently selected from halo, $C_{1-4}$ alkyl, $C_{1-4}$ alkoxy, $C_{1-4}$ haloalkyl and $C_{1-4}$ haloalkoxy. Preferably m is 1.

It may be that the compound of formula (II) is a compound selected from:

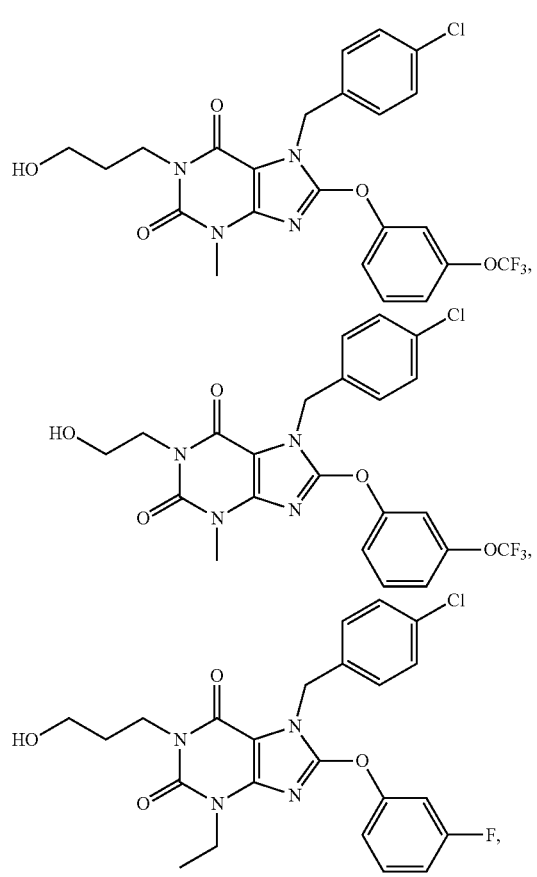

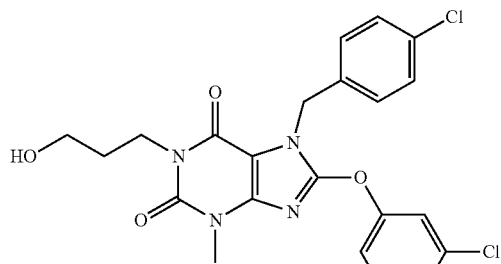

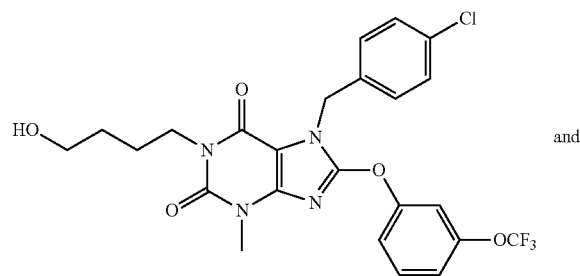

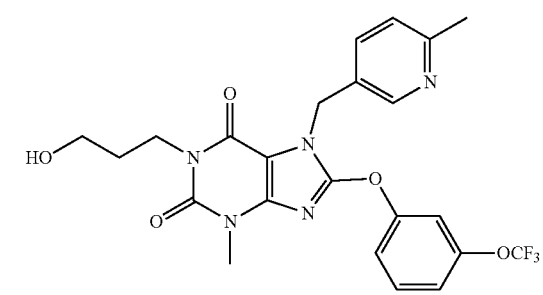 [SMILES: Cc1ccc(Cn2c(Oc3cccc(OC(F)(F)F)c3)nc3c2c(=O)n(CCCO)c(=O)n3C)cn1]

or a pharmaceutically acceptable salt thereof.

In a specific embodiment the compound of formula (II) is

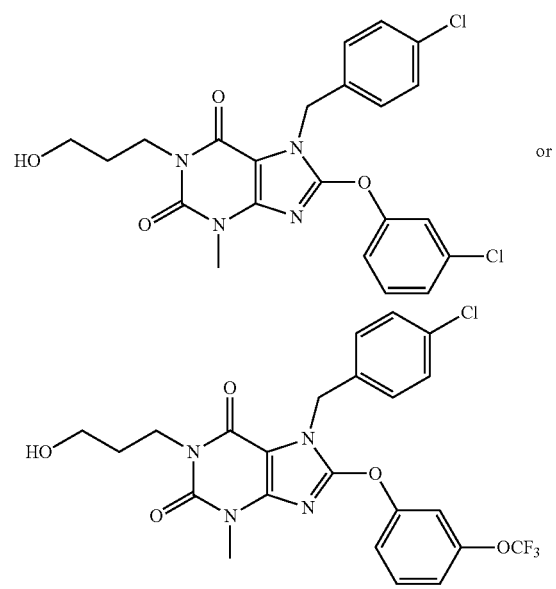

or pharmaceutically acceptable salt thereof.

In an embodiment the inhibitor is:

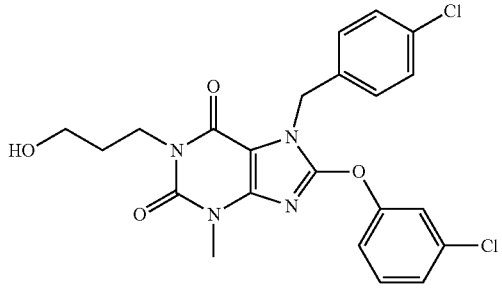 [SMILES: Cn1c(=O)n(CCCO)c(=O)c2c1nc(Oc1cccc(Cl)c1)n2Cc1ccc(Cl)cc1]

or pharmaceutically acceptable salt thereof.

Compound 31 disclosed in WO 2014/143799 is a potent inhibitor of TRPC4 and TRPC5. Accordingly a preferred inhibitor is C31, or a pharmaceutically acceptable salt thereof:

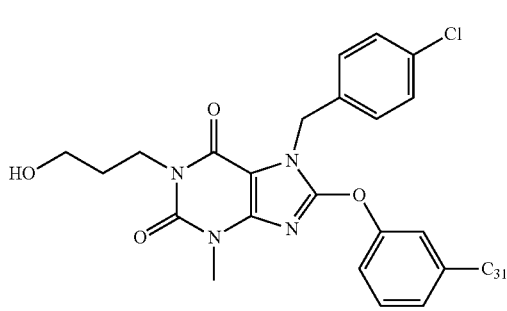

In another embodiment the inhibitor is a compound described in WO 2016/023826, WO 2016/023825, WO 2016/023831, WO 2016/023830 or WO 2016/023832.

The inhibitor may be a compound of the formula (IV) or a pharmaceutically acceptable salt thereof:

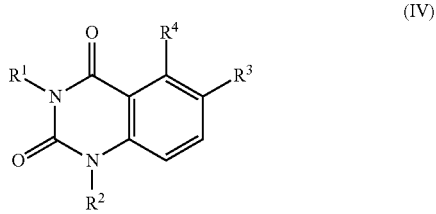

wherein $R^1$ is $C_{2-10}$ hydroxyalkyl, optionally substituted with 1-3 $R^5$;

$R^2$ is H, $C_{1-6}$ alkyl, $C_{2-6}$ alkenyl, $C_{2-6}$ alkynyl, $C_{3-10}$ cycloalkyl, $C_{1-6}$ hydroxyalkyl, or $C_{1-6}$ alkoxy;

$R^3$ is $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ hydroxyalkyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{0-12}$ aryl-$C_{1-6}$ alkyl-OR$^5$, 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein $R^3$ is optionally substituted with 1-5 $R^5$;

$R^4$ is $C_{1-6}$ alkyl, $C_{1-6}$ acyl, $C_{3-6}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ hydroxyalkyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$-aryl-$C_{1-6}$ alky-OR', 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein $R^4$ is optionally substituted with 1-5 $R^5$;

each $R^5$ is independently H, $C_{1-6}$ alkyl, $C_{2-6}$ alkenyl, $C_{2-6}$ alkynyl, $C_{1-6}$ acyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ hydroxyalkyl, amino, $C_{6-12}$ aryl, 5-14-membered heteroaryl, $C_{6-12}$ aryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alky-OR$^6$, 5-14-membered heteroaryloxy, each of which is optionally substituted with 1-5 $R^6$; and each $R^6$ is independently H, $C_{1-6}$ alkyl, $C_{1-6}$ alkoxy, $C_{1-6}$ cycloalkyloxy, halo, $C_{1-6}$ haloalkyl, $C_{1-6}$ haloalkoxy, hydroxyl, $C_{1-6}$ hydroxyalkyl, amino, $C_{1-6}$ alkylamino, $C_{2-12}$ dialkylamino, cyano, nitro, —C(O)NH$_2$—C(O)NHC$_{1-4}$ alkyl, —C(O)NH(C$_{1-4}$ alkyl)$_2$, —NHC(O)C$_{1-4}$ alkyl, —N(C$_{1-4}$ alkyl)C(O)C$_{1-4}$ alkyl, —C(O)OC$_{1-4}$ alkyl, —C(O)OH, —OC(O)C$_{1-6}$ alkyl, —C(O)C$_{1-6}$ alkyl, nitro, or cyano.

In embodiments $R^1$ is $C_{2-6}$ hydroxyalkyl, for example 3-hydroxypropyl.

In embodiments R2 is C1-4 alkyl, for example methyl

In embodiments R3 is C1-6 alkoxy, C1-6 haloalkoxy, phenyl or phenoxy (for example methoxy, ethoxy, propoxy, trifluoromethoxy or butoxy, phenyl, phenoxy), wherein a phenyl or phenoxy in R3 is optionally substituted with one or more fluorine, chlorine or —OCF3 group.

In embodiments R4 is benzyl or isopropyl optionally substituted with one or more, fluorine, chlorine or —OCF3.

The compound of formula (IV) may be a compound disclosed in Claim 10 of WO 2016/023826 selected from:

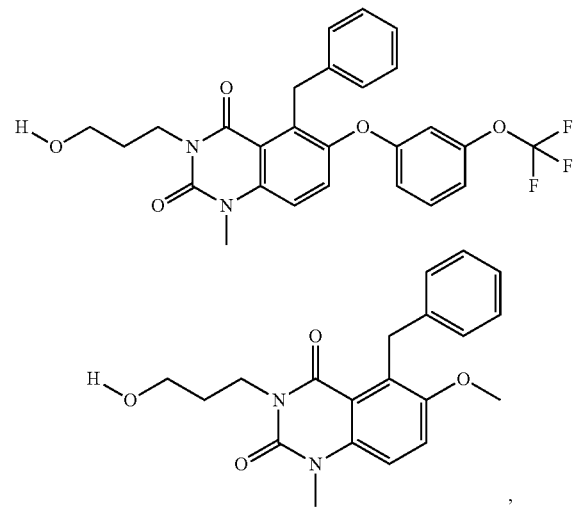

-continued
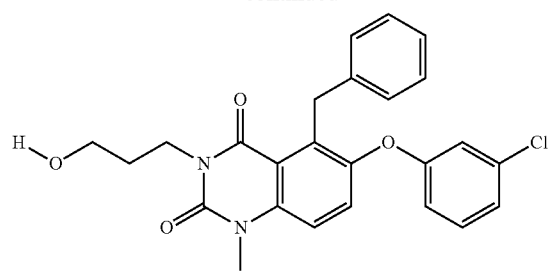
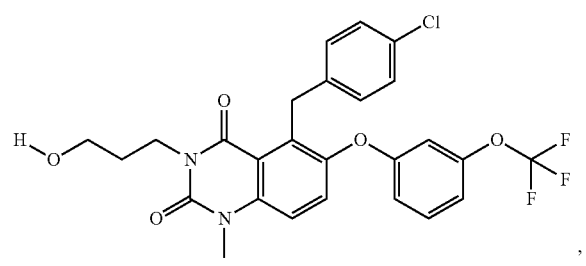
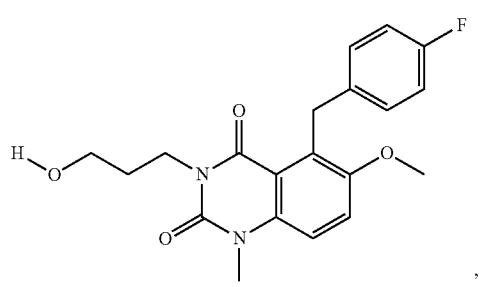
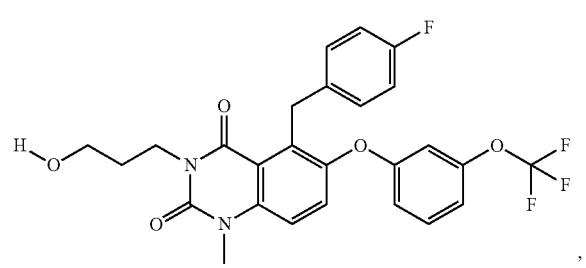
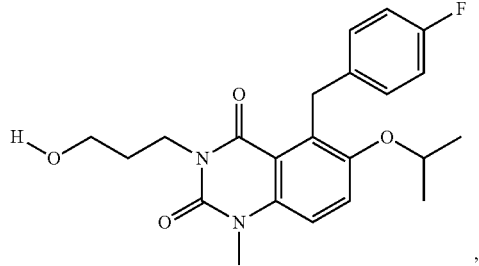
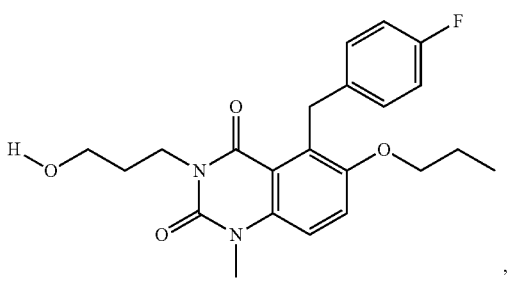
,
-continued
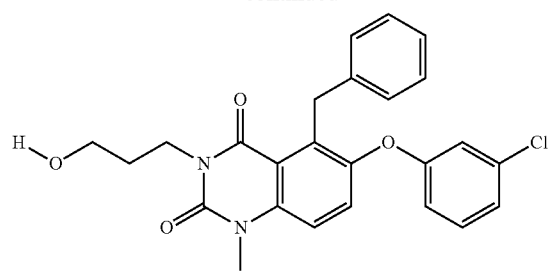
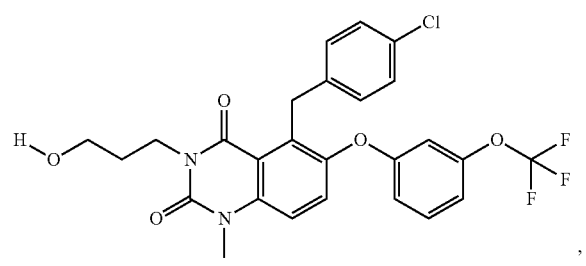
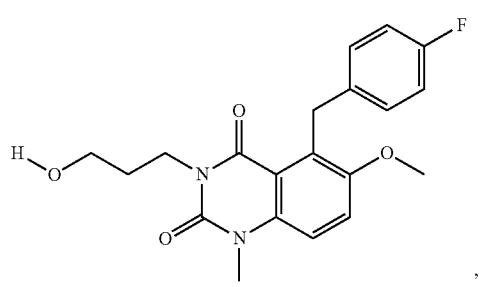
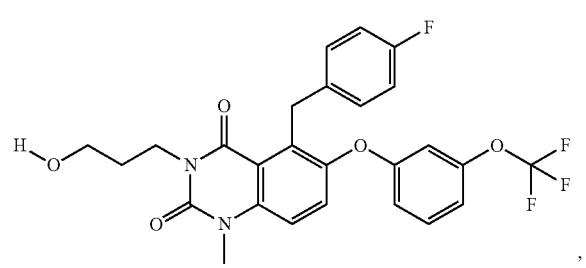
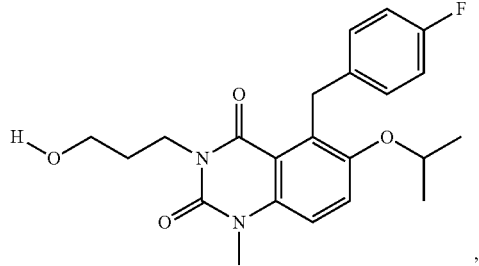
, and
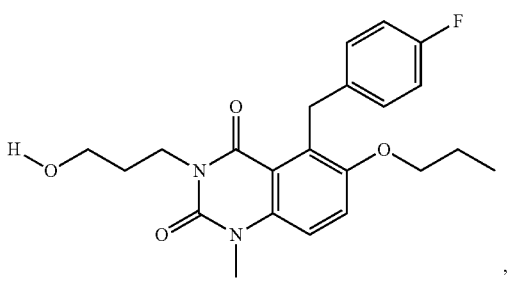
;
or a pharmaceutically acceptable salt thereof.
Compounds of the formula (IV) may be prepared as described in WO 2016/023826.
In an embodiment the inhibitor is a compound of the formula (V), or a pharmaceutically acceptable salt thereof:

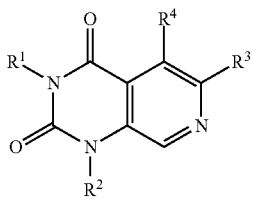

(V)

wherein
- $R^1$ is $C_{2-10}$ hydroxyalkyl optionally substituted with 1-3 $C_{3-10}$ cycloalkyl groups;
- $R^2$ is H, $C_{1-6}$ alkyl, $C_{2-6}$ alkenyl, $C_{2-6}$ alkynyl, $C_{3-10}$ cycloalkyl, $C_{1-10}$ hydroxyalkyl, or $C_{1-6}$ alkoxy;
- $R^3$ is $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxy, $C_{1-10}$ hydroxyalkyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$aryl-$C_{1-6}$alky-OR', 5-14-membered heteroaryloxy, 3-18-membered heterocycloalkyl, amino, $C_{1-6}$ alkylamino, $C_{2-12}$dialkylamino, —C(O)NR'R', —NR'C(O)R', urea, sulfonylurea, nitro, or cyano, wherein each R' is independently H or $C_{1-6}$ alkyl and wherein $R^3$ is optionally substituted with 1-5 $R^5$;
- $R^4$ is H, $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxy, $C_{1-10}$ hydroxyalkyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alkyl-OR', 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein $R^4$ is optionally substituted with 1-5 $R^5$; and
- each $R^5$ is independently H, $C_{1-6}$ alkyl, halo, $C_{1-6}$ haloalkyl, $C_{1-6}$ haloalkoxy, hydroxy, $C_{1-6}$ alkoxy, $C_{6-12}$aryl, 5-14-membered heteroaryl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alkyl-OR', 5-14-membered heteroaryloxy, —C(O)OR', —OC(O)R', —C(O)R', nitro, or cyano, wherein each R' is independently H or $C_{1-6}$ alkyl.

In embodiments in the compound of formula (V) $R^1$ is $C_{2-6}$ hydroxyalkyl, for example 3-hydroxypropyl.

In embodiments in the compound of formula (V) $R^2$ is $C_{1-4}$ alkyl, for example methyl.

In embodiments in the compound of formula (V) $R^3$ is phenyl, phenyl$C_{1-4}$alkoxy or phenyl$C_{1-4}$ alkyl each of which is optionally substituted with one or more substituent selected from chloro, $C_{1-4}$ alkyl, —CF$_3$ or —OCF$_3$. For example $R_3$ is phenoxy or phenyl each of which is optionally substituted with one or more chloro, $C_{1-4}$ alkyl or —OCF$_3$. Suitably $R_3$ is isopropyltoluene, chlorophenoxy, chlorophenyl, or trifluoromethoxyphenyl.

In embodiments in the compound of formula (V) $R_4$ is H, $C_{1-6}$ alkyl or phenyl-$C_{1-4}$ alkyl, wherein the phenyl is optionally substituted by one or more halo. For example $R_4$ is $C_{1-6}$ alkyl or phenyl-$C_4$ alkyl, wherein the phenyl is optionally substituted by one or more chloro. For example $R_4$ is benzyl optionally substituted by chloro.

The compound of formula (V) may be a compound disclosed in claim 13 of WO2016/023825 selected from:

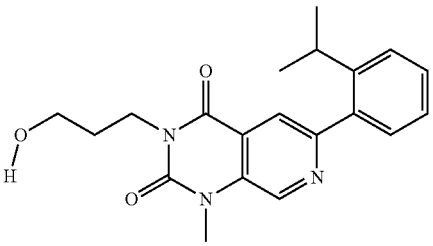

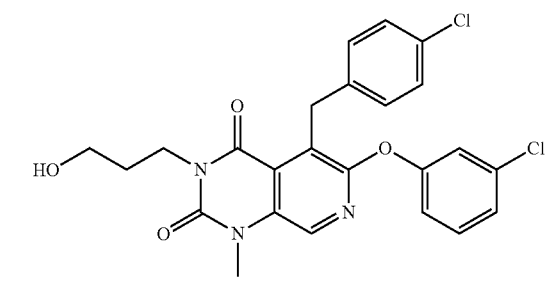

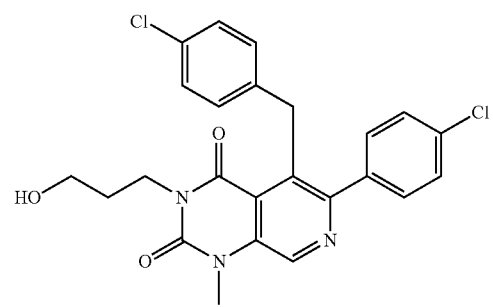

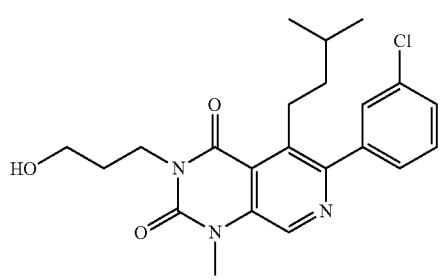

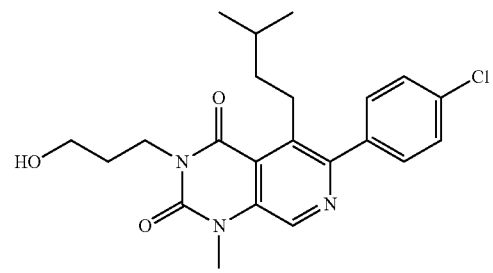

-continued

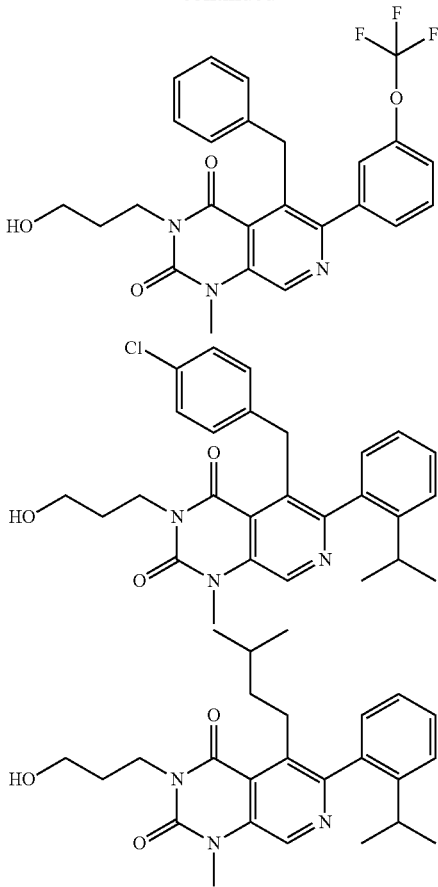

or a pharmaceutically acceptable salt thereof.

Compounds of the formula (V) may be prepared as described in WO2016/023825.

In an embodiment the inhibitor is a compound of the formula (VI), or a pharmaceutically acceptable salt thereof:

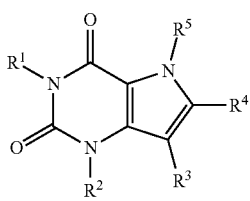

(VI)

wherein
$R^1$ is $C_{2-10}$ hydroxyalkyl, optionally substituted with 1-3 $R^6$;
$R^2$ is H, $C_{1-6}$ alkyl, $C_{2-6}$ hydroxyalkyl, $C_{3-10}$ cycloalkyl, $C_{2-6}$ alkenyl, $C_{2-6}$ alkynyl, or $C_{1-6}$ alkoxy;
$R^3$ is H, $C_{1-6}$ alkyl, $C_{2-6}$ alkenyl, $C_{2-6}$ alkynyl, $C_{1-6}$ alkoxy, $C_{1-6}$ acyl, $C_{3-10}$ cycloalkyl, halo, hydroxyl, $C_{6-12}$aryl, 5-14-membered heteroaryl, 3-18-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein each $R^3$ is optionally substituted with 1-4 $R^6$
$R^4$ is H, $C_{1-6}$ alkyl, $C_{2-6}$ alkenyl, $C_{2-6}$ alkynyl, $C_{1-6}$ acyl, $C_{1-6}$ alkoxy, $C_{4-10}$ cycloalkyloxy, halo, $C_{1-6}$ haloalkyl, $C_{1-6}$ haloalkoxy, hydroxy, $C_{1-6}$ alkylthio, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$alkyl, —O—$C_{1-6}$alkyl-$C_{6-12}$ aryl, —$C_{6-12}$ aryl-$C_{1-6}$ alky-OR', 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein $R^4$ is optionally substituted with 1-4 $R^7$;
$R^5$ is H, $C_{1-6}$ alkyl, $C_{2-6}$ alkenyl, $C_{2-6}$ alkynyl, $C_{1-6}$ acyl, $C_{1-6}$ alkoxy, $C_{4-10}$ cycloalkyloxy, halo, $C_{1-6}$ haloalkyl, $C_{1-6}$ haloalkoxy, hydroxy, $C_{1-6}$ alkylthio, sulfonamidyl, $C_{6-12}$ aryl, 5-14-membered heteroaryl, $C_{6-12}$ aryl-$C_{1-6}$ alkyl, 5-14-membered heteroaryl $C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alky-OR', 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein $R^5$ is optionally substituted with 1-4 $R^7$;
wherein at least two of $R^3$, $R^4$ and $R^5$ are not H;
each $R^6$ is independently H, $C_{1-3}$ alkyl, halo, hydroxy, or amino; and
each $R^7$ is independently H, $C_{1-6}$ alkyl, $C_{2-6}$ alkenyl, $C_{2-6}$ alkynyl, $C_{1-6}$ acyl, halo, $C_{1-6}$ haloalkyl, $C_{1-6}$ haloalkoxy, hydroxy, aryl, heteroaryl, aryl$C_{1-6}$ alkyl, heteroaryl$C_{1-6}$ alkyl, $C_{1-6}$ alkoxy, $C_{3-6}$ cycloalkyloxy, aryloxy, aryl-$C_{1-6}$ alkoxy, heteroaryloxy, amino, $C_{1-6}$ alkylamino, $C_{2-12}$ dialkylamino, —C(O)NR"R', —NR"C(O)R", nitro, or cyano; wherein each R" is independently H or $C_{1-4}$ alkyl.

In embodiments in the compound of the formula (VI) $R_1$ is $C_{2-6}$ hydroxyalkyl, for example 3-hydroxypropyl.

In embodiments in the compound of the formula (VI) $R_2$ is $C_{1-4}$ alkyl, for example methyl.

In embodiments in the compound of the formula (VI) $R_3$ and $R_5$ are each independently selected from H, $C_{1-4}$ alkyl, phenyl and phenyl substituted with halo, for example chloro.

In embodiments in the compound of the formula (VI) $R_4$ is H, $C_{1-4}$ alkyl, phenyl or phenyl substituted with halo or —OCF$_3$, for example $R_4$ is 3-chlorophenyl or 3-trifluoromethoxyphenyl.

In one embodiment in the compound of the formula (VI) $R_1$ is 3-hydroxypropyl; $R_2$ is methyl; $R_3$ is H, methyl or 3-chlorophenyl; $R_4$ is 3-chlorophenyl or 3-trifluoromethoxyphenyl; and $R_5$ is H, methyl, or 4-chlorobenzyl.

The compound of formula (VI) may be a compound disclosed in claim 12 of WO 2016/023831 selected from:

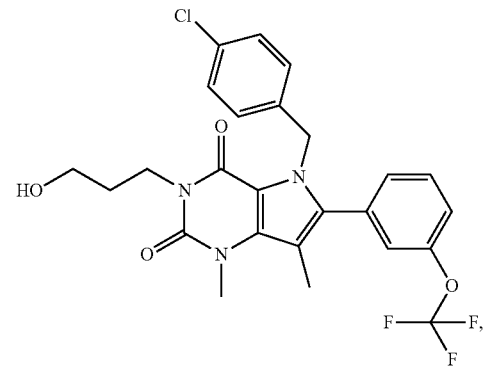

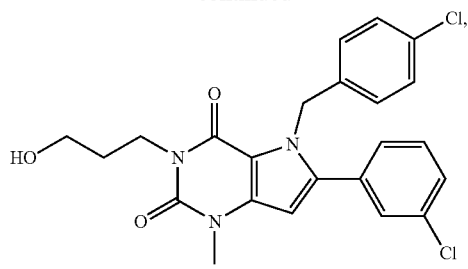
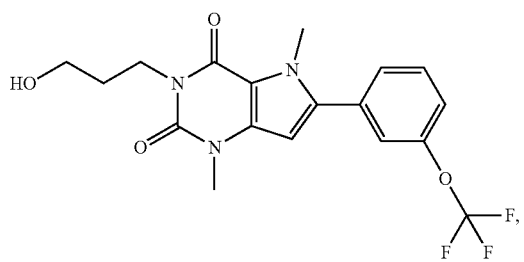
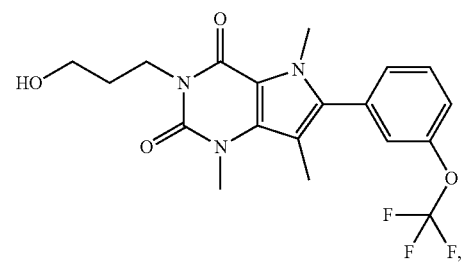
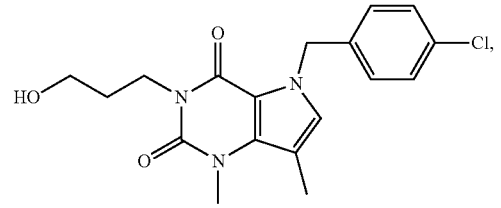
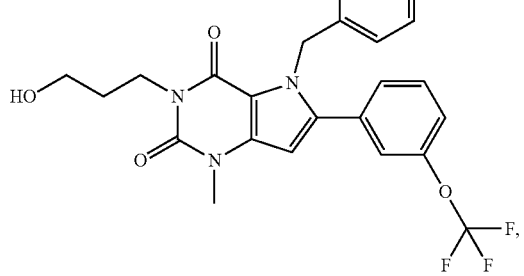
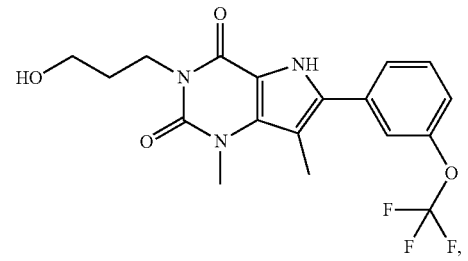

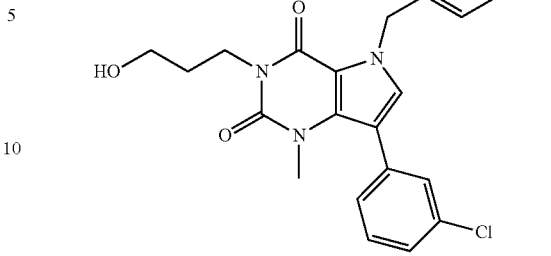

or a pharmaceutically acceptable salt thereof.

Compounds of formula (VI) may be prepared as described in WO 2016/023831.

In an embodiment the inhibitor is a compound of the formula (VII), or a pharmaceutically acceptable salt thereof:

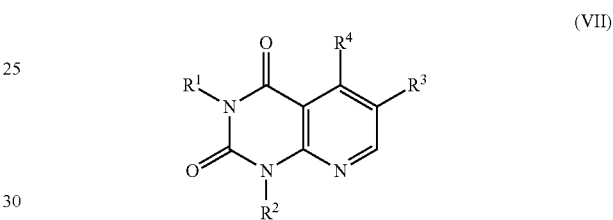

(VII)

wherein $R^1$ is $C_{2-10}$ hydroxyalkyl, optionally substituted with 1-3 $R^6$;

$R^2$ is H, $C_{1-6}$ alkyl, $C_{1-6}$ hydroxyalkyl, $C_{3-10}$ cycloalkyl, $C_{2-6}$ alkenyl, $C_{2-6}$ alkynyl, or $C_{1-6}$ alkoxy;

$R^3$ is $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-10}$ hydroxyalkyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$aryl, —$C_{6-12}$ aryl-$C_{1-6}$ alky-O, 5-14-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein $R^3$ optionally substituted with 1-5 $R^5$;

$R^4$ is $C_{1-6}$ alkyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alky-OR', 5-14-membered heteroaryl-$C_{1-6}$ alkyl, 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, or cyano, wherein each R' is independently H or $C_{1-6}$ alkyl and wherein $R^4$ is optionally substituted with 1-5 $R^5$;

each $R^5$ is independently $C_{1-6}$ alkyl, $C_{2-6}$ alkenyl, $C_{2-6}$ alkynyl, $C_{1-6}$ acyl, $C_{4-10}$ cycloalkyloxy, halo, $C_{1-6}$ haloalkyl, $C_{1-6}$ haloalkoxy, hydroxy, $C_{1-10}$ hydroxyalkyl, amino, $C_{6-12}$ aryl, 5-14-membered heteroaryl, $C_{6-12}$ aryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alkyl-OR', or 5-14-membered heteroaryloxy, wherein each R' is independently H or $C_{1-6}$ alkyl and wherein $R^5$ is optionally substituted with 1-5 $R^6$; and each $R^6$ is independently $C_{1-6}$ alkyl, $C_{1-6}$ alkoxy, $C_{3-10}$ cycloalkyl, halo, $C_{1-6}$ haloalkyl, $C_{1-6}$ haloalkoxy, hydroxyl, amino, $C_{1-6}$ alkylamino, $C_{2-12}$ dialkylamino, cyano, nitro, —C(O)NR'R', —NR'C(O)R', —C(O)OR', —C(O)R', acyl, nitro, or cyano, wherein each R' is independently H or $C_{1-6}$-alkyl.

In embodiments in the compound of the formula (VII) $R_1$ is $C_{2-6}$ hydroxyalkyl, for example 3-hydroxypropyl.

In embodiments in the compound of the formula (VII) $R_2$ is $C_{1-4}$ alkyl, for example methyl.

In embodiments in the compound of the formula (VII) $R_3$ is $C_{1-4}$ alkyl, $C_{1-4}$ alkoxy, phenyl-$C_{1-4}$ alkoxy-, 5-6 membered heteroaryl-$C_{1-4}$ alkyl-, phenyl-$C_{1-4}$ alkyl-, 5-6 membered heteroaryl-$C_{1-4}$ alkyl-, phenoxy-, 5-6 membered heteroaryloxy-, phenyl or 5-6 membered heteroaryl, wherein any phenyl or heteroaryl group in $R_3$ is optionally substituted by one or more substituents selected from halo, $C_{1-4}$ alkyl, $C_{1-4}$ alkoxy $C_{1-4}$ haloalkyl or $C_{1-4}$ haloalkoxy.

In embodiments in the compound of the formula (VII) $R_4$ is $C_{1-6}$ alkyl, 5-6 membered heteroaryl-$C_{1-6}$ alkyl-, phenyl-$C_{1-6}$ alkyl- or 5-6 membered heteroaryl-$C_{1-6}$ alkyl-, wherein any phenyl or heteroaryl group in $R_4$ is optionally substituted by one or more substituents selected from halo, $C_{1-4}$ alkyl, $C_{1-4}$ alkoxy $C_{1-4}$ haloalkyl or $C_{1-4}$ haloalkoxy.

The compound of formula (VII) may be a compound disclosed in claim 13 of WO 2016/023830 selected from:

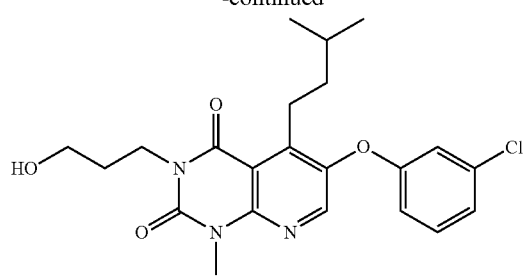

,

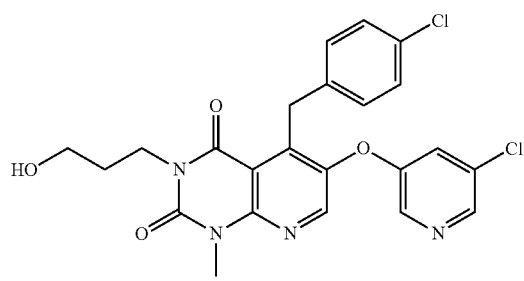

,

-continued

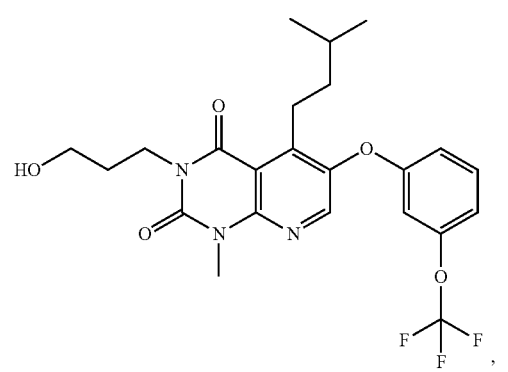

,

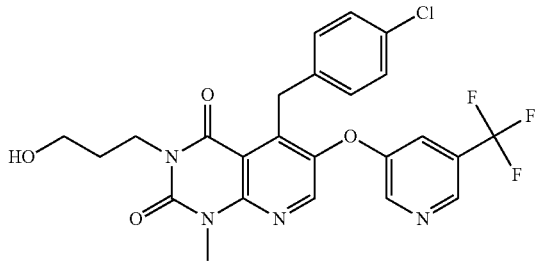

,

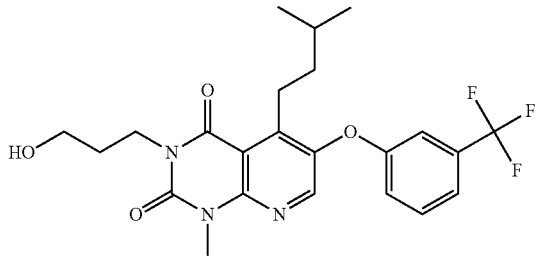

,

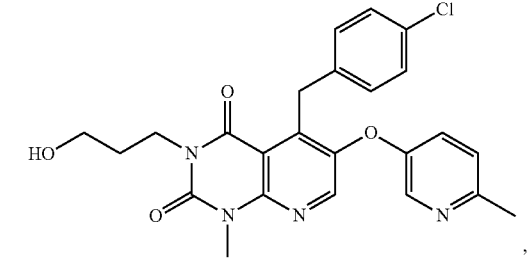

,

31
-continued
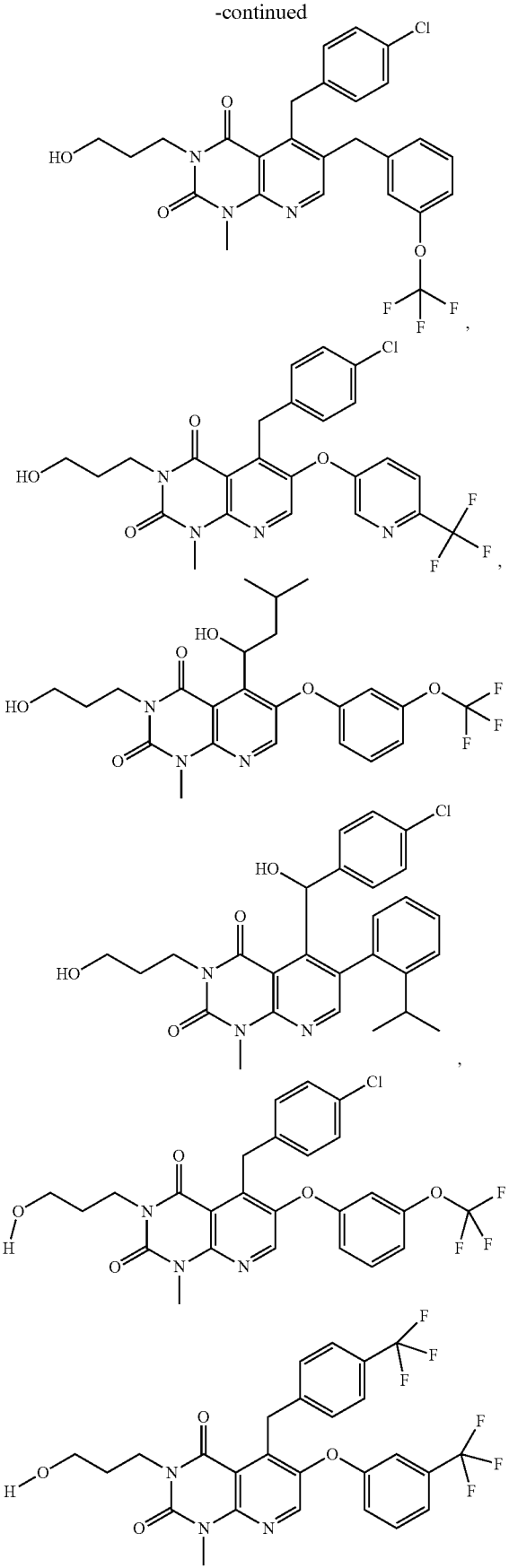
32
-continued
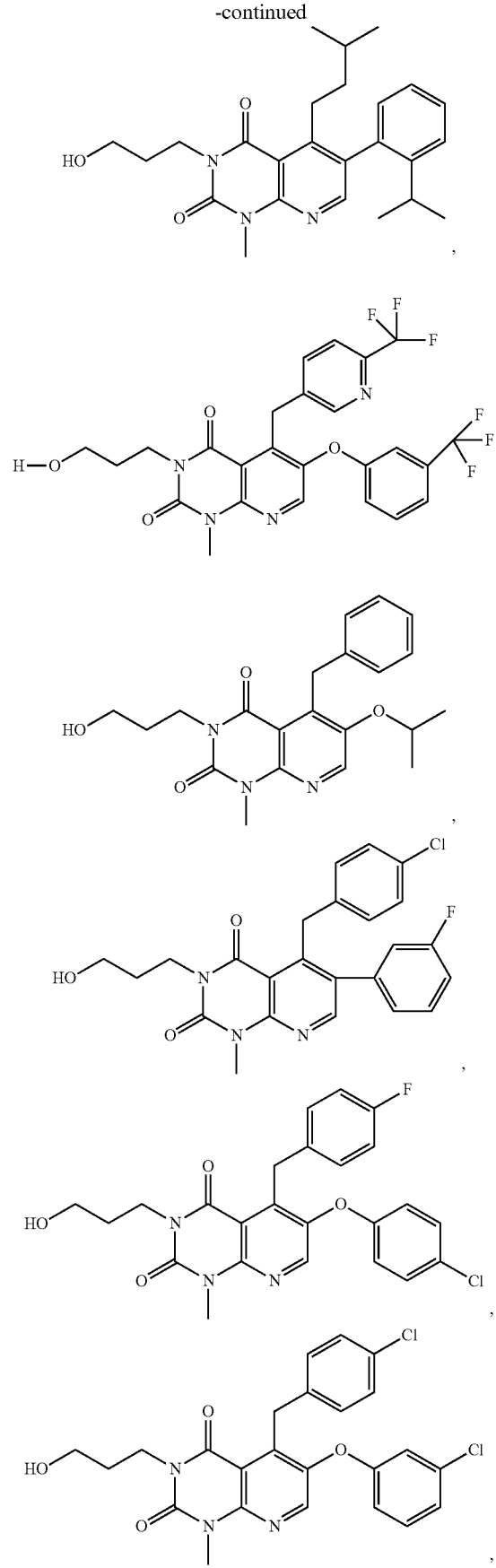

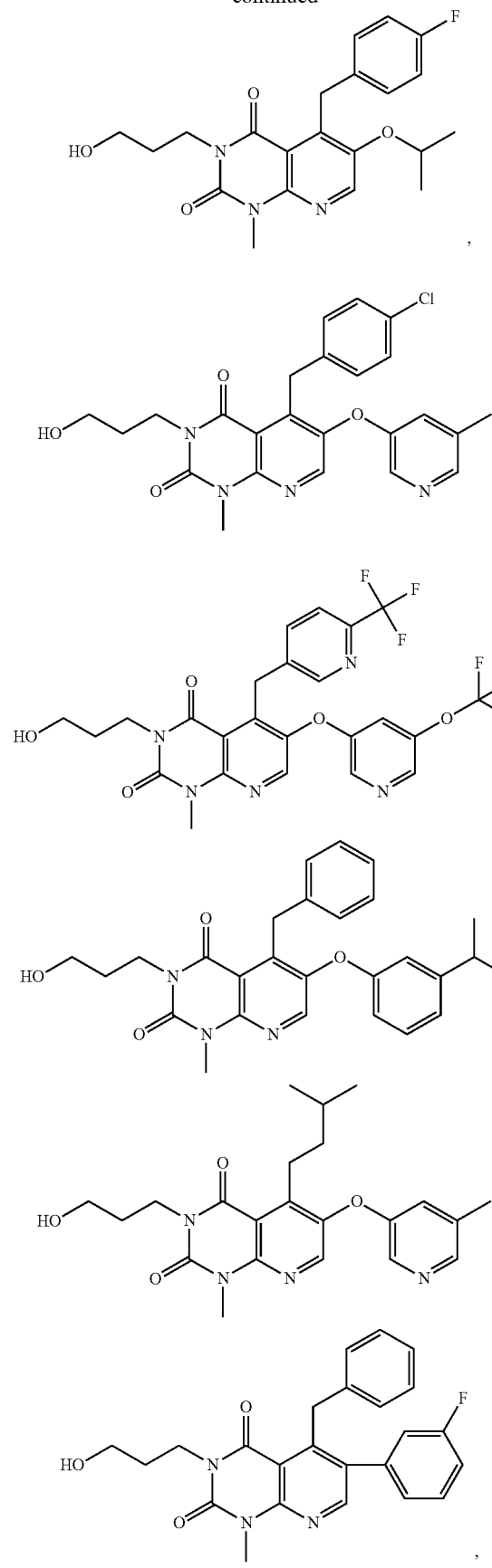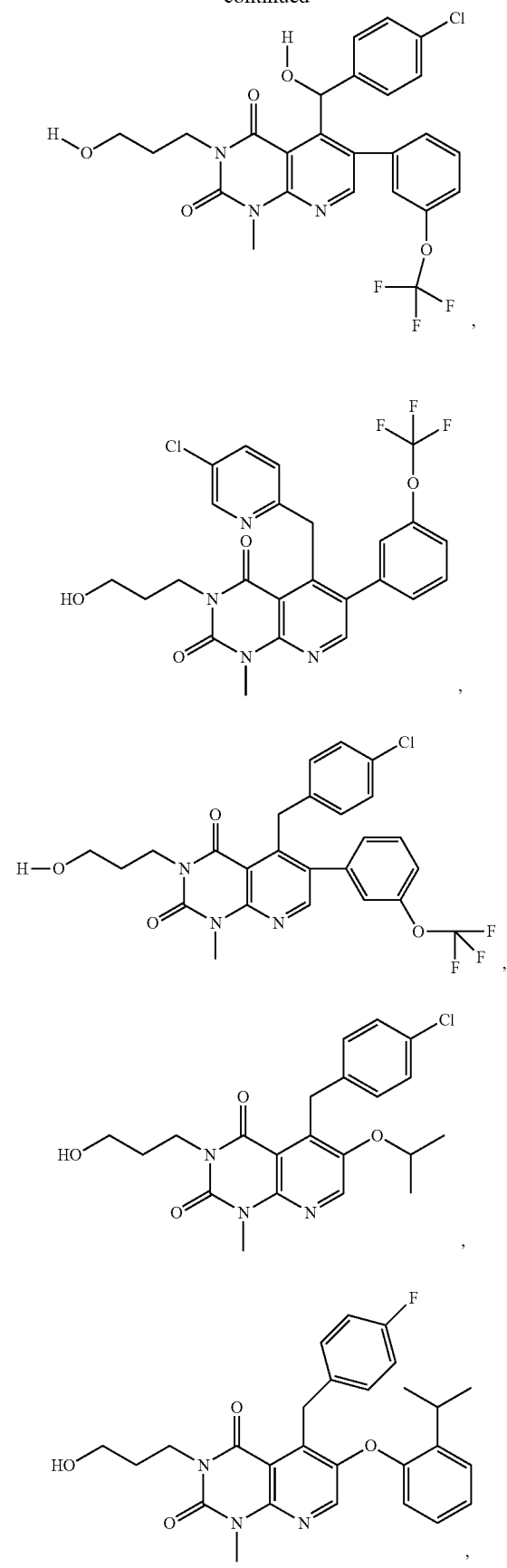

-continued

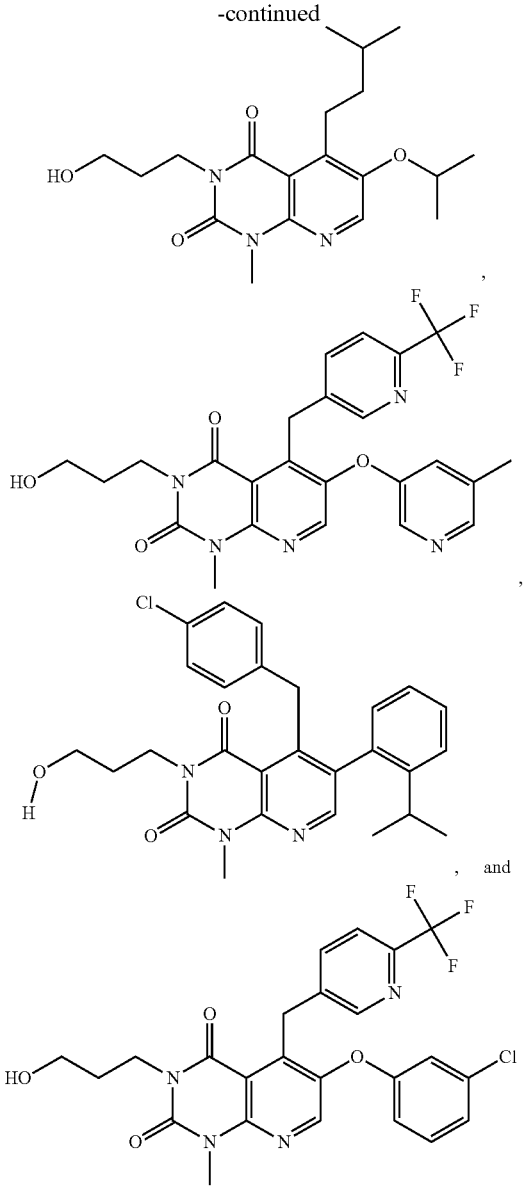

or a pharmaceutically acceptable salt thereof.

The compounds of formula (VII) may be prepared as described in WO 2016/023830.

The inhibitor may be a compound of the formula (VIII) or a pharmaceutically acceptable salt thereof:

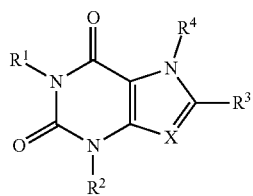

wherein
X is S or O;
$R^1$ is $C_{2-10}$ hydroxyalkyl, optionally substituted with 1-3 $R^5$;

$R^2$ is H, $C_{1-6}$ alkyl, $C_{1-6}$ hydroxyalkyl, $C_{3-10}$ cycloalkyl, $C_{2-6}$ alkenyl, $C_{2-6}$ alkynyl, or $C_{1-6}$ alkoxy;

$R^3$ is $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alky-OR', 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, cyano, wherein each R' is independently H or $C_{1-6}$ alkyl and wherein $R^3$ is optionally substituted with 1-4 $R^5$;

$R^4$ is $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alky-OR', 5-14-membered heteroaryl-$C_{1-6}$ alkyl, 5-14-membered heteroaryloxy, 3-18-membered heterocycloalkyl, amino, $C_{1-6}$ alkylamino, $C_{2-12}$ dialkylamino, —C(O)NR'R', —NR'C(O)R', urea, sulfonylurea, nitro, cyano, wherein each R' is independently H or $C_{1-6}$ alkyl and wherein $R^4$ is optionally substituted with 1-4 $R^5$ each $R^5$ is independently $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ alkylthio, thionyl, sulfonyl, sulfonamidyl, amino, $C_{1-6}$ alkylamino, $C_{2-12}$ dialkylamino, —C(O)NR'R', —NR'C(O)R', urea, sulfonylurea, nitro, cyano, wherein each R' is independently H or $C_{1-6}$ alkyl and $R^5$ is optionally substituted with 1-5 $R^6$; and each $R^6$ is independently $C_{1-6}$ alkyl, $C_{2-6}$ alkenyl, $C_{2-6}$ alkynyl, $C_{1-6}$ acyl, $C_{1-6}$ alkoxy, halo, $C_{1-6}$ haloalkyl, $C_{1-6}$ haloalkoxy, hydroxyl, amino, —C(O)NR'R', —NR'C(O)R', —C(O)R', nitro or cyano.

In embodiments in the compound of the formula (VIII) $R_1$ is $C_{2-6}$ hydroxyalkyl, for example 3-hydroxypropyl.

In embodiments in the compound of the formula (VIII) $R_2$ is $C_{1-4}$ hydroxyalkyl or $C_{1-4}$ alkyl, for example methyl, ethyl or 3-hydroxypropyl.

In embodiments in the compound of the formula (VIII) $R_3$ is $C_{1-4}$ alkyl, $C_{1-4}$ alkoxy, aryl-$C_{1-4}$ alkoxy-, 5-6 membered heteroaryl-$C_{1-4}$ alkyl-, aryl-$C_{1-4}$ alkyl-, 5-6 membered heteroaryl-$C_{1-4}$ alkyl-, aryloxy-, 5-6 membered heteroaryloxy-, aryl or 5-6 membered heteroaryl, wherein any aryl or heteroaryl group in $R_3$ is optionally substituted by one or more substituents selected from halo, $C_{1-4}$ alkyl, $C_{1-4}$ alkoxy $C_{1-4}$ haloalkyl, $C_{1-4}$ haloalkoxy or phenyl. Suitably in this embodiment aryl is phenyl or naphthyl, preferably phenyl. For example $R_3$ is phenyl or 5-6 membered heteroaryl, optionally substituted by one or more substituents selected from halo, $C_{1-4}$ alkyl, $C_{1-4}$ alkoxy $C_{1-4}$ haloalkyl and $C_{1-4}$ haloalkoxy.

In embodiments in the compound of the formula (VIII) $R_4$ is $C_{1-6}$ alkyl, $C_{1-6}$ acyl or benzyl, wherein $R_4$ is optionally substituted by one or more substituents selected from halo, $C_{1-4}$ alkyl or OR", wherein R" is H or methyl. For example $R_4$ is methyl, In one embodiment in the compound of the formula (VIII) X is S.

In one embodiment in the compound of the formula (VIII) X is O.

In one embodiment in the compound of the formula (VIII) X is O or S; $R_1$ is 3-hydroxypropyl; $R_2$ methyl or 3-hydroxypropyl; $R_3$ is phenyl, naphthyl, pyridyl, phenoxy or pyridyloxy optionally substituted by one or wo substituents selected from halo, —$CF_3$, or —$OCF_3$; and $R_4$ is $C_{1-6}$ alkyl, $C_{1-6}$ acyl or benzyl, wherein $R_4$ is optionally substituted by one or more substituents selected from halo or hydroxyl.

The inhibitor may be a compound of the formula (IX) or a pharmaceutically acceptable salt thereof:

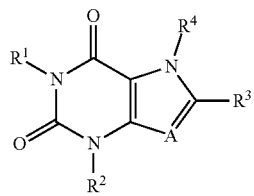

Formula (IX)

wherein:

A is S or O;

$R^1$ is $C_{2-10}$ hydroxyalkyl, optionally substituted with 1-3 $R^5$;

$R^2$ is H, $C_{1-6}$ alkyl, $C_{1-6}$ hydroxyalkyl, $C_{3-10}$ cycloalkyl, $C_{2-6}$ alkenyl, $C_{2-6}$ alkynyl, or $C_{1-6}$ alkoxy;

$R^3$ is $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alky-OH', 5-14-membered heteroaryloxy, 3-18-membered heterocycloalkyl, amino, $C_{1-6}$ alkylamino, $C_{2-12}$ dialkylamino, —C(O)NH—, —C(O)N—$C_{1-6}$ alkyl-, —NHC(O)—, —N—$C_{1-6}$ alkyl C(O)—, urea, sulfonylurea, nitro, cyano, and wherein $R^3$ is optionally substituted with 1-4 $R^5$;

$R^4$ is $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ alkylthio, thionyl, sulfonyl, sulfonamidyl, $C_{6-12}$ aryl, 5-14-membered heteroaryl, $C_{6-12}$ aryl-$C_{1-6}$ alkyl, 5-14-membered heteroaryl-$C_{1-6}$ alkyl, $C_{6-12}$ aryloxy, —O—$C_{6-12}$ aryl-$C_{1-6}$ alkyl, —O—$C_{1-6}$ alkyl-$C_{6-12}$ aryl, —$C_{6-12}$ aryl-$C_{1-6}$ alky-OH, 5-14-membered heteroaryl-$C_{1-6}$ alkyl, 5-14-membered heteroaryloxy, 3-18-membered heterocycloalkyl, amino, $C_{1-6}$ alkylamino, $C_{2-12}$ dialkylamino, —C(O)NH—, —C(O)N—$C_{1-6}$ alkyl-, —NHC(O)—, —N—$C_{1-6}$ alkyl C(O)—, urea, sulfonylurea, nitro, cyano, and wherein $R^4$ is optionally substituted with 1-4 $R^5$ each $R^5$ is independently $C_{1-6}$ alkyl, $C_{2-6}$ alkenyl, $C_{2-6}$ alkynyl, $C_{1-6}$ acyl, $C_{3-10}$ cycloalkyl, $C_{1-6}$ alkoxy, $C_{4-10}$ cycloalkyloxy, halo, $C_{1-6}$ haloalkyl, $C_{1-6}$ haloalkoxy, hydroxyl, $C_{1-6}$ alkylthio, thionyl, sulfonyl, sulfonamidyl, amino, $C_{1-6}$ alkylamino, $C_{2-12}$ dialkylamino, keto, C(O)NH—, —C(O)N—$C_{1-6}$ alkyl-, —NHC(O)—, —N—$C_{1-6}$ alkyl C(O)—, urea, sulfonylurea, nitro, cyano, wherein each R' is independently H or $C_{1-6}$ alkyl and $R^5$ is optionally substituted with 1-5 $R^6$; and each $R^6$ is independently $C_{1-6}$ alkyl, $C_{2-6}$ alkenyl, $C_{2-6}$ alkynyl, $C_{1-6}$ acyl, $C_{1-6}$ alkoxy, halo, $C_{1-6}$ haloalkyl, $C_{1-6}$ haloalkoxy, hydroxyl, amino, —C(O)NH—, —C(O)N—$C_{1-6}$ alkyl-, —NHC(O)—, —N—$C_{1-6}$ alkyl C(O)—, nitro or cyano.

The compounds of formula (IX) may be prepared as described in WO 2016/023832. WO 2016/023832 is hereby incorporated by reference, including any of the embodiments disclosed therein.

In one embodiment in the compound of the formula (IX) may be a compound disclosed in WO 2016/023832 selected from:

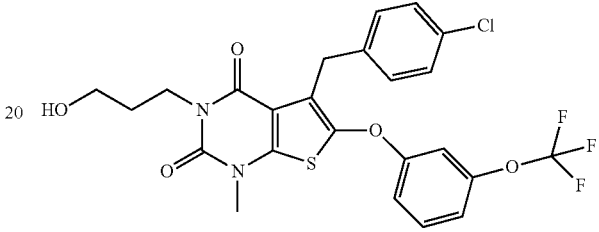

,

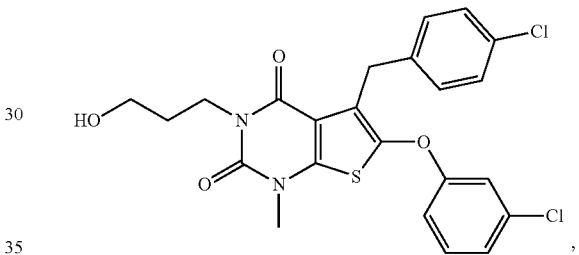

,

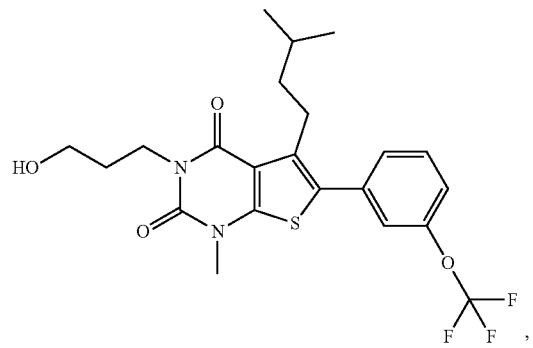

,

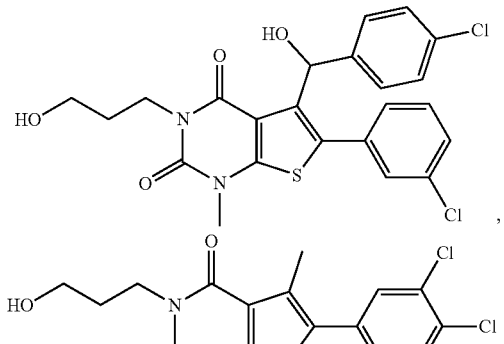

,

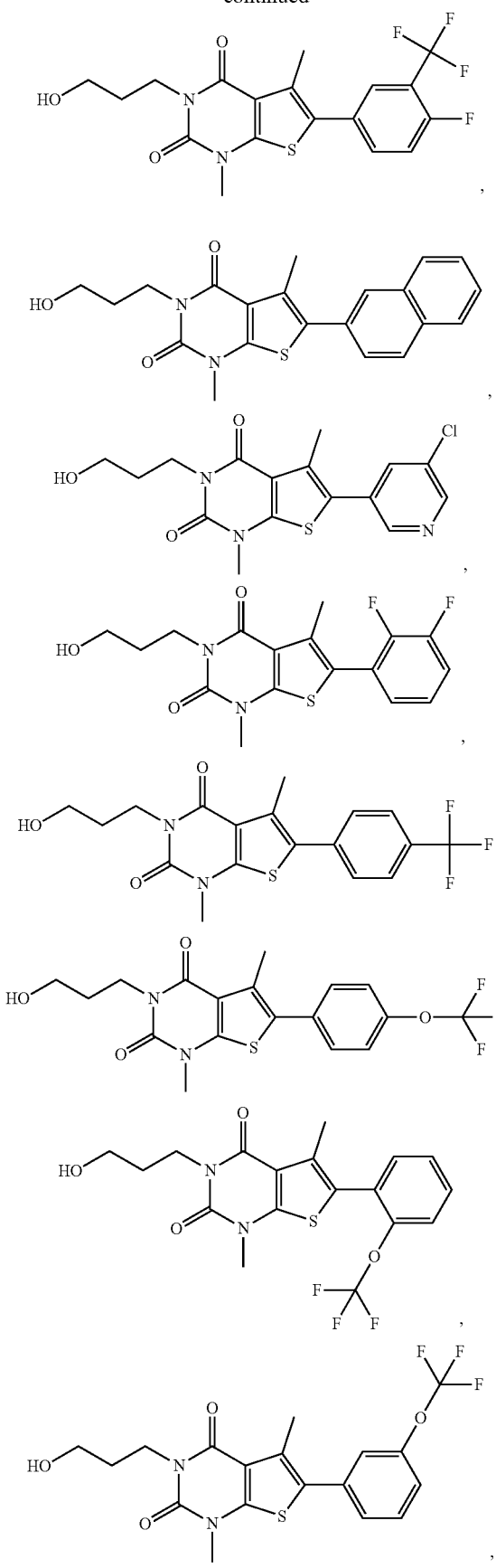
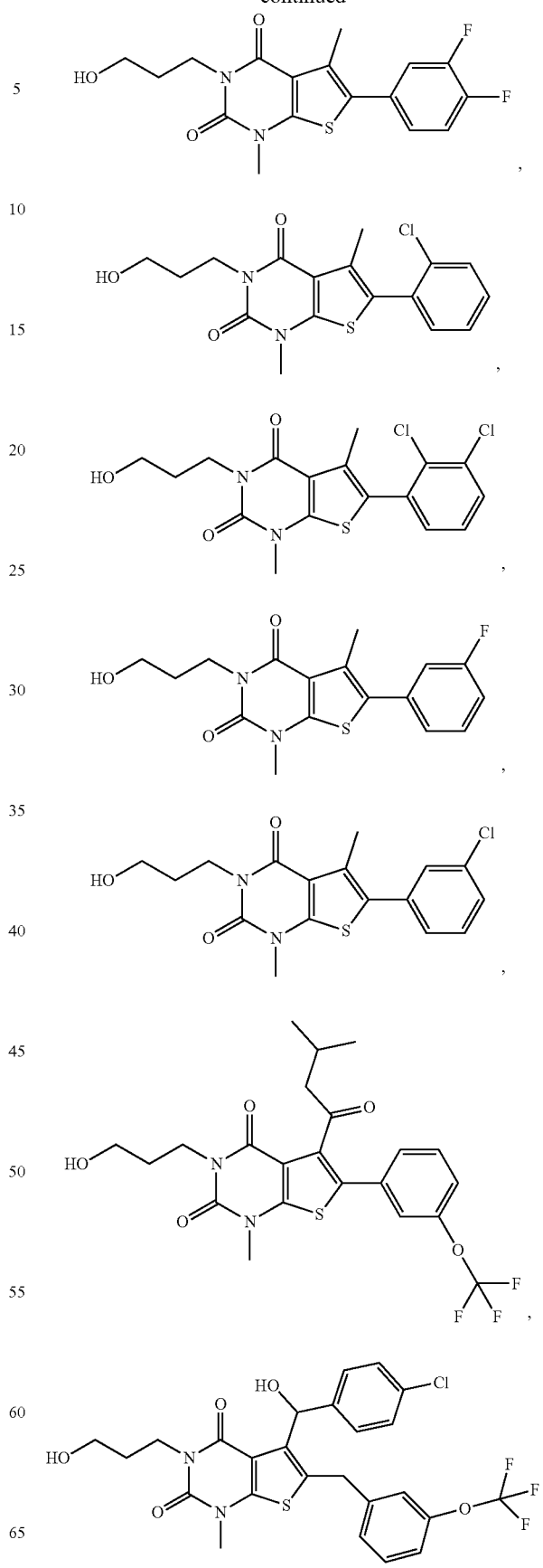

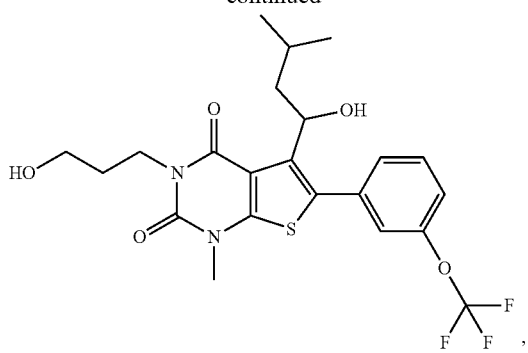

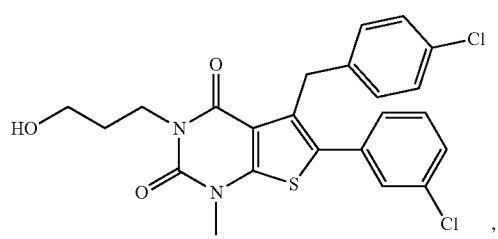

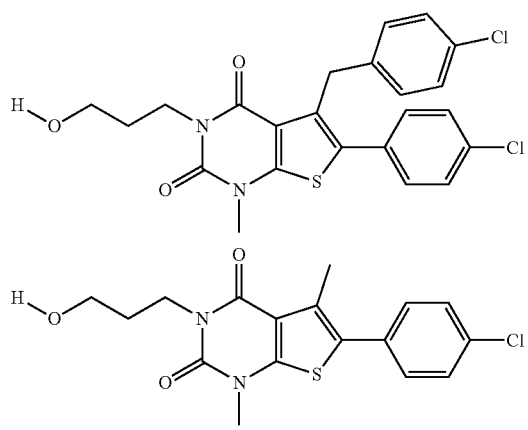

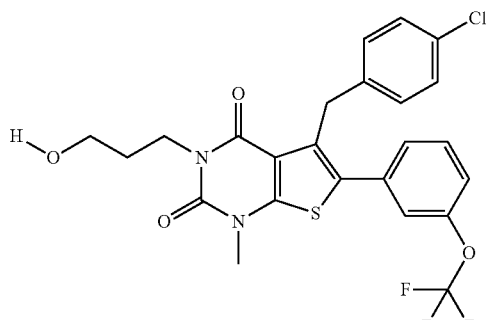

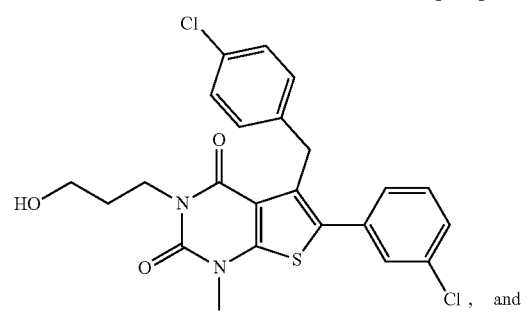

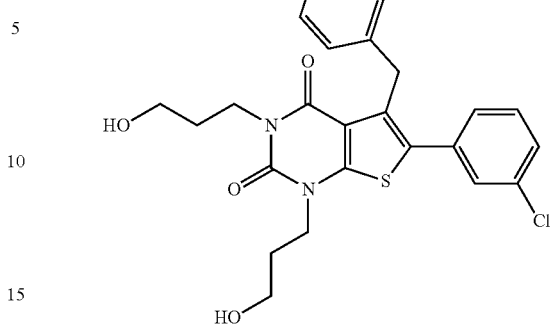

or a pharmaceutically acceptable salt thereof.

Compounds of the Formula (IX) may be prepared as disclosed in WO 2016/023832.

Clemizole is a potent and selective inhibitor of TRPC5 (Mol Pharmacol. 2014 November; 86(5):514-21). In an embodiment the inhibitor is clemizole or a derivative thereof. In one embodiment the inhibitor is a compound of the formula (X), or a pharmaceutically acceptable salt thereof:

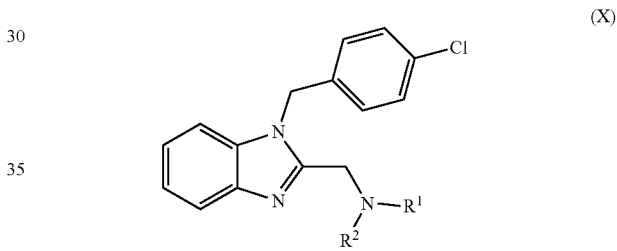

(X)

wherein $R^1$ and $R^2$ are independently H or $C_{1-4}$ alkyl, or $R^1$ and $R^2$ together with the nitrogen to which they are attached form a 4 to 6 membered heterocyclyl.

$R^1$ and $R^2$ may be methyl, ethyl, propyl or isopropyl.

In an embodiment $R^1$ and $R^2$ together with the nitrogen to which they are attached form pyrrolidinyl, piperidinyl, piperazinyl or morpholinyl.

In one particular embodiment inhibitor is clemizole, or a pharmaceutically acceptable salt thereof:

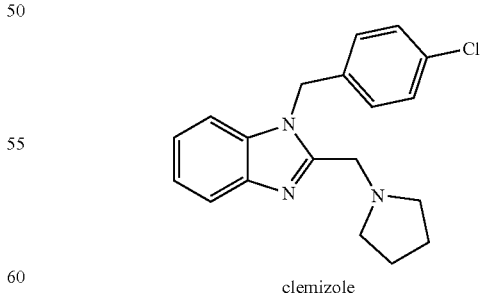

clemizole

Certain compounds of the formula (IX) are novel and form a further aspect of the invention. Accordingly there is provided the compound of the formula (IX), or a pharmaceutically acceptable salt thereof, wherein $R^1$ and $R^2$ are independently H or $C_{1-4}$ alkyl. Particular compounds of the formula (IX) include those wherein $R^1$ and $R^2$ are both $C_{1-4}$ alkyl, for example $R^1$ and $R^2$ are both independently selected from methyl, ethyl, propyl or isopropyl. A particular novel compound of the invention is a compound of the formula (IXa):

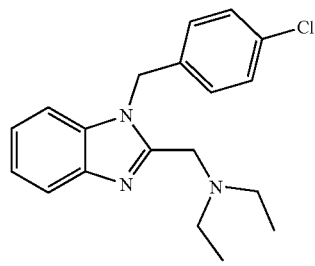

(Xa)

or a pharmaceutically acceptable salt thereof.

The inventors have found the compound of the formula (Xa) (also described herein as DE2) is a potent inhibitor of TRPC4 and TRPC5. Accordingly, in embodiments the inhibitor is a compound of the formula (Xa), or a pharmaceutically acceptable salt thereof.

In embodiments the inhibitor is AC1903 or a pharmaceutically acceptable salt thereof, as disclosed in "A small-molecule inhibitor of TRPC5 ion channels suppresses progressive kidney disease in animal models", Zhou et al, Science 358, 13321336.

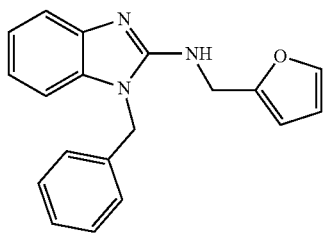

AC1903

In another embodiment the inhibitor is not a compound disclosed in Bon et al., British Journal of Pharmacology (2013) 170 459-474. In a further embodiment the inhibitor is not a natural product, for example inhibitors found in foods, such as fatty acids. In certain embodiments the inhibitor is not one or more of the following:
- a fatty acid, particularly the inhibitor is not an omega-3 fatty acid such as α-linolenic acid, eicosapentaenoic acid, or docosahexaenoic acid;
- a polyphenol, for example gallic acid, resveratrol or diethylstillbestrol;
- galangin (a natural product obtained from ginger);
- a flavonoid (particularly a flavonoid described in Naylor, J. et al (2016), Natural and synthetic flavonoid modulation of TRPC5 channels. British Journal of Pharmacology 173, 562-74); or
- an antioxidant (for example vitamin C and particularly the anti-oxidants disclosed in Naylor, J. et al (2011), TRPC5 channel sensitivities to antioxidants and hydroxylated stilbenes, Journal of Biological Chemistry 286, 5078-5086).

Suitably the inhibitor is a small molecule inhibitor of TRPC4 or TRPC5 which inhibits $Ca^{2+}$ ion influx in the Intracellular $Ca^{2+}$ assay described in the Examples at a concentration of 10 µM or less. Suitable the inhibitor is one which inhibits $Ca^{2+}$ ion influx in this assay at a concentration of 5 µM or less and preferably at a concentration of 1 µM or less.

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A "subject" or "patient" refers to a living organism suffering from or prone to a disease or condition that can be treated by administration of an inhibitor, as provided herein. Non-limiting examples include humans, other mammals, bovines, rats, mice, dogs, cats, monkeys, goat, sheep, cows, deer, horses and other non-mammalian animals. Preferably the patient or subject is human.

The term "halo" or "halogen" refers to one of the halogens, group 17 of the periodic table. In particular the term refers to fluorine, chlorine, bromine and iodine. Preferably, the term refers to fluorine or chlorine.

The term $C_{m-n}$ refers to a group with m to n carbon atoms.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_{1-4}$ alkyl" similarly refers to such groups containing up to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_1$-$C_4$ alkoxy. Other substituents for the alkyl group may alternatively be used.

The term "$C_{1-6}$ haloalkyl", e.g. "$C_{1-4}$ haloalkyl", refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{1-6}$ alkoxy" includes a branched or linear $C_{1-6}$ alkyl-O— having 1, 2, 3, 4, 5 or 6 carbon atoms. For example, $C_{1-6}$ alkoxy may be methoxy, ethoxy, propyloxy, isopropyloxy, butyloxy, isobutyloxy, tert-butyloxy, pentyloxy, or hexyloxy, and the like.

The term "haloalkoxy" includes a $C_{1-6}$ alkoxy substituted with at least one halogen atom independently chosen at each occurrence, for example fluorine, chlorine, bromine and iodine. The halogen atom may be present at any position on the $C_{1-6}$ alkoxy. For example the haloalkoxy may be chloromethoxy, fluoromethoxy, trifluoromethoxy or chloroethoxy.

The term "$C_{3-6}$ cycloalkyl" includes a saturated hydrocarbon ring system containing 3, 4, 5 or 6 carbon atoms. For example, the "$C_3$-$C_6$ cycloalkyl" may be cyclopropyl, cyclobutyl, cyclopentyl, cyclohexyl, bicycle[2.1.1]hexane or bicycle[1.1.1]pentane.

The term "amide" or "amido" includes —C(O)NR'R', wherein R' are independently H or $C_{1-6}$ alkyl.

The term "acyl" includes —C(O)R', wherein R' is H or $C_{1-6}$ alkyl.

The term "alkyl-amino" includes $C_{1-6}$ alkyl-amino (i.e. $C_{1-6}$ alkyl-NH), for example methylamino or ethylamino.

The term "dialkylamino" includes ($C_{1-6}$ alkyl)$_2$N—, for example dimethylamino, diethylamino or N-methyl, N-ethylamino.

The term "hydroxyl-alkyl" includes HO—$C_{1-6}$ alkyl-, for example HO—$C_{2-6}$ alkyl-. For example the hydroxyalkyl may be hydroxymethyl, hydroxyethyl or 2-hydroxybutyl.

The term "urea" includes —NR'C(O)NR'R', wherein R' is H or $C_{1-6}$ alkyl.

The term "thionyl" includes —S(O)R', wherein R' is H or $C_{1-6}$ alkyl.

The term "sulfonyl" includes —S(O)$_2$R', wherein R' is H or $C_{1-6}$ alkyl.

The term "sulfonylurea" includes —S(O)$_2$NR'C(O) NR'R', wherein R' is H or $C_{1-6}$ alkyl.

The term "sulfonamidyl" includes —S(O)$_2$NR'R', wherein R' is H or $C_{1-6}$ alkyl.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "aryl-$C_{m-n}$ alkyl-" includes an aryl group covalently attached to a $C_{m-n}$ alkylene group, both of which are defined herein. Examples of aralkyl groups include benzyl.

The term "aryloxy-" includes an aryl group covalently attached to —O—. Examples of aryloxy groups include phenoxy.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of heteroaryl include pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzo furyl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl or indolinyl.

"Heteroaryl-$C_{m-n}$ alkyl-" includes a heteroaryl group covalently attached to a $C_{m-n}$ alkylene group, both of which are defined herein. Examples of heteroaralkyl groups include pyridin-3-ylmethyl and the like.

The term "heteroaryloxy-" includes a heteroaryl group covalently attached to —O—. Examples of heteroaryloxy groups include pyridyloxy.

The term "heterocyclyl", "heterocycloakyl" "heterocyclic" or "heterocycle" includes a non-aromatic saturated or partially saturated monocyclic or fused, bridged, or spiro bicyclic heterocyclic ring system(s). Monocyclic heterocyclic rings may contain from about 3 to 12 (suitably from 3 to 7) ring atoms, with from 1 to 5 (suitably 1, 2 or 3) heteroatoms selected from nitrogen, oxygen or sulfur in the ring. Examples include Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazohdinyl, quinuclidinyl, thiazolidinyl, tetrahydrofuryl, trithianyl, tetrahydropyranyl, thiomorpholinyl, 1-oxothiomorpholinyl or 1,1-dioxothiomorpholinyl.

The term "Heterocyclyl-$C_{m-n}$ alkyl" includes a heterocyclyl group covalently attached to a $C_{m-n}$ alkylene group, both of which are defined herein.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

The invention contemplates pharmaceutically acceptable salts of compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:
   by reacting the compound of the invention with the desired acid or base;
   by removing an acid- or base-labile protecting group from a suitable precursor of the compound of the invention or by ring-opening a suitable cyclic precursor, for example, a lactone or lactam, using the desired acid or base; or
   by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%

The compounds described herein may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^{2}H$ (also written as "D" for deuterium), $^{3}H$ (also written as "T" for tritium), $^{11}C$, $^{13}C$, $^{14}C$, $^{15}O$, $^{17}O$, $^{18}O$, $^{18}F$ and the like. The radionuclide that is used will depend on the specific application of that radio-labelled derivative. For example, for in vitro competition assays, $^{3}H$ or $^{14}C$ are often useful. For radio-imaging applications, $^{11}C$ or $^{18}F$ are often useful. In some embodiments, the radionuclide is $^{3}H$. In some embodiments, the radionuclide is $^{14}C$. In some embodiments, the radionuclide is $^{11}C$. And in some embodiments, the radionuclide is $^{18}F$.

It is also to be understood that certain compounds described herein may exist in solvated as well as unsolvated forms such as, for example, hydrated forms. It is to be understood that the invention encompasses all such solvated forms.

It is also to be understood that certain compounds described herein may exhibit polymorphism, and that the invention encompasses all such.

Compounds described herein may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Methods

Animals. Trpc4 gene-disrupted (knockout) mice on the C57BL/6J background (B6.129P2-Trpc4$^{tm1Dgen}$/H) were generated by Deltagen Inc. and supplied by the Medical Research Council Harwell, UK. The sequence spanning base 1272 to base 1330 of the Trpc4 gene was deleted and inserted with a Lac-Z neo cassette to create a detectable mutation in the mice. Trpc5 gene-disrupted (knockout) C57BL/6 mice were generated as part of the International Mouse Phenotyping Consortium (IMPC) based on Trpc5 gene-targeted ES cells originally created by the Knockout Mouse Project (KOMP) (Trpc5tm1b(KOMP)Wtsi) and provided by Riken BRC, Japan. Mice were intercrossed to generate wild-types and knockouts. Mice were weaned at 3 weeks of age and 2-5 mice were housed in the same cage with same-sex littermates under a 12 hr light/dark cycle. Only male mice were used in this study. Food pellets and water were provided ad libitum. All procedures were approved by the University of Leeds Animal Welfare and Ethical Review Body and were conducted under a moderate protocol on a project license issued by the competent authority of the United Kingdom.

Glucose and Insulin Tolerance Tests. For Glucose Tolerance Test (GTT) mice were fasted overnight for 16 hr following application of 1 g·kg$^{-1}$ D-glucose intraperitoneally. Blood glucose levels were then measured every 0, 30, 60, 90 and 120 min with a glucose meter. For Insulin Tolerance Test (ITT) mice were fasted for 2 hr followed by administration of 0.75 unit·kg$^{-1}$ insulin intraperitoneally. Blood glucose measurements were performed in the same manner as GTT.

Metabolic measurements Individual mice were housed in single metabolic cages where food powder and water were provided ad libitum. Mice were allowed to acclimatize to the cage conditions for 72 hr. Food and water are then replaced with exact amounts of each, followed by measurement of food and water intake and excretory output after 48 hr. Body temperatures were measured by an infrared thermometer.

Cell culture Mouse stromal vascular fraction (SVF) cells from subcutaneous adipose tissue were isolated by mincing of the tissue followed by enzymatic digestion with 0.3 mg·mL$^{-1}$ Collagenase type II (Sigma), 0.3 mg·mL$^{-1}$ Collagenase type IV (Sigma), 2 mg·mL$^{-1}$ BSA (Sigma), 0.08 mg·mL$^{-1}$ DNase I (Sigma) and 0.04 mg·mL$^{-1}$ Dispase (Thermo Fisher Scientific) in serum free RPMI 1640 media (Gibco) for 45 min at 37° C. in 95% $O_2$ and 5% $CO_2$ environment. Isolated cells were centrifuged and processed through a 100 μm cell strainer. Following centrifugation, the cell pellet was reconstituted in full RPMI 1640 media containing 15% fetal calf serum and 1% penicillin-streptomycin (Gibco). Media was changed on the following day to remove non-adherent cells. Adipocyte differentiation[32] was done at 100% cell confluence in full RPMI 1640 media containing 1 μM dexamethasone (Sigma), 0.5 mM isobitylmethylxanthine (Sigma), 20 μg·mL$^{-1}$ insulin (Sigma), 50 nM T3 (Sigma) and 5 μM troglitazone (Sigma) for 48 hr followed by incubation with full RPMI 1640 media containing 20 μg·mL$^{-1}$ insulin for 72 hr. Cells are then maintained in full RPMI 1640 media for another 2 days until maturation. HEK 293 cells stably expressing tetracycline-inducible TRPC4 and TRPC5 were maintained in DMEM+ GlutaMAX-1 (Thermo Fisher Scientific) containing 10% fetal calf serum, 1% penicillin/streptomycin, 400 μg·mL$^{-1}$ zeocin and 5 μg·mL$^{-1}$ blasticidin S at 37° C. in a 5% $CO_2$ incubator. Expression was induced by incubation with 1 μg·mL$^{-1}$ tetracycline 24 hr prior to experiments.

Immunohistochemistry Tissues were fixed in 4% paraformaldehyde, processed in paraffin and sectioned into 5 μm sections for staining. Standard Hematoxylin and Eosin and Sirius Red staining protocols were applied. For UCP1 staining in adipose tissue sections, enzymatic antigen retrieval was done using 0.1% (v/v) Trypsin, 0.1% (w/v) $CaCl_2$ in phosphate buffered saline (PBS), pH 7.8 (NaOH) in a 37° C. humidifier incubator for 1.5 hr. Following primary antibody incubation, signals were amplified using a biotin conjugated secondary antibody (Jackson ImmunoResearch) followed by streptavidin conjugated HRP (Abcam) incubation for 1 hr and 3,3'-diaminobenzidine tetrahydrochloride (DAB) (Thermo Fisher Scientific) incubation for 15 min. Images were collected using a standard light microscope. Fiji (ImageJ) (National Institute of Health) was used to calculate % of staining in IHC images.

Quantitative RT-PCR analysis RNA from cell and tissue samples was obtained using TRIzol reagent (Thermo Fisher Scientific). 1 μg RNA was reverse-transcribed using High-Capacity cDNA Reverse Transcription Kit (Applied Biosystems) and RT-PCR analysis was performed using SYBR Select Masters Mix (Thermo Fisher Scientific) and Light-Cycler® 480 (Roche Life Science). The primers used are tabulated in Supplementary Table 1[34]. Relative fold-change in expression was calculated using the comparative cycle method ($2^{-\Delta\Delta C_t}$) Mouse Gapdh gene was used as the reference.

Intracellular $Ca^{2+}$ measurement HEK 293 cells containing stable incorporation of inducible TRPC4 or TRPC5 expression were seeded into 96-well clear-bottomed poly-D-lysine-coated black plates (Corning Life Sciences) at 90% confluence 24 hr before the experiment. Cells were loaded with 2 μM Fura-2-AM in Standard Bath Solution (SBS) at 37° C. for 45 min in the presence of 0.01% pluronic acid (Sigma). SBS contained (in mM): 140 NaCl, 5 KCl, 1.2 $MgCl_2$, 1.5 $CaCl_2$, 8 Glucose and 10 HEPES, pH 7.4 (NaOH)[35]. Cells were washed three times with SBS prior to $Ca^{2+}$ measurements. In some wells cells were incubated with DE2 or C31 for 30 minutes prior to the recording. The Fura-2-AM fluorescence was recorded using a 96-well fluorescence plate reader FlexStation II (Molecular Devices) at excitation wavelengths of 340 nm and 380 nm, and the emitted light was collected at 510 nm. Measurements were made at room temperature (21±3° C.).

ELISA Mouse TNFα in mouse serum was measured in accordance with the manufacturer's guidelines (EMTNFA, Thermo Fisher Scientific).

Protein preparation and immunoblotting Proteins were isolated from cells and tissues using radio-immunoprecipitation assay (RIPA) buffer containing (in mM) 150 NaCl, 20 Tris HCl, 1 EGTA, 1 EDTA, 1% NP-40, 0.1% sodium dodecyl sulfate (SDS) and 1% sodium deoxylate. Complete™ protease inhibitor (Roche Life Science) was added into RIPA fresh before use in accordance with the manufacturer's instructions. Immunoblotting was carried out under standard protocols with primary antibodies anti-UCP1 (1:500, ab23841; Abcam), Cytochrome C (1:4000, ab110325; Abcam), Akt (pan) (1:1000, 4691; Cell Signaling) and Phospho-Akt (Ser473) (1:500, 4060; Cell Signaling). Anti-GAPDH (1:4000, AM4300; Ambion Life Technologies) was used as the loading control. Secondary antibodies anti-rabbit-HRP (1:3000, 711-035-152, Jackson ImmunoResearch) and anti-mouse-HRP (1:3000, 715-035-150, Jackson ImmunoResearch) were used. Chemiluminescence signals were visualized using SuperSignal® West Femto Maximum Sensitivity Substrate (Thermo Fisher Scientific). Respirometry scWAT was digested with the method stated in Cell culture. ~3,000 000 cells from the SVF and adipocyte fractions were pooled into individual cell culture dishes. Cells were incubated with either TRPC4/5 inhibitors DE2/C31 or vehicle DMSO in full RPMI 1640 for 24 hrs in a cell culture incubator. Prior to the experiment cells were harvested from culture dishes, centrifuged and reconstituted in mitochondrial respiration medium MiR05 containing (in mM): 0.5 EGTA, 3 $MgCl_2 \cdot 6H_2O$, 60 Lactobionic acid, 20 Taurine, 10 $KH_2PO_4$, 20 HEPES, 110 D-Sucrose, added with 1 g·L$^{-1}$ BSA. The cells were inoculated into the OROBOROS Oxygraph-2k chambers and oxidative phosphorylation analyses were performed using the mitochondrial substrate-uncoupler-inhibitor-titration protocol consisting of: substrate activation using sodium pyruvate, inhibition of ATP synthase using oligomycin, uncoupling via sequential addition of FCCP to maximum oxygen flux, mitochondria complex I and III inhibition using Rotenone and Antimycin A. Traces were analyzed using DatLab 6 Software (OROBOROS), measuring for routine state respiration (routine), mitochondrial leak (leak), maximum uncoupling capacity of the electron transport system (ETS) and rotenone and antimycin A-inhibited residual oxygen consumption (ROX).

Immunocytochemistry MitoTracker® Red FM (M22425, Thermo Fisher Scientific) was used according to manufacturer's instructions. Adipocytes were incubated with 400 nM MitoTracker® Red FM in full RPMI 1640 for 45 min. Cells were then washed 5 times with serum free RPMI 1640 and fixed in 4% PFA for 1 hr at room temperature. Following fixation, cells were permeabilized with 0.1% Triton-X100 in TBST containing (in mM) 150.6 NaCl, 12.4 Tris-base, 2.68 KCl and 0.2% Tween-20, pH 7.1-7.2 (HCl) and incubated with primary antibody UCP1 overnight at 4° C. UCP1 signal was amplified using a secondary antibody conjugated to AlexFluor-488 (Jackson ImmunoResearch). Cells were counterstained with DAPI (62248, Thermo Fisher Scientific) before mounting. For whole mount immunocytochemistry, adipose tissue was excised and fixed in 4% PFA overnight. Tissues were dehydrated with ascending concentrations of methanol in PBS and alternated between room temperature and −80° C. for antigen retrieval. Following rehydration with descending concentrations of methanol in TBST, tissues were incubated in TBST containing 0.1% Triton-X100 for 2 hr. Tissues were incubated in blocking solution overnight. Tissues were incubated in primary antibody to caveolin-1 (1:200, 611339, BD Transduction Laboratories™) and conjugated primary-secondary antibody F4/80:Pacific Blue® (1:2000, MCA497PBT, Bio-Rad) overnight. Caveolin-1 staining was amplified using AlexaFluor680® (1:200, cat no. 115-635-174, Jackson immunoresearch). Images were collected using a LSM880 with Airyscan (Zeiss).

Chemicals (−)-Englerin A (EA) powder (#82530, Phytolab) was reconstituted in DMSO and the stock solution was 10 mM. Compound 31 (C31) was synthesized as previously described in WO 2014/143799 and dissolved in DMSO. The stock solution was 5 mM. DE2 was synthesized as described below. The stock solution was 10 mM in DMSO. Sodium pyruvate (Sigma) was made fresh at 2 M in ddH$_2$O. FCCP (Sigma) was made at 1 mM in EtOH. Rotenone (Sigma) was made at 0.1 mM in EtOH. Oligomycin was made at 4 mg·ml$^{-1}$ in EtOH. Antimycin A was made at 5 mM in EtOH.

Synthesis of DE2: ({1-[(4-Chlorophenyl)methyl]-1H-benzimidazol-2-yl}methyl)diethylamine (1H-Benzimidazol-2-ylmethyl)diethylamine

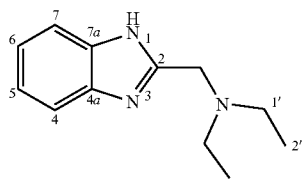

A mixture of diethylamine (220 mg, 3.00 mmol) and anhydrous potassium carbonate (210 mg, 1.50 mmol) in acetone (5 mL) was stirred for 5 minutes before the addition of 2-(chloromethyl)-1H-benzimidazole (250 mg, 1.50 mmol). The reaction mixture was stirred for 8 hr at room temperature and upon completion, the solvent was removed in vacuo. The crude product was extracted with EtOAc twice (10 mL×2) and the combined organic extracts were washed with brine (10 mL) and dried (MgSO$_4$). The solution was concentrated and purified using flash column by eluting with 0-25% MeOH in DCM. The selected fractions were evaporated to give a yellow solid (230 mg, 76%). R$_f$ 0.63 (2:3 MeOH:DCM). LC-MS m/z 204.0 (M+H)$^+$, RT 1.03 min; δ$_H$ (500 MHz, CD$_3$OD) 1.05 (6H, t, J=7.3 Hz, H2'), 2.57 (4H, quartet, J=7.3 Hz, H1'), 3.82 (2H, s, C$\underline{H}_2$), 5.36 (1H, br s, NH), 7.06-7.19 (2H, m, H5, H6), 7.53-7.56 (2H, m, H7, H4); δ$_C$ (125 MHz, CD$_3$OD) 12.1 (C$_2$'), 48.5 (C$_3$'), 52.0 (C$\underline{H}_2$), 115.7 (C7), 123.3 (C4), 139.6 (C4a), 154.6 (C2); FT-IR (cm$^{-1}$) 3046 (C—H, aromatic), 1273 (C—N, aromatic amine); HRMS (ESI): m/z calcd. for C$_{12}$H$_{18}$N$_3$ [M+H]$^+$ 204.1497. Found: 204.1495.

({1-[(4-Chlorophenyl)methyl]-1H-benzimidazol-2-yl}methyl)diethylamine

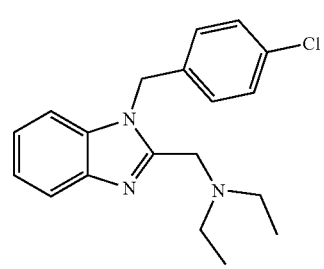

Under N$_2$ gas, (1H-benzimidazol-2-ylmethyl)diethylamine (430 mg, 2.0 mmol) was dissolved in anhydrous THF (5 mL), then cooled to 0° C. To this solution was added sodium hydride (60% suspension in mineral oil) (96 mg, 4.0 mmol) and the mixture stirred at 0° C. for 5 minutes. Then, 4-chlorobenzyl chloride (430 mg, 2.10 mmol) was added followed by the addition of tetrabutylammonium bromide (0.06% eq.). The mixture was stirred at room temperature overnight, then diluted with a solution of water (2 drops) in THF (5 mL). The mixture was filtered through Celite, washed with EtOAc (5 mL) and concentrated to dryness.

The crude was purified using flash column by eluting with a 0-100% EtOAc in Pet.Ether. The product fractions were combined and the solvent was evaporated to afford a yellow solid (470 mg, 69%). R$_f$ 0.39 (4:1 EtOAc:Pet. Ether). LC-MS m/z 328.0 (M+H)$^+$, RT 1.65 min; δ$_H$ (500 MHz, CDCl$_3$) 1.01 (6H, t, J=7.0 Hz, H2'), 2.60 (4H, quartet, J=7.0 Hz, H1'), 3.86 (2H, s, C$\underline{H}_2$-diethylamine), 5.63 (2H, s, C$\underline{H}_2$-4-chlorophenyl), 7.01 (2H, d, J=8.0 Hz, H2"), 7.19-7.31 (5H, m, H3", H7, H6, H5), 7.80 (1H, d, J=8.0 Hz, H4); δ$_C$ (125 MHz, CDCl$_3$) 11.3 (C2'), 46.5 (CH$_2$-diethylamine), 47.0 (C1'), 51.5 (C$\underline{H}_2$-4-chlorophenyl), 109.7 (C7), 119.8 (C4), 122.2 (C5), 122.9 (C6), 127.7 (C2"), 129.0 (C3"), 133.4 (C4"), 135.2 (C7a), 135.9 (C1"), 142.4 (C4a), 152.0 (C2); FT-IR (cm$^{-1}$) 3057 (C—H, aromatic), 1249 (C—N, aromatic amine); HRMS (ESI): m/z calcd. for C$_{19}$H$_{23}$ClN$_3$ [M+H]$^+$ 328.1584. Found: 328.1575; M.P 63-65° C.

Statistical analysis Data were analyzed using Origin software (version 9.1, OriginLab, Northampton, MA, USA). Paired 2-sample t-test and one-way ANOVA were used to perform tests of significance. n is the number of independent experiments. In experiments on intracellular Ca$^{2+}$ measurements, n refers to the number of individual 96-well plates used and N is the total number of wells measured. Statistical significance is indicated by numerical values on designated figures.

Results

Studies were performed on genetically-modified mice in which TRPC4 protein or TRPC5 protein was absent, designated as TRPC4 and TRPC5 knockout mice (C4$^{KO}$ and C5$^{KO}$).

Example 1: Normal Body Weight on Chow Diet

Body weight and Subcutaneous white adipose tissue (scWAT) fat pad weight were measured in C4WT (wildtype litter-mate controls for TRPC4 knockout mice), C5WT (wildtype litter-mate controls for TRPC5 knockout mice), C4KO (TRPC4 knockout mice) and C5KO (TRPC5 knockout mice) (n=6).

C4$^{KO}$ and C5$^{KO}$ mice on chow diet were apparently normal, showing no difference in body weight or fat pad weight compared with litter-mate control mice (FIG. 1).

Example 2: Inability to Gain Excess Total Body Weight on High Fat Diet

Figure 2:
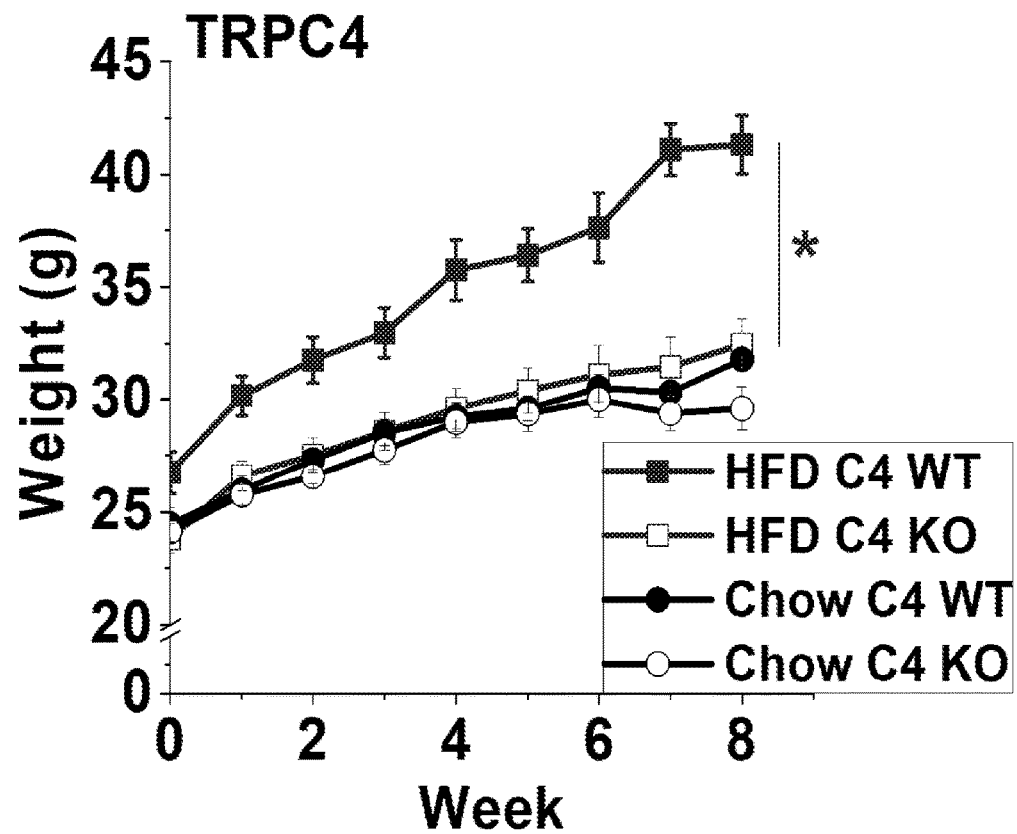
FIG. 2 demonstrates that TRPC4 knockout mice and TRPC5 knockout mice were unable to gain excess total body weight on high fat diet. Summary data for weights of mice during 8 weeks of diet feeding (mean±SEM, n=7-8). Diets were chow (Chow) or 60% high-fat (HFD). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.
Figure 2:
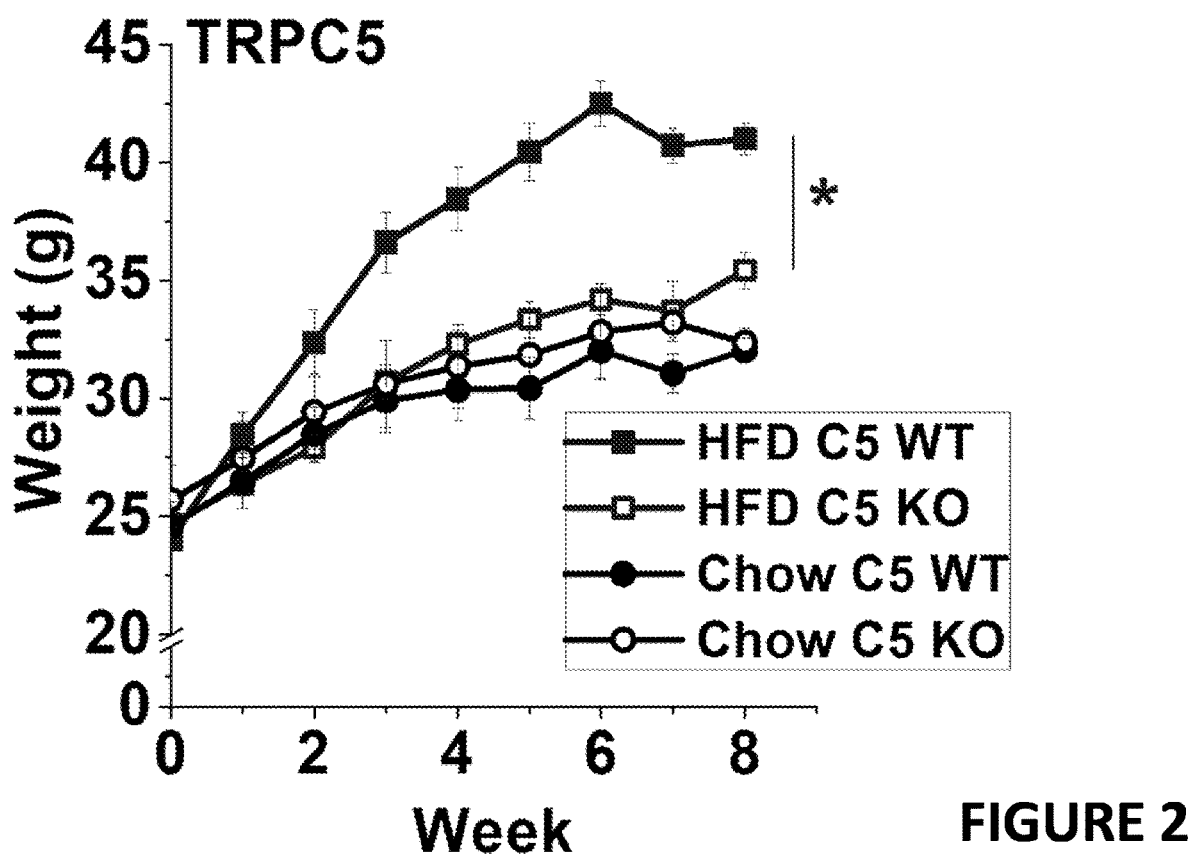

Mice were next studied on 60% high-fat diet (excess calorie intake). Bodyweights of mice (C4WT, C5WT, C4KO and C5KO) during 8 weeks of diet feeding were measured (n=7-8). Diets were chow (Chow) or 60% high-fat (HFD). Control wildtype (WT) litter-mates (C4$^{WT}$ and C5$^{WT}$) gained excess total weight as expected during the 8 week experiment period (FIG. 2). C4$^{KO}$ and C5$^{KO}$ mice were, by contrast, strikingly similar to mice on chow diet, showing only normal weight gain as the mice matured (FIG. 2).

Example 3: Inability to Gain Excess Fat Pad Weight on High Fat Diet

Figure 3:
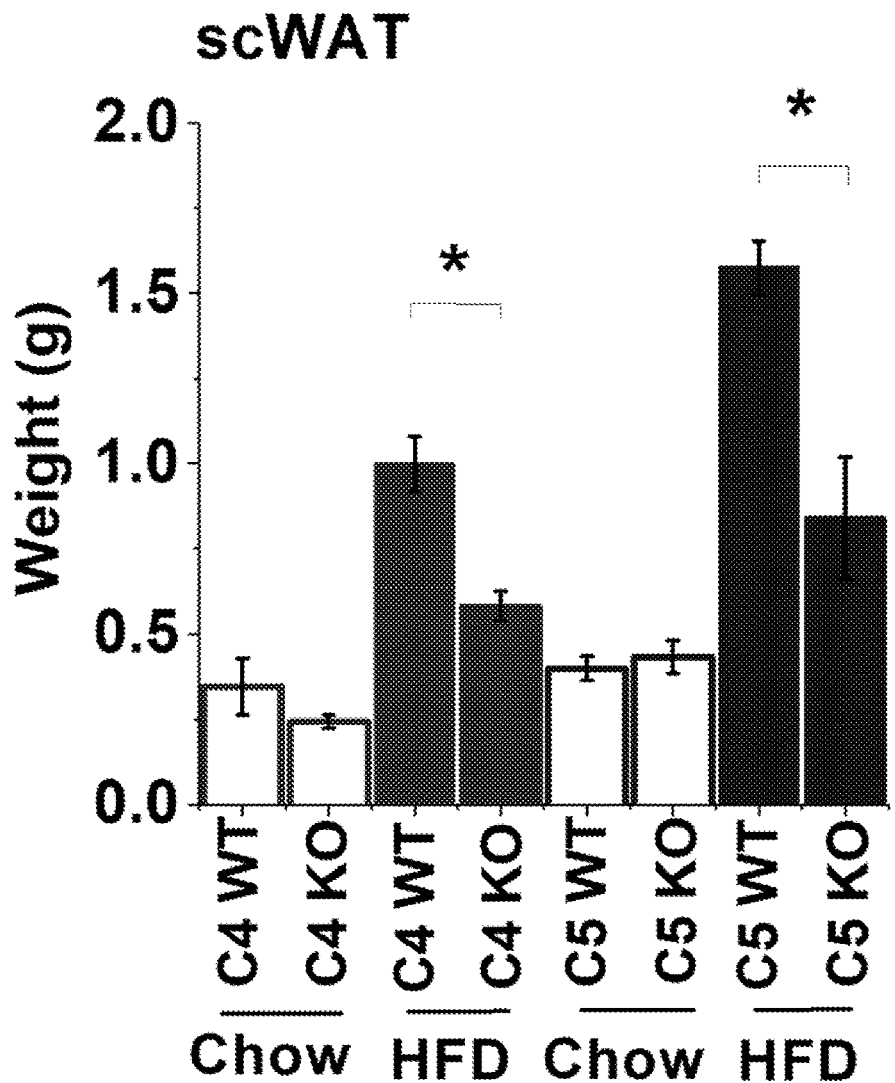
FIG. 3 demonstrates that TRPC4 knockout mice and TRPC5 knockout mice were unable to gain excess fat pad weight on high fat diet. Summary data for subcutaneous white adipose tissue (scWAT) fat pad weights of mice during 8 weeks of diet feeding (mean±SEM, n=7-8). Diets were chow (Chow) or 60% high-fat (HFD). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.

Mice were next studied on 60% high-fat diet (excess calorie intake). Subcutaneous white adipose tissue (scWAT) fat pad weights of mice (C4WT, C5WT, C4KO and C5KO) during 8 weeks of diet feeding were measured (n=7-8). Diets were chow (Chow) or 60% high-fat (HFD). Control wild-type (WT) litter-mates (C4$^{WT}$ and C5$^{WT}$) gained excess fat pad weight as expected during the 8 week experiment period (FIG. 3). C4$^{KO}$ and C5$^{KO}$ mice were, by contrast, strikingly similar to mice on chow diet, showing only normal weight gain as the mice matured (FIG. 3).

Example 4: Protection Against Hyperglycaemia

Figure 4:
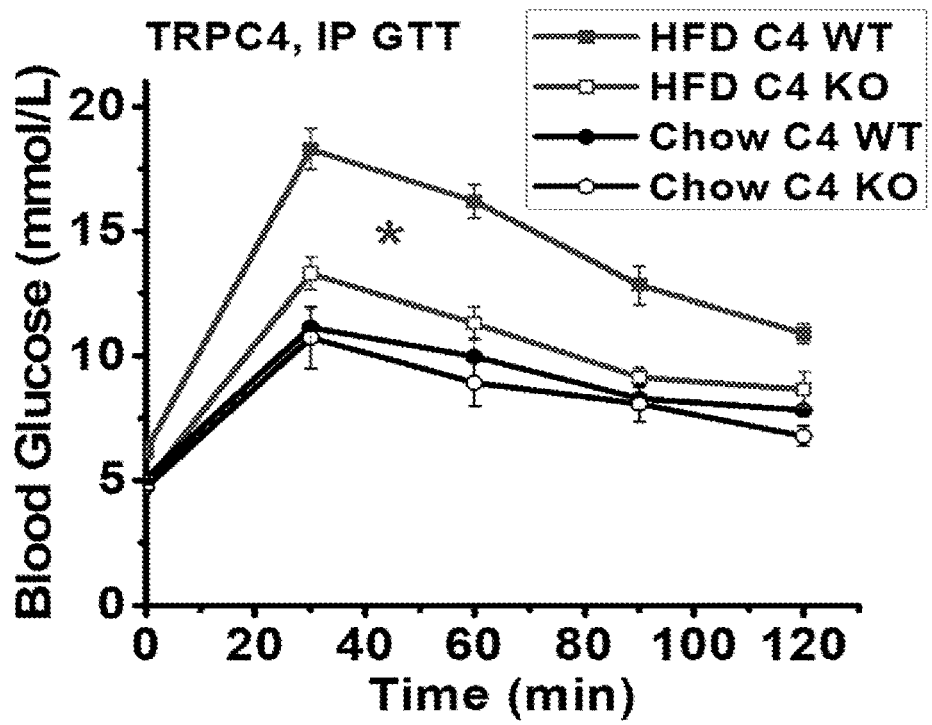
FIG. 4 demonstrates that TRPC4 knockout mice and TRPC5 knockout mice show protection against hyperglycaemia. Blood glucose concentrations after bolus intraperitoneal (IP) injection of glucose (glucose tolerance test, GTT). Mice were on chow or 60% high fat diet (HFD) (mean±SEM, n=7-8). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.
Figure 4:
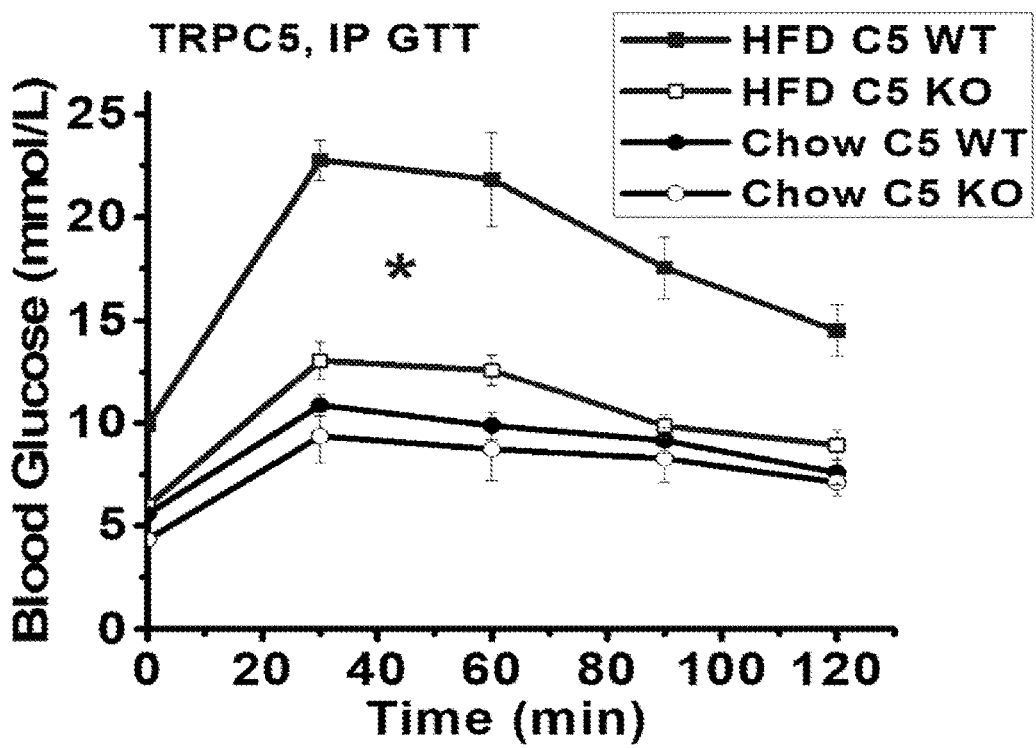

Blood glucose concentrations after bolus intraperitoneal (IP) injection of glucose (glucose tolerance test, GTT) were also measured for mice (C4WT, C5WT, C4KO and C5KO) on chow or 60% high fat diet (HFD) (n=7-8). Wild-type mice on 60% high-fat diet showed hyperglycemia (FIG. 4), which is an expected additional characteristic of animals on excess calorie intake. However, C4$^{KO}$ and C5$^{KO}$ mice on this diet were protected against these effects (FIG. 4).

Example 5: Protection Against Insulin-Resistance

Figure 5:
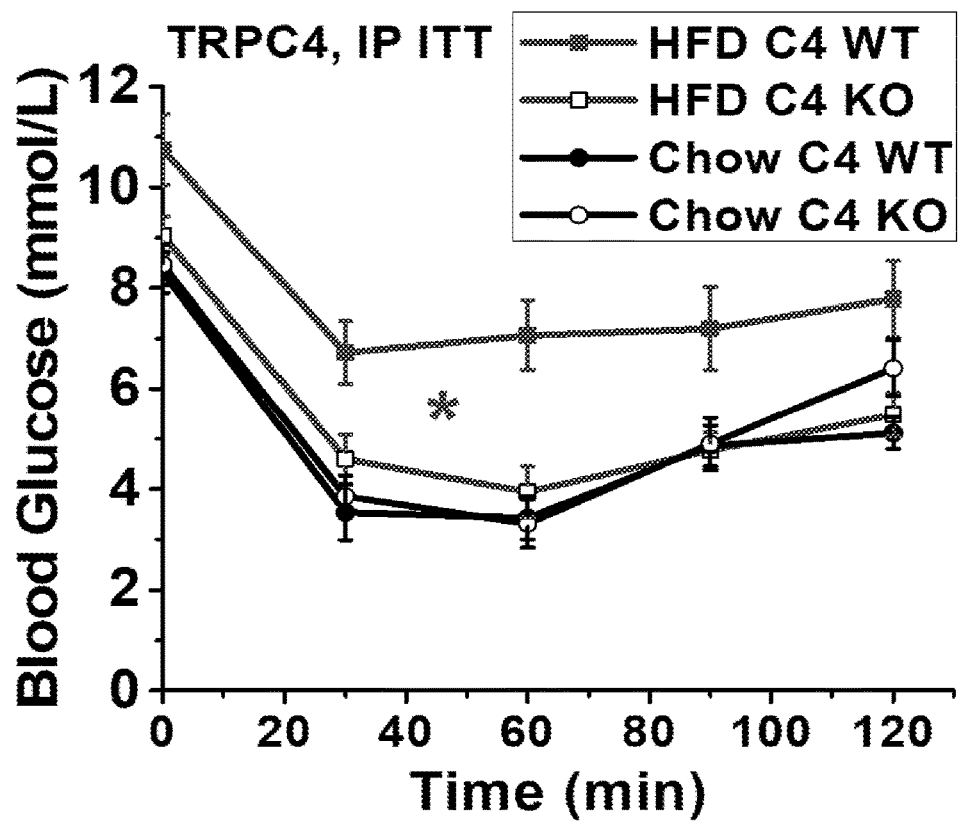
FIG. 5 demonstrates that TRPC4 knockout mice and TRPC5 knockout mice show protection against insulin-resistance. Blood glucose concentrations after bolus intraperitoneal (IP) injection of insulin (insulin tolerance test, ITT). Mice were either on chow or 60% high fat diet (HFD) (mean±SEM, n=7-8). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.
Figure 5:
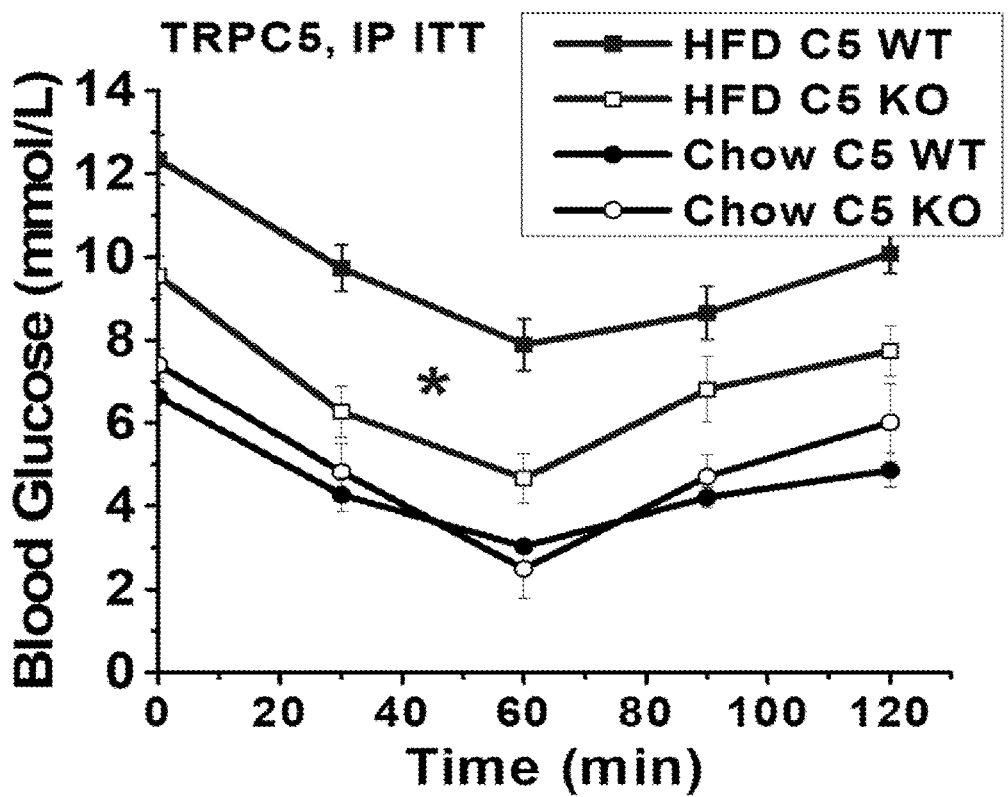

Blood glucose concentrations after bolus intraperitoneal (IP) injection of insulin (insulin tolerance test, ITT) were also measured for mice (C4WT, C5WT, C4KO and C5KO) on chow or 60% high fat diet (HFD) (n=7-8). Wild-type mice on 60% high-fat diet showed insulin-resistance (FIG. 5), which is an expected additional characteristic of animals on excess calorie intake. However, C4$^{KO}$ and C5$^{KO}$ mice on this diet were protected against these effects (FIG. 5).

Example 6: Protection Against Systemic Inflammation

Figure 6:
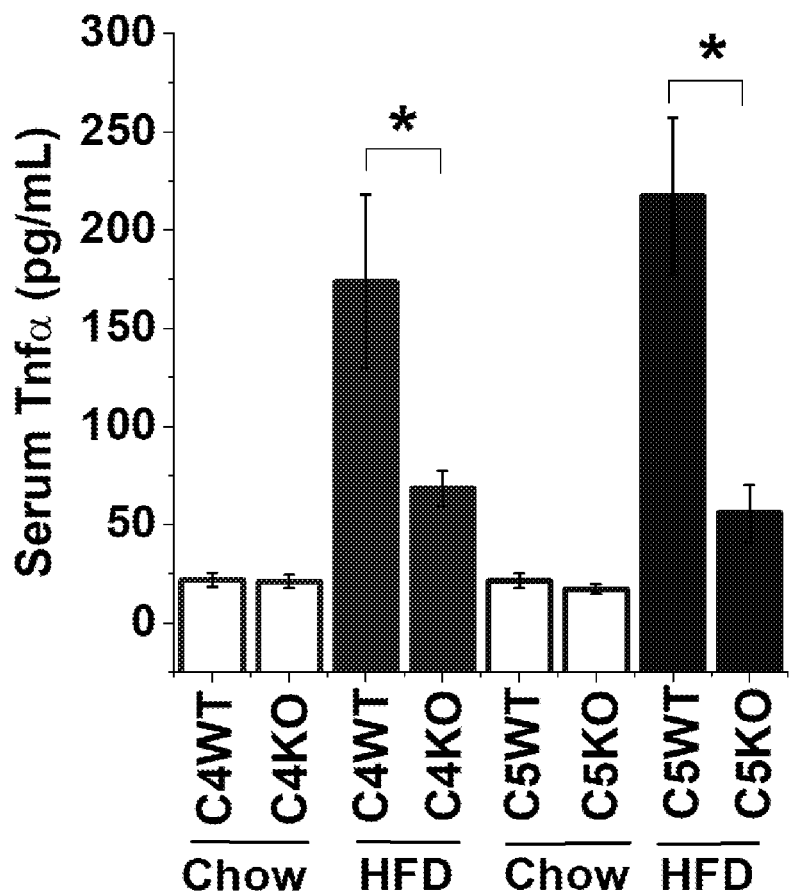
FIG. 6 demonstrates that TRPC4 knockout mice and TRPC5 knockout mice show protection against systemic inflammation. Serum tumour necrosis factor alpha (TNFα) concentration measured by ELISA. Mice were either on chow or 60% high fat diet (HFD) (mean±SEM, n=5). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.

Serum tumour necrosis factor alpha (TNFα) concentration was measured by ELISA in mice (C4WT, C5WT, C4KO and C5KO) on chow or 60% high fat diet (HFD) (n=5). Wild-type mice on 60% high-fat diet showed systemic tissue inflammation (FIG. 6), which is an expected additional characteristic of animals on excess calorie intake. However, C4$^{KO}$ and C5$^{KO}$ mice on this diet were protected against these effects (FIG. 6).

Example 7: Protection Against Adipose Tissue Inflammation

Figure 7:
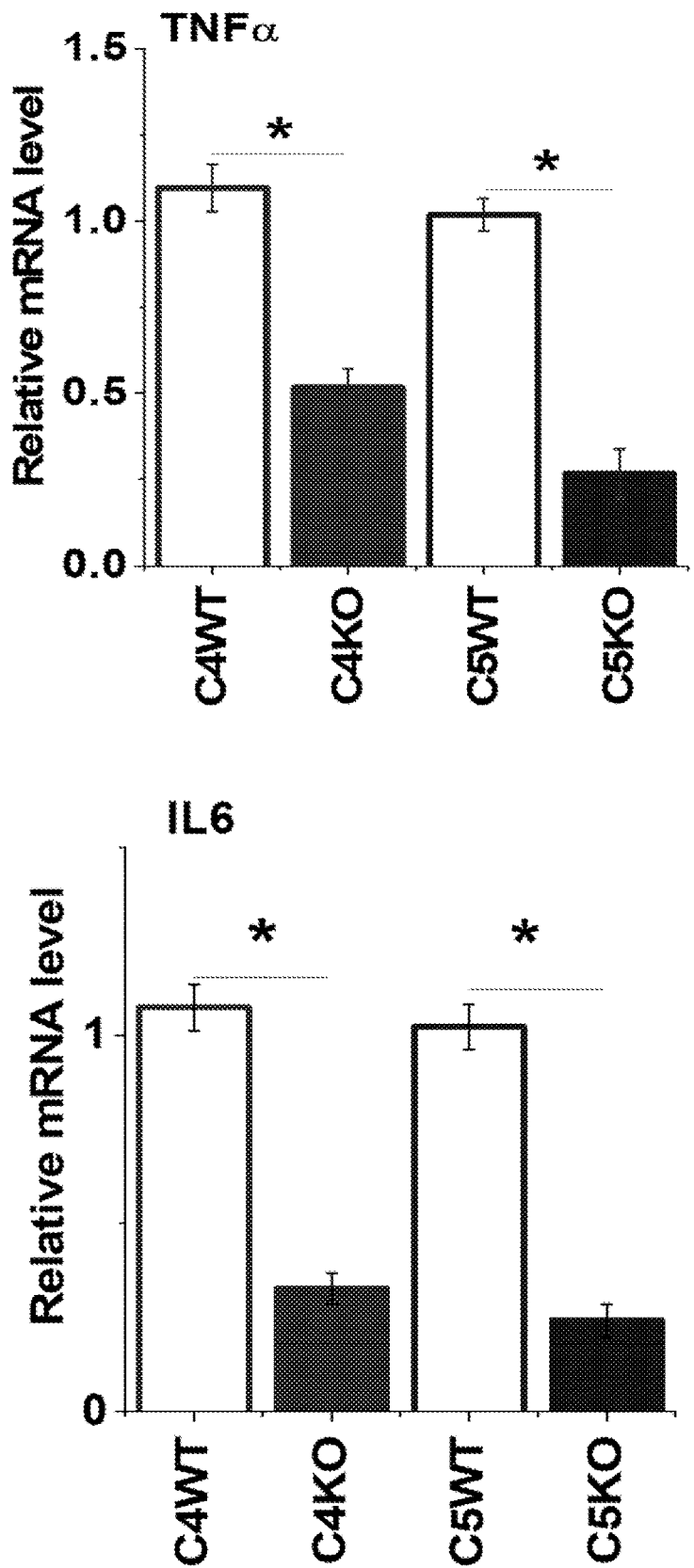
FIG. 7 demonstrates that TRPC4 knockout mice and TRPC5 knockout mice show protection against adipose tissue inflammation. Relative mRNA analysis for the pro-inflammatory markers TNFα and interleukin-6 (IL6) in fat pad. Mice were either on chow or 60% high fat diet (HFD) (mean±SEM, n=4). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.

Relative mRNA analysis for the pro-inflammatory markers TNFα and interleukin-6 (IL6) in fat pad were also measured for mice (C4WT, C5WT, C4KO and C5KO) on chow or 60% high fat diet (HFD) (n=4). Wild-type mice on 60% high-fat diet showed adipose tissue inflammation (FIG. 7), which is an expected additional characteristic of animals on excess calorie intake. However, C4$^{KO}$ and C5$^{KO}$ mice on this diet were protected against these effects (FIG. 7).

Example 8: Protection Against Ectopic Fat in the Liver (Steatosis)

Figure 8:
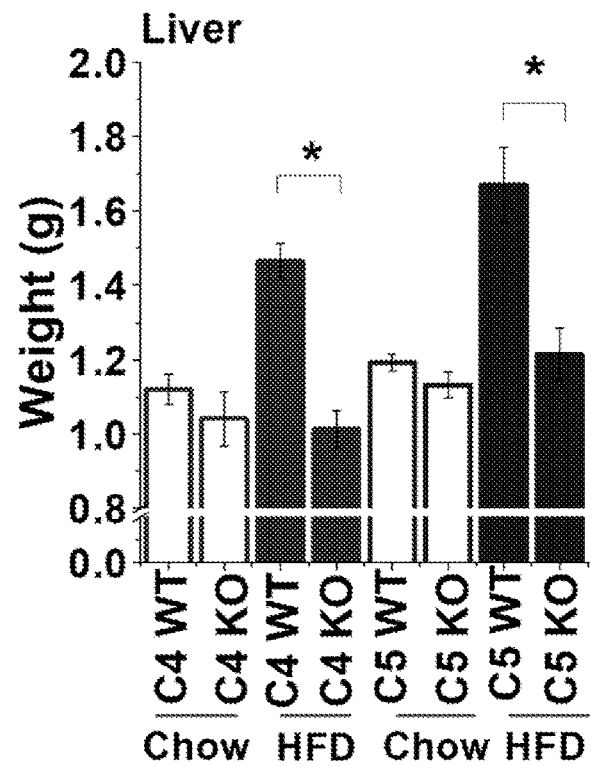
FIG. 8 demonstrates that TRPC4 knockout mice and TRPC5 knockout mice show protection against ectopic fat in the liver (steatosis). Total liver weight (upper bar chart, n=7-8) and percentage liver fat determined by histological analysis (lower bar chart, n=5). Mice were either on chow or 60% high fat diet (HFD). Data are mean±SEM. C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.
Figure 8:
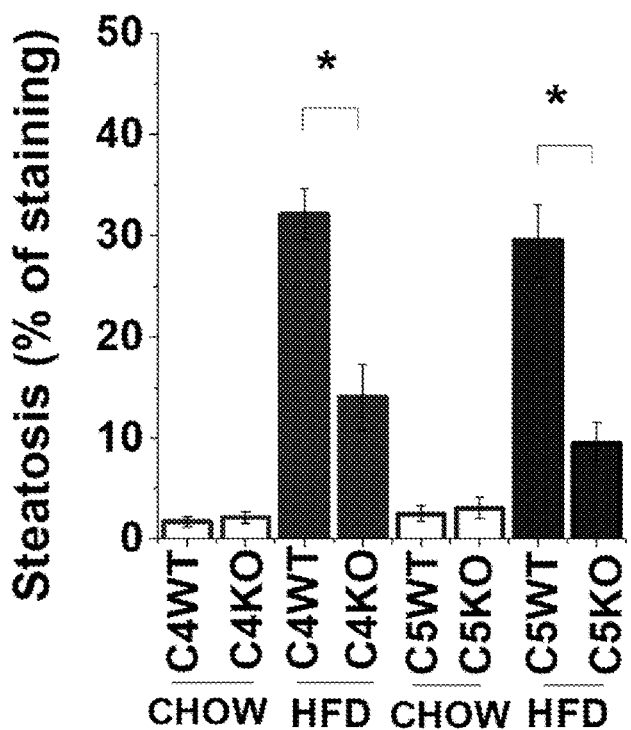

Total liver weight (FIG. 8 upper bar chart, n=7-8) and percentage liver fat determined by histological analysis (FIG. 8 lower bar chart, n=5) were also measured for mice (C4WT, C5WT, C4KO and C5KO) on chow or 60% high fat diet (HFD). Wild-type mice on 60% high-fat diet showed steatosis (FIG. 8), which is an expected additional characteristic of animals on excess calorie intake. However, C4$^{KO}$ and C5$^{KO}$ mice on this diet were protected against these effects (FIG. 8).

Example 9: No Change in Food Intake or Excretion

Figure 9:
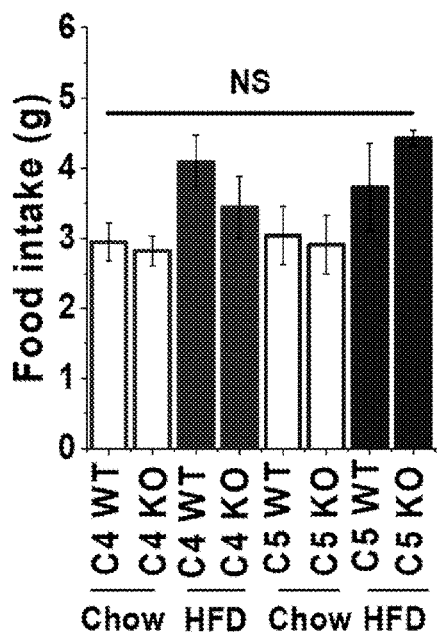
FIG. 9 demonstrates that TRPC4 knockout mice and TRPC5 knockout mice show no change in food intake or excretion. Food intake, fecal excretion and urinary excretion were determined in mice housed in metabolic cages (mean±SEM, n=6). Mice were either on chow or 60% high fat diet (HFD). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.
Figure 9:
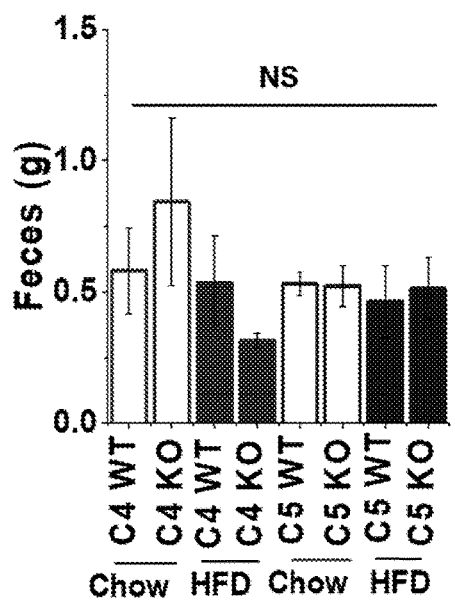
Figure 9:
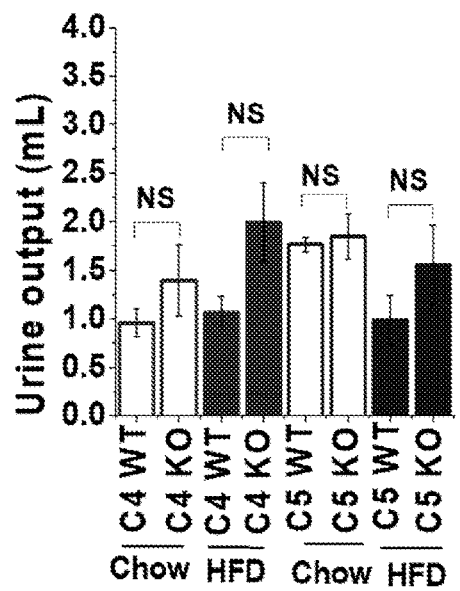

In order to determine whether the protection observed in C4$^{KO}$ and C5$^{KO}$ mice could be explained by differences in food intake or excretion, food intake, fecal excretion and urinary excretion were determined in mice housed in metabolic cages (n=6). Mice (C4WT, C5WT, C4KO and C5KO) were either on chow or 60% high fat diet (HFD). The protection observed in C4$^{KO}$ and C5$^{KO}$ mice was not explained by differences in food intake or excretion (FIG. 9).

Example 10: Increased Expression of Markers of White-to-Brown Adipocyte Phenotypic Switch ("Beiging")

An alternative explanation could be that white adipocytes in C4$^{KO}$ and C5$^{KO}$ mice shift to a thermogenic ("energy-burning") phenotype, often referred to as adipocyte beiging.

Figure 10:
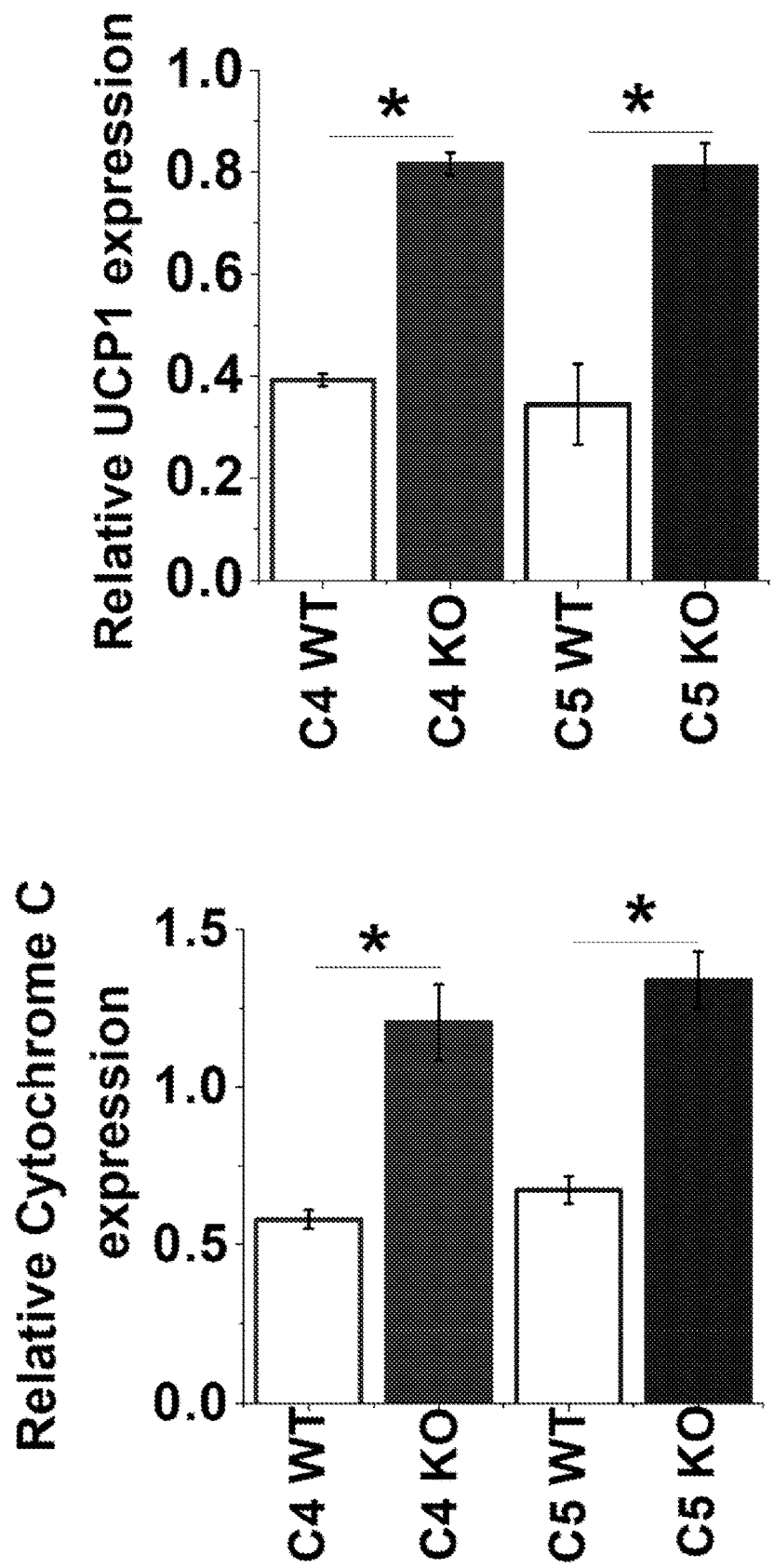
FIG. 10 demonstrates that TRPC4 knockout mice and TRPC5 knockout mice show increased expression of markers of white-to-brown adipocyte phenotype switch ("beiging"). Summary data for western blot analysis of UCP1 and Cytochrome C in subcutaneous white adipose tissue (mean±SEM, n=4). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.

Western blot analysis of UCP1 and Cytochrome C in subcutaneous white adipose tissue (n=4) was carried out in C4WT, C5WT, C4KO and C5KO mice. In support of this idea there was greater expression of the mitochondrial proteins UCP1 and Cytochrome C in white adipose tissue of C4$^{KO}$ and C5$^{KO}$ mice (FIG. 10).

Example 11: Increased Adipocyte Thermogenesis

Oxygen consumption was also measured in adipocytes from subcutaneous white adipose tissue of C4WT, C5WT, C4KO and C5KO mice (n=3-4). Oxygen consumption was measured for routine respiration after addition of sodium pyruvate, mitochondrial leak after addition of oligomycin, maximum electron transport chain-mediated oxygen consumption after sequential FCCP addition (ETS), and non-OXPHO respiration after addition of rotenone and antimycin A (ROX).

Figure 11:
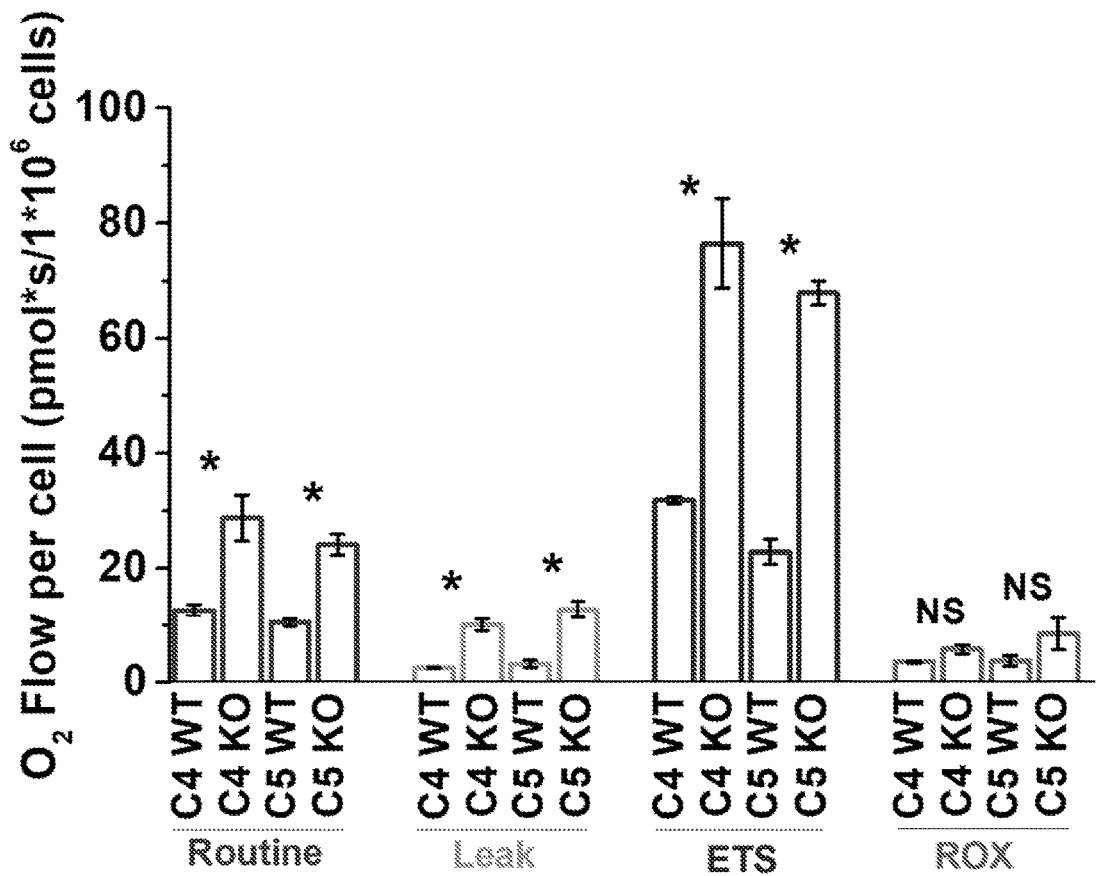
FIG. 11 demonstrates that TRPC4 knockout mice and TRPC5 knockout mice show increased adipocyte thermogenesis. Oxygen consumption data for adipocytes from subcutaneous white adipose tissue of mice. Data are for routine respiration after addition of sodium pyruvate, mitochondrial leak after addition of oligomycin, maximum electron transport chain-mediated oxygen consumption after sequential FCCP addition (ETS), and non-OXPHO respiration after addition of rotenone and antimycin A (ROX). C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. Data are mean±SEM (n=3-4). * indicates statistically significantly different.

High-resolution respirometry showed increased mitochondrial respiration in adipocytes of C4$^{KO}$ and C5$^{KO}$ mice (FIG. 11), providing further support that white adipocytes in C4$^{KO}$ and C5$^{KO}$ mice shift to a thermogenic ("energy-burning") phenotype.

Example 12: Inhibition of TRPC4 and TRPC5 Channels by DE2 and C31

Figure 12:
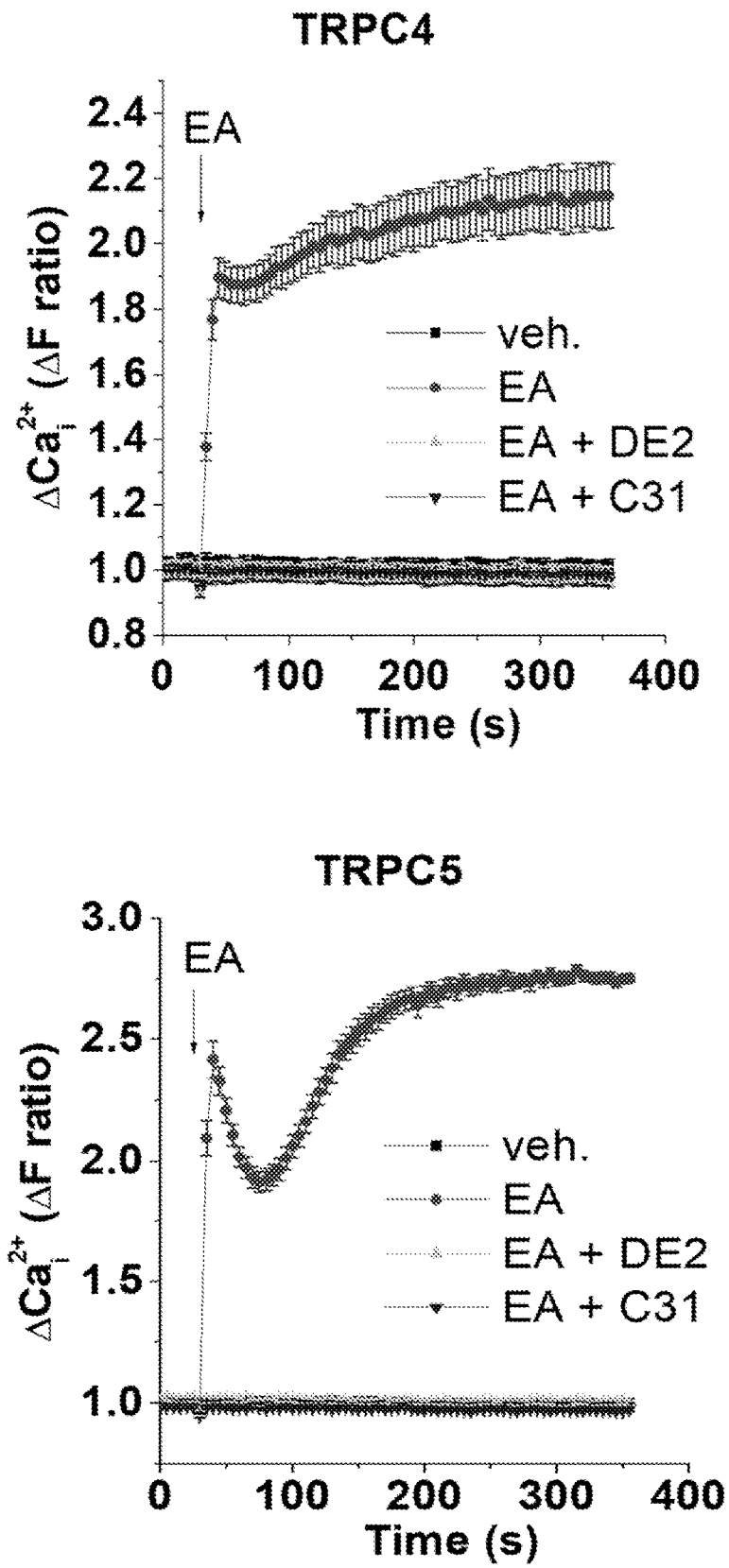
FIG. 12 demonstrates the inhibition of TRPC4 and TRPC5 channels by DE2 and C31. Representative intracellular $Ca^{2+}$ measurements from HEK 293 cells stably expressing inducible human TRPC4 (upper panel) or human TRPC5 (lower panel). Data are mean±SEM (3-4 replicates each) and representative of 4 independent experiments each. Channels were activated by the TRPC4/TRPC5 channel agonist (−)-Englerin A (EA, 100 nM). The vehicle control was DMSO. Cells were pre-incubated with (30 min) and maintain in 10 µM DE2 or 100 nM C31 where indicated.

To examine the effects of the small molecule inhibitors DE2 and C31, intracellular Ca$^{2+}$ measurements were made from HEK 293 cells stably expressing inducible human TRPC4 (upper panel) or human TRPC5 (lower panel). Data presented in FIG. 12 are mean±SEM (3-4 replicates each) and representative of 4 independent experiments each. Channels were activated by the TRPC4/TRPC5 channel agonist (−)-Englerin A (EA, 100 nM). The vehicle control was DMSO. Cells were pre-incubated with (30 min) and maintained in 10 μM DE2 or 100 nM C31 where indicated. DE2 and C31 demonstrated inhibition of TRPC4 and TRPC5 channels (FIG. 12).

Example 13: Small-Molecule Inhibitors Increase Adipocyte Thermogenesis

To examine the effect of DE2 and C31 on thermogenesis in adipocytes, oxygen consumption was measured in adipocytes from subcutaneous white adipose tissue of mice. Data are for routine respiration after addition of sodium pyruvate, mitochondrial leak after addition of oligomycin, maximum electron transport chain-mediated oxygen consumption after sequential FCCP addition (ETS), and non-OXPHO respiration after addition of rotenone and antimycin A (ROX). Cells were pre-incubated with (24 hr) and maintained in 10 μM DE2 or 100 nM C31 where indicated. The vehicle control was DMSO.

Figure 13:
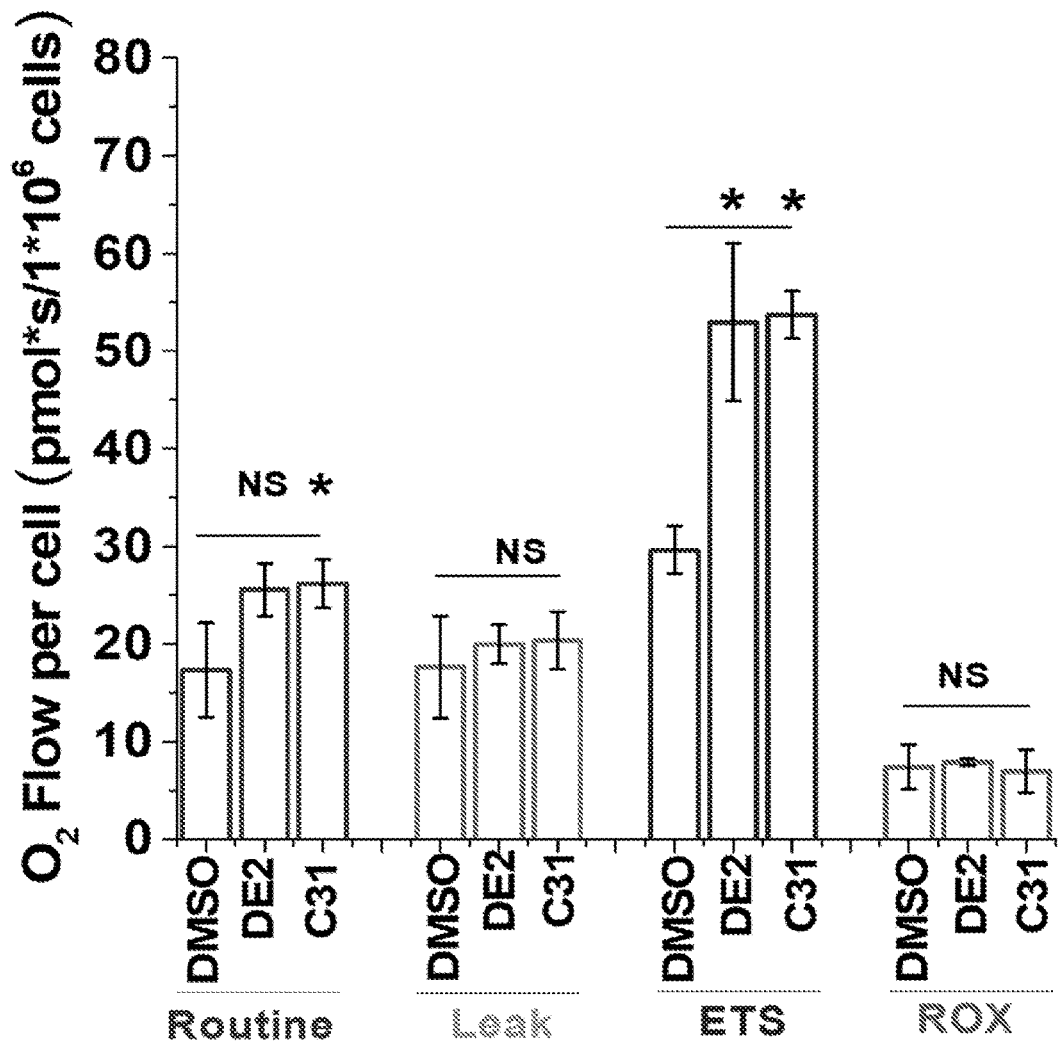
FIG. 13 demonstrates that small-molecule inhibitors increase adipocyte thermogenesis. Oxygen consumption data for adipocytes from subcutaneous white adipose tissue of mice. Data are for routine respiration after addition of sodium pyruvate, mitochondrial leak after addition of oligomycin, maximum electron transport chain-mediated oxygen consumption after sequential FCCP addition (ETS), and non-OXPHO respiration after addition of rotenone and antimycin A (ROX). Cells were pre-incubated with (24 hr) and maintain in 10 µM DE2 or 100 nM C31 where indicated. The vehicle control was DMSO.

Incubation with both agents (DE2 and C31) caused increases in adipocyte mitochondrial respiration (FIG. 13). The effects were quantitatively similar to those caused by TRPC4 and TRPC5 knockout.

Example 14: Small-Molecule Inhibitors Increase Expression of Markers of White-to-Brown Adipocyte Phenotypic Switch ("Beiging")

To determine the influence of DE2 and C31 on expression of markers of white-to-brown adipocyte phenotypic switching, transcript accumulation of UCP1 and Cytochrome C was measured by mRNA analysis in adipocytes from subcutaneous white adipose tissue (n=4-5) of C4WT, C5WT, C4KO, and C5KO mice. Cells were pre-incubated with (24 hr) and maintained in 10 μM DE2 or 100 nM C31 where indicated. The vehicle control was DMSO.

Figure 14:
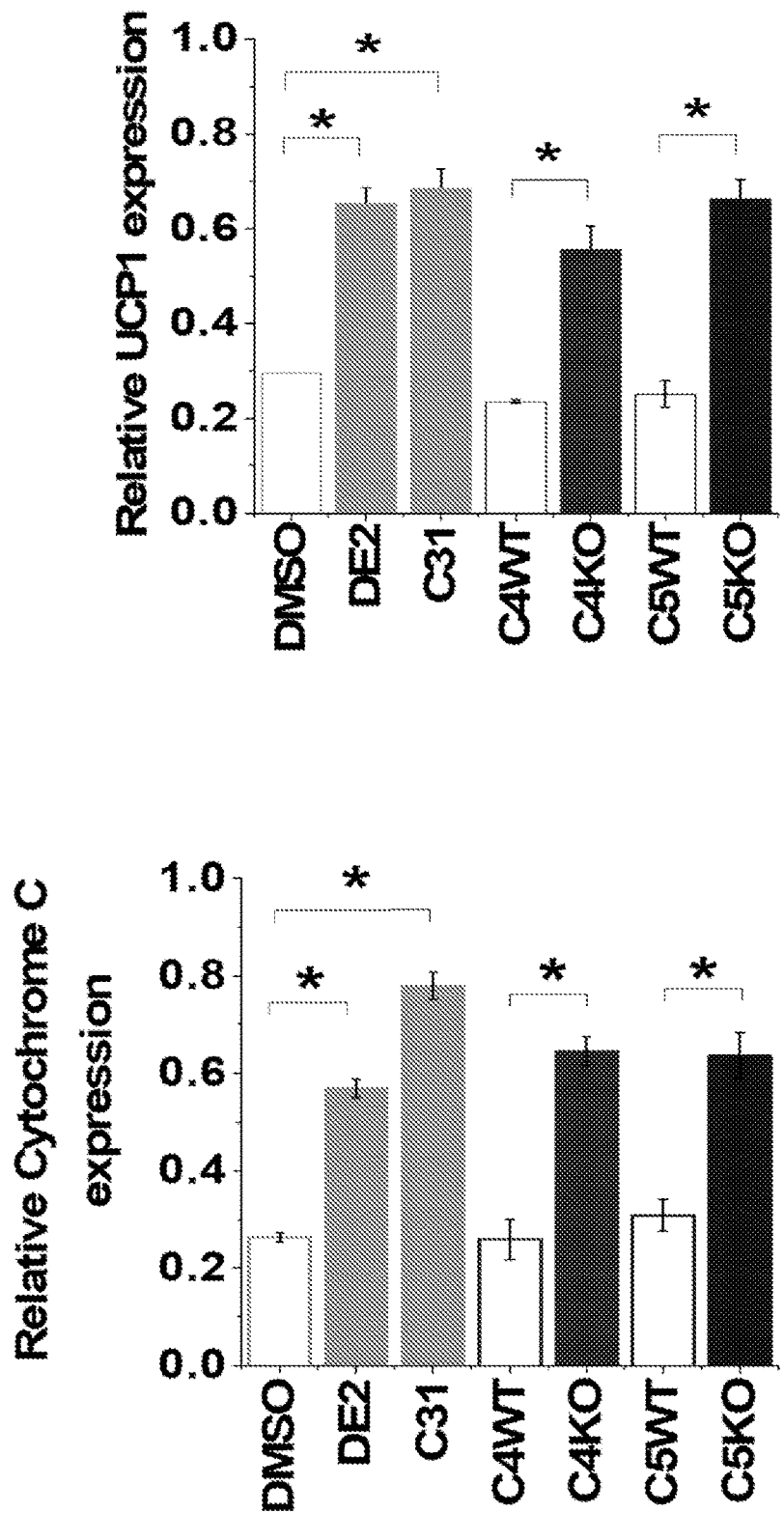
FIG. 14 demonstrates that the small-molecule inhibitors C31 and DE2 increase expression of markers of white-to-brown adipocyte phenotype switch ("beiging"). Summary data for mRNA analysis of UCP1 and Cytochrome C expression in adipocytes from subcutaneous white adipose tissue (mean±SEM, n=4-5). Cells were pre-incubated with (24 hr) and maintain in 10 µM DE2 or 100 nM C31 where indicated. The vehicle control was DMSO. C4WT, wildtype litter-mate controls for TRPC4 knockout mice. C5WT, wildtype litter-mate controls for TRPC5 knockout mice. C4KO, TRPC4 knockout mice. C5KO, TRPC5 knockout mice. * indicates statistically significantly different.

Incubation with both agents (DE2 and C31) caused increases in adipocyte UCP1/Cytochrome C expression (FIG. 14). The effects were quantitatively similar to those caused by TRPC4 and TRPC5 knockout (FIG. 14).

Figure 15:
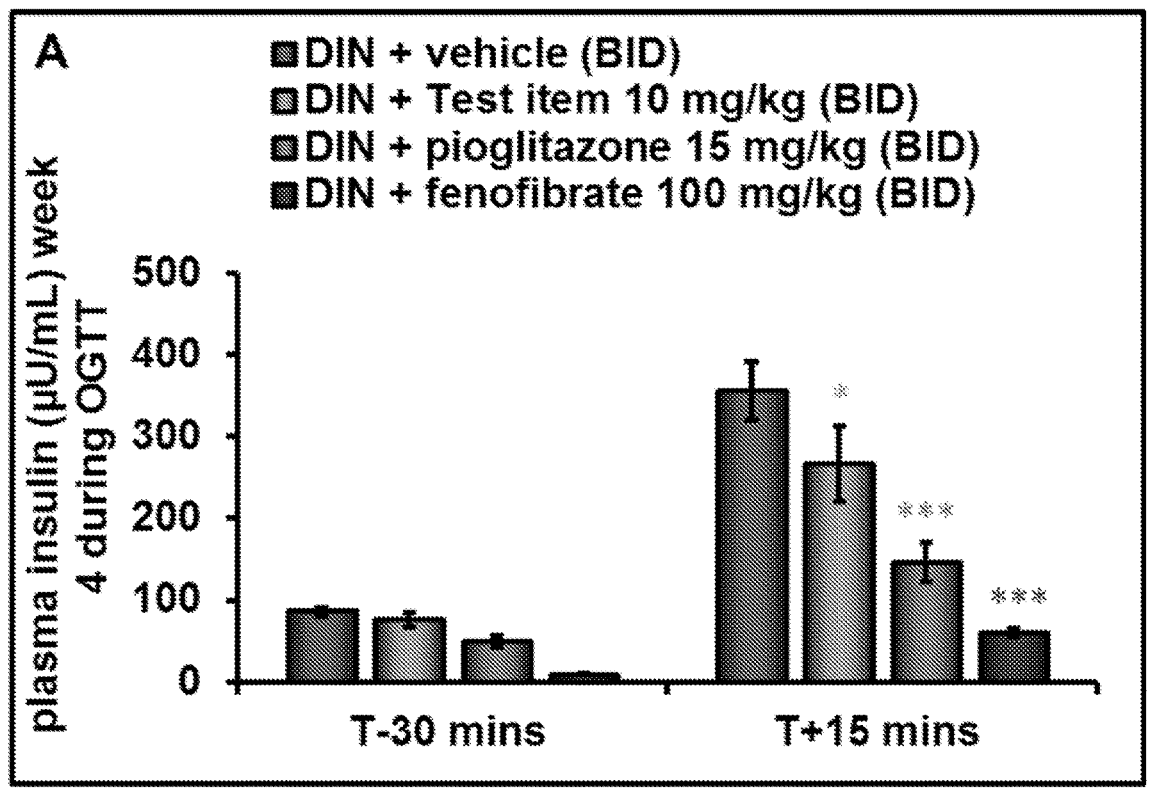
FIG. 15 demonstrates that bi-daily oral dosing (BID) with C31 (designated "Test item" in the figure) significantly reduced plasma insulin after an oral glucose tolerance test (OGTT) in HFD-fed wildtype adult male mice (DIN). Data for comparator established drugs are also shown. N=10 per group.

Example 15: Small Molecules Significantly Reduced Plasma Insulin Following Oral Dosing C31 (designated "Test item" in FIG. 15) was administered to HFD-fed wildtype adult male mice (DIN) with a bi-daily oral dosing (BID) regimen (N=10 per group). In parallel groups comparator, established drugs were also administered. The HFD-fed wildtype adult male mice (DIN) administered with C31 had significantly reduced plasma insulin after an oral glucose tolerance test (OGTT), see FIG. 15.

Figure 16:
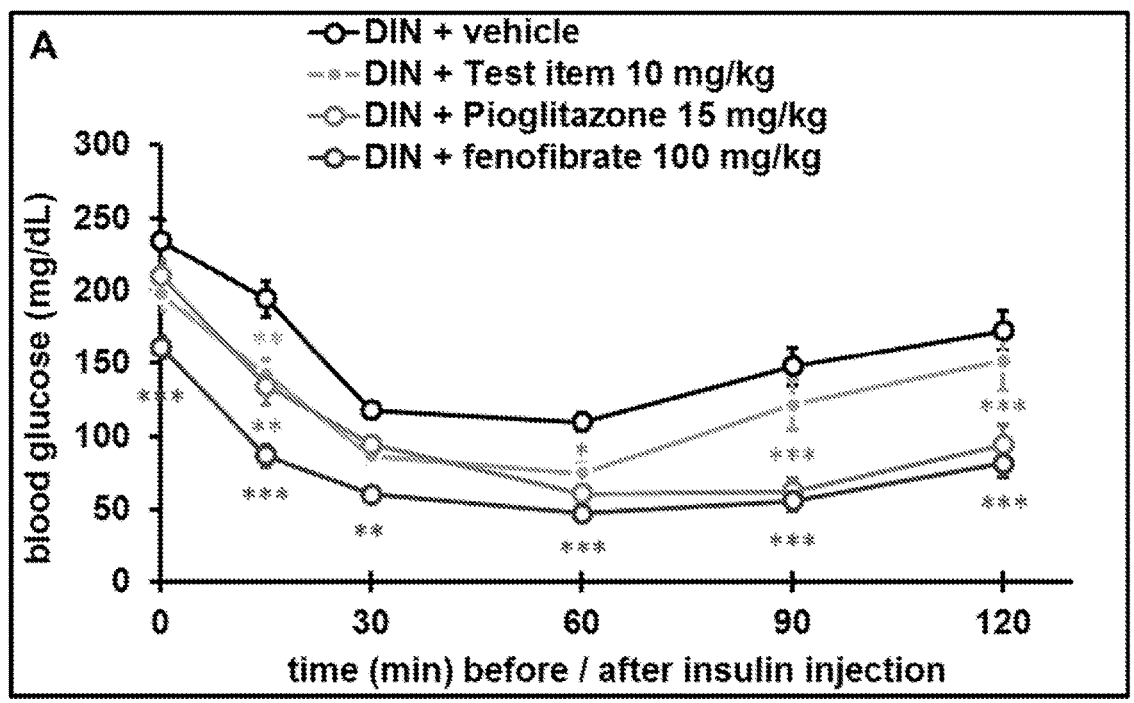
FIG. 16 demonstrates that bi-daily oral dosing (BID) with C31 (designated "Test item" in the figure) significantly reduced blood glucose after an insulin tolerance test in HFD-fed wildtype adult male mice (DIN). Data for comparator established drugs are also shown. N=10 per group.

In a similar study, C31 (designated "Test item" in FIG. 16) was administered to HFD-fed wildtype adult male mice (DIN) with a bi-daily oral dosing (BID) regimen (N=10 per group). In parallel groups comparator, established drugs were also administered. The HFD-fed wildtype adult male mice (DIN) administered with C31 had significantly reduced blood glucose after an insulin tolerance test (FIG. 16).

Example 16

Figure 17:
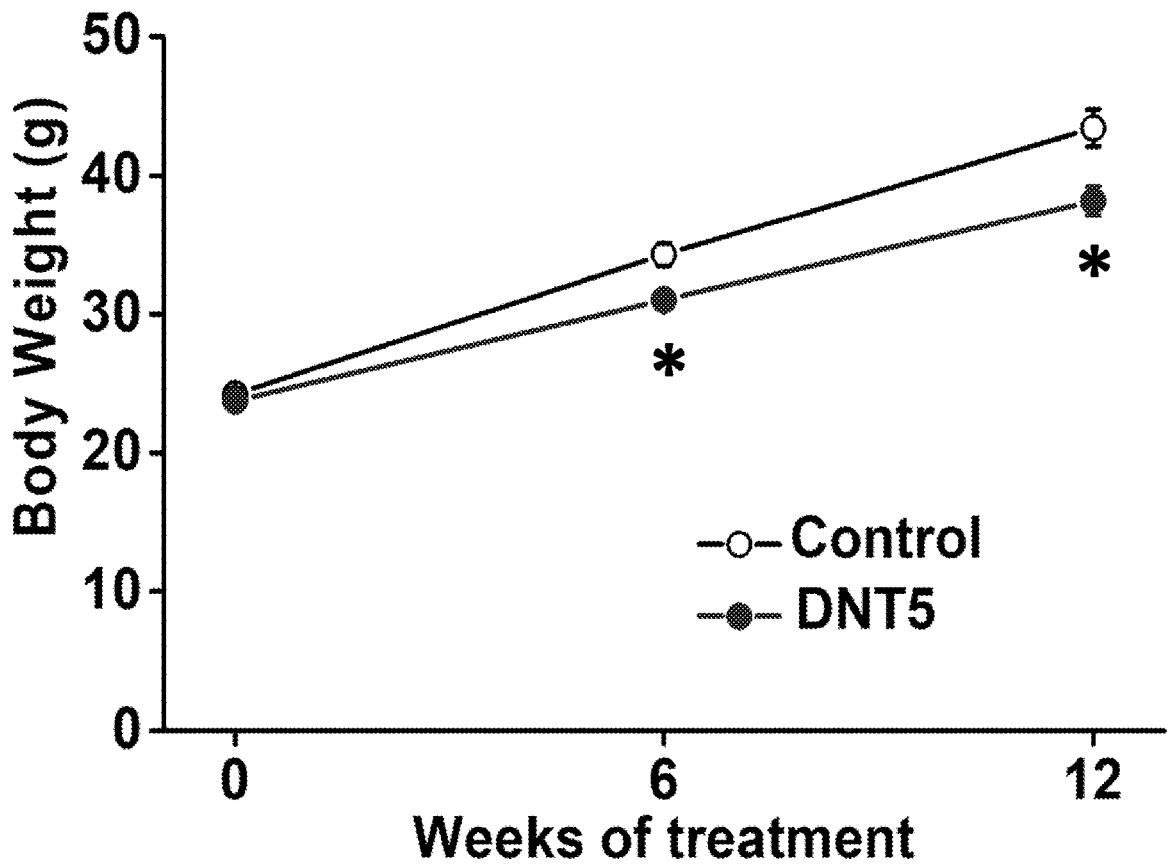
FIG. 17 demonstrates that in vivo expression of a dominant negative TRPC5 ion pore mutant from a transgene (DNT5) significantly reduced body weight gain in hypercholesterolaemic (ApoE−/−) adult male mice fed western-style diet. The mutant enters native TRPC1/4/5 channels to inhibit ion permeation. N=16 DNT5 mice and N=19 control littermates (which lacked DNT5).

In a study including 16 DNT5 mice and 19 control littermates (which lacked DNT5) it was observed that in vivo expression of a dominant negative TRPC5 ion pore mutant from a transgene (DNT5) significantly reduced body weight gain in hypercholesterolaemic (ApoE−/−) adult male mice fed western-style diet. The mutant enters native TRPC1/4/5 channels to inhibit ion permeation (FIG. 17).

Figure 18:
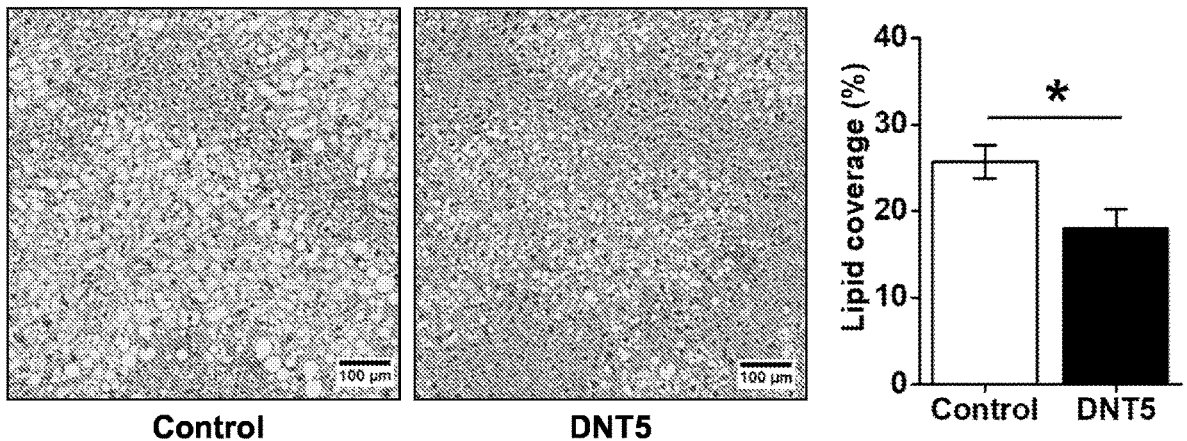
FIG. 18 demonstrates that in vivo expression of a dominant negative TRPC5 ion pore mutant from a transgene (DNT5) significantly reduced liver steatosis in hypercholesterolaemic (ApoE−/−) adult male mice fed western-style diet. N=14 DNT5 and N=11 control littermates (which lacked DNT5).

In a similar study including N=14 DNT5 and N=11 control littermates (which lacked DNT5) it was observed that in vivo expression of a dominant negative TRPC5 ion pore mutant from a transgene (DNT5) significantly reduced liver steatosis in hypercholesterolaemic (ApoE−/−) adult male mice fed western-style diet (FIG. 18).

The invention claimed is:
1. A method of treatment of a condition selected from obesity, insulin resistance, non-alcoholic fatty liver disease (NAFLD), and non-alcoholic steatohepatitis (NASH), or a combination thereof in a subject in need thereof, the method comprising administering to the subject a compound of the Formula (II), or a pharmaceutically acceptable salt thereof:

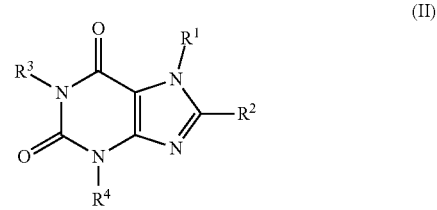

(II)

wherein:
R$^1$ is C$_{1-6}$ alkyl, C$_{2-6}$ alkenyl or C$_{2-6}$ alkynyl, each of which is optionally substituted with 1-4 R$^5$;
R$^2$ is C$_{1-6}$ alkyl, C$_{2-6}$ alkenyl, C$_{2-6}$ alkynyl, C$_{1-6}$ haloalkyl, halo, C$_{1-6}$ haloalkoxy, hydroxyl, C$_{1-6}$ alkoxy, C$_{3-7}$ cycloalkyloxy, C$_{6-10}$ aryl, C$_{6-10}$ aryloxy, C$_{7-16}$ arylalkoxy, amino, C$_{1-6}$ akylamino, C$_{2-12}$ dialkylamino, —S(O)$_x$R' (wherein x is 0, 1 or 2 and each R' is independently H or C$_{1-6}$ alkyl), heterocycloalkyl, heteroaryl, heteroaryloxy, —S(O)$_2$NR'R', wherein each R' is independently H or C$_{1-6}$ alkyl, —C(O)NR'R', wherein each R' is independently H or C$_{1-6}$ alkyl, —NR'C(O)NR'R', wherein each R' is independently H or C$_{1-6}$ alkyl, —S(O)$_2$NR'C(O)NR'R', wherein each R' is independently H or C$_{1-6}$ alkyl, —C(O)R', wherein R' is H or C$_{1-6}$ alkyl, nitro, cyano, wherein each C$_{1-6}$ alkyl, C$_{2-6}$ alkenyl, C$_{2-6}$ alkynyl, C$_{1-6}$ haloalkyl, C$_{1-6}$haloalkoxy, hydroxyl, C$_{1-6}$ alkoxy, C$_{3-7}$ cycloalkyloxy, C$_{6-10}$ aryl, C$_{6-10}$ aryloxy, C$_{7-16}$ arylalkoxy, amino, C$_{1-6}$ akylamino, C$_{2-12}$ dialkylamino, —S(O)$_x$R', heterocycloalkyl, heteroaryl, heteroaryloxy, —S(O)$_2$NR'R', wherein each R' is independently H or C$_{1-6}$ alkyl, —C(O)NR'R', wherein each R' is independently H or C$_{1-6}$ alkyl, —NR'C(O)NR'R', wherein each R' is independently H or C$_{1-6}$ alkyl, —S(O)$_2$NR'C(O)NR'R', wherein each R' is independently H or C$_{1-6}$ alkyl, —C(O)R', wherein R' is H or C$_{1-6}$ alkyl, is optionally substituted with 1-3 R$^6$;
R$^3$ is C$_{2-6}$ hydroxyalkyl;
R$^4$ is C$_{1-6}$ alkyl, C$_{2-6}$ alkenyl or C$_{2-6}$ alkynyl, each of which is optionally substituted with 1-4 R$^8$;
R$^5$, R$^6$, R$^7$, and R$^8$ are each independently hydrogen, C$_{1-6}$ alkyl, halo, C$_{1-6}$ haloalkyl, C$_{1-6}$ haloalkoxy, hydroxyl, C$_{1-6}$ alkoxy, amino, C$_{1-6}$ alkylamino, C$_{2-12}$ dialkylamino, cyano, nitro, —C(O)NR'R', wherein each R' is independently H or C$_{1-6}$ alkyl, —S(O)$_x$R' (wherein x is 0, 1 or 2), —C(O)OR', —C(O)R', C$_{3-7}$ cycloalkyl, C$_{6-10}$ aryl, heterocycloalkyl, or heteroaryl, wherein each R' is independently H or $C_{1-6}$ alkyl, wherein each of $C_{1-6}$ alkyl, $C_{1-6}$ haloalkyl, $C_{1-6}$ haloalkoxy, hydroxyl, $C_{1-6}$ alkoxy, amino, $C_{1-6}$ alkylamino, $C_{2-12}$ dialkylamino, —C(O)NR'R', wherein each R' is independently H or $C_{1-6}$ alkyl, —C(O)O—$C_{1-6}$ alkyl, $C_{3-7}$ cycloalkyl, $C_{6-10}$ aryl, heterocycloalkyl, or heteroaryl is optionally substituted with 1-3 $R^9$; and each $R^9$ is independently $C_{1-6}$ alkyl, $C_{1-6}$ haloalkyl, $C_{1-6}$ haloalkoxy, heterocycloalkyl, $C_{6-10}$ aryl, heteroaryl, $C_{4-10}$ cycloalkylalkyl, heterocycloalkyl-$C_{1-6}$ alkyl, $C_{7-16}$ arylalkyl, heteroaryl-$C_{1-6}$ alkyl, halo, hydroxyl, $C_{1-6}$ alkoxy, $C_{6-10}$ aryloxy, $C_{7-16}$ arylalkoxy, $C_{2-8}$ alkoxyalkoxy, amino, $C_{1-6}$ akylamino, $C_{2-12}$ dialkylamino, $C_{1-6}$ alkyl-amino-$C_{1-6}$ alkyl, $C_{1-6}$ alkyl-amino-$C_{2-12}$ dialkyl, —S(O)$_x$R' (wherein x is 0, 1 or 2), —S(O)$_2$NR'R', wherein each R' is independently H or $C_{1-6}$ alkyl, —C(O)NR'R', wherein each R' is independently H or $C_{1-6}$ alkyl, —NR'C(O)NR'R', wherein each R' is independently H or $C_{1-6}$ alkyl, —S(O)$_2$NR'C(O)NR'R', wherein each R' is independently H or $C_{1-6}$ alkyl, —C(O)R', wherein R' is H or $C_{1-6}$ alkyl, —C(O)—$C_{1-6}$ alkyl, —C(O)—$C_{6-10}$ aryl, —NHC(O)—$C_{1-4}$ alkyl, —NHC(O)—$C_{6-10}$ aryl, —C(O)NR'R', —C(O)NH—$C_{6-10}$ aryl, —C(O)OR', —OC(O)R', nitro, or cyano;

wherein a "heterocycloalkyl" group is a non-aromatic saturated or partially saturated monocyclic heterocyclic ring system(s) containing from 3 to 12 ring atoms, with from 1 to 5 heteroatoms selected from nitrogen, oxygen or sulfur in the ring;

wherein a "heteroaryl" group is monocyclic and bicyclic groups containing from five to twelve ring members, wherein each ring may contain up to four heteroatoms selected from nitrogen, sulfur and oxygen.

2. The method of claim 1, wherein the condition is obesity.

3. The method of claim 1, wherein the condition is insulin resistance in a subject.

4. The method of claim 3, wherein the subject is obese.

5. The method of claim 3 wherein the insulin resistance is associated with Type II diabetes or prediabetes.

6. The method of claim 1, wherein the compound is administered to a subject predetermined to have an elevated level in adipose tissue relative to control of TRPC4 mRNA and/or protein.

7. The method of claim 6, wherein the subject's predetermination to having an elevated level in adipose tissue relative to control of TRPC4 mRNA and/or protein occurs by a method comprising determining the level of TRPC4 mRNA and/or protein in a sample of adipose tissue from the subject; and selecting said subject for administration of the compound if the level of said screening target exceeds a control level.

8. The method of claim 1, wherein the compound is:

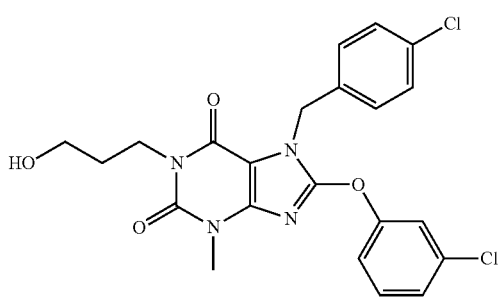

or

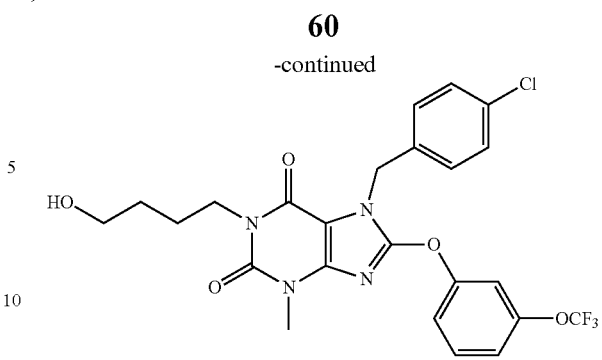

or pharmaceutically acceptable salt thereof.

9. The method of claim 1, wherein the compound is:

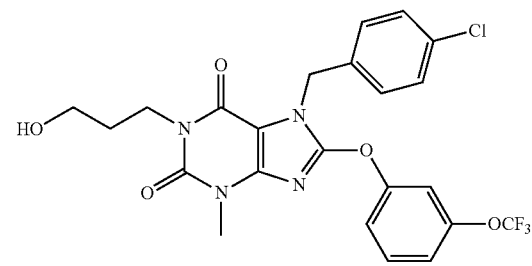 [SMILES: Cn1c(=O)n(CCCO)c(=O)c2c1nc(Oc1cccc(OC(F)(F)F)c1)n2Cc1ccc(Cl)cc1]

or a pharmaceutically acceptable salt thereof.

10. A cosmetic method of reducing or inhibiting excess weight gain in a subject in need thereof, the method comprising administering to the subject a compound of the Formula (II), or a pharmaceutically acceptable salt thereof:

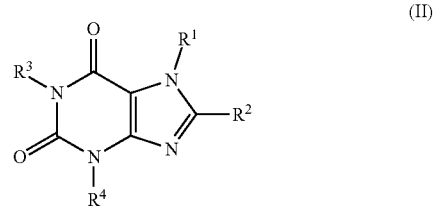

(II)

wherein:
$R^1$ is $C_{1-6}$ alkyl, $C_{2-6}$ alkenyl or $C_{2-6}$ alkynyl, each of which is optionally substituted with 1-4 $R^5$;

$R^2$ is $C_{1-6}$ alkyl, $C_{2-6}$ alkenyl, $C_{2-6}$ alkynyl, $C_{1-6}$ haloalkyl, halo, $C_{1-6}$ haloalkoxy, hydroxyl, $C_{1-6}$ alkoxy, $C_{3-7}$ cycloalkyloxy, $C_{6-11}$) aryl, $C_{6-10}$ aryloxy, $C_{7-16}$ arylalkoxy, amino, $C_{1-6}$ akylamino, $C_{2-12}$ dialkylamino, —S(O)$_x$R' (wherein x is 0, 1 or 2 and each R' is independently H or $C_{1-6}$ alkyl), heterocycloalkyl, heteroaryl, heteroaryloxy, —S(O)$_2$NR'R', wherein each R' is independently H or $C_{1-6}$ alkyl, —C(O)NR'R', wherein each R' is independently H or $C_{1-6}$ alkyl, —NR'C(O)NR'R', wherein each R' is independently H or $C_{1-6}$ alkyl, —S(O)$_2$NR'C(O)NR'R', wherein each R' is independently H or $C_{1-6}$ alkyl, —C(O)R', wherein R' is H or $C_{1-6}$ alkyl, nitro, cyano, wherein each $C_{1-6}$ alkyl, $C_{2-6}$ alkenyl, $C_{2-6}$ alkynyl, $C_{1-6}$ haloalkyl, $C_{1-6}$haloalkoxy, hydroxyl, $C_{1-6}$ alkoxy, $C_{3-7}$ cycloalkyloxy, $C_{6-11}$) aryl, $C_{6-11}$) aryloxy, $C_{7-16}$ arylalkoxy, amino, $C_{1-6}$ akylamino, $C_{2-12}$ dialkylamino, —S(O)$_x$R', heterocycloalkyl, heteroaryl, heteroaryloxy, —S(O)$_2$NR'R', wherein each R' is independently H or $C_{1-6}$ alkyl, —C(O)NR'R', wherein each R' is independently H or $C_{1-6}$ alkyl, —NR'C(O)NR'R', wherein each R' is independently H or $C_{1-6}$ alkyl, —S(O)$_2$NR'C(O)NR'R', wherein each R' is independently H or $C_{1-6}$ alkyl, —C(O)R', wherein R' is H or $C_{1-6}$ alkyl, is optionally substituted with 1-3 $R^6$;

$R^3$ is $C_{2-6}$ hydroxyalkyl;

$R^4$ is $C_{1-6}$ alkyl, $C_{2-6}$ alkenyl or $C_{2-6}$ alkynyl, each of which is optionally substituted with 1-4 $R^8$;

$R^5$, $R^6$, $R^7$, and $R^8$ are each independently hydrogen, $C_{1-6}$ alkyl, halo, $C_{1-6}$ haloalkyl, $C_{1-6}$ haloalkoxy, hydroxyl, $C_{1-6}$ alkoxy, amino, $C_{1-6}$ alkylamino, $C_{2-12}$ dialkylamino, cyano, nitro, —C(O)NR'R', wherein each R' is independently H or $C_{1-6}$ alkyl, —S(O)$_x$R' (wherein x is 0, 1 or 2), —C(O)OR', —C(O)R', $C_{3-7}$ cycloalkyl, $C_{6-10}$ aryl, heterocycloalkyl, or heteroaryl, wherein each R' is independently H or $C_{1-6}$ alkyl, wherein each of $C_{1-6}$ alkyl, $C_{1-6}$ haloalkyl, $C_{1-6}$ haloalkoxy, hydroxyl, $C_{1-6}$ alkoxy, amino, $C_{1-6}$ alkylamino, $C_{2-12}$ dialkylamino, —C(O)NR'R', wherein each R' is independently H or $C_{1-6}$ alkyl, —C(O)O—$C_{1-6}$ alkyl, $C_{3-7}$ cycloalkyl, $C_{6-10}$ aryl, heterocycloalkyl, or heteroaryl is optionally substituted with 1-3 $R^9$; and each $R^9$ is independently $C_{1-6}$ alkyl, $C_{1-6}$ haloalkyl, $C_{1-6}$ haloalkoxy, heterocycloalkyl, $C_{6-10}$ aryl, heteroaryl, $C_{4-10}$ cycloalkylalkyl, heterocycloalkyl-$C_{1-6}$ alkyl, $C_{7-16}$ arylalkyl, heteroaryl-$C_{1-6}$ alkyl, halo, hydroxyl, $C_{1-6}$ alkoxy, $C_{6-10}$ aryloxy, $C_{7-16}$ arylalkoxy, $C_{2-8}$ alkoxyalkoxy, amino, $C_{1-6}$ akylamino, $C_{2-12}$ dialkylamino, $C_{1-6}$ alkyl-amino-$C_{1-6}$ alkyl, $C_{1-6}$ alkyl-amino-$C_{2-12}$ dialkyl, —S(O)$_x$R' (wherein x is 0, 1 or 2), —S(O)$_2$NR'R', wherein each R' is independently H or $C_{1-6}$ alkyl, —C(O)NR'R', wherein each R' is independently H or $C_{1-6}$ alkyl, —NR'C(O)NR'R', wherein each R' is independently H or $C_{1-6}$ alkyl, —S(O)$_2$NR'C(O)NR'R', wherein each R' is independently H or $C_{1-6}$ alkyl, —C(O)R', wherein R' is H or $C_{1-6}$ alkyl, —C(O)—$C_{1-6}$ alkyl, —C(O)—$C_{6-10}$ aryl, —NHC(O)—$C_{1-4}$ alkyl, —NHC(O)—$C_{6-10}$ aryl, —C(O)NR'R', —C(O)NH—$C_{6-10}$ aryl, —C(O)OR', —OC(O)R', nitro, or cyano;

wherein a "heterocycloalkyl" group is a non-aromatic saturated or partially saturated monocyclic heterocyclic ring system(s) containing from 3 to 12 ring atoms, with from 1 to 5 heteroatoms selected from nitrogen, oxygen or sulfur in the ring;

wherein a "heteroaryl" group is monocyclic and bicyclic groups containing from five to twelve ring members, wherein each ring may contain up to four heteroatoms selected from nitrogen, sulfur and oxygen.

11. The method of claim 10, wherein the compound is:

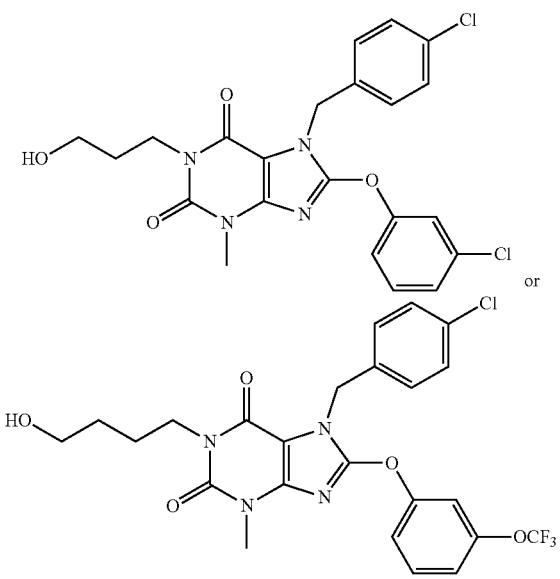

or pharmaceutically acceptable salt thereof.

12. The method of claim 10, wherein the compound is:

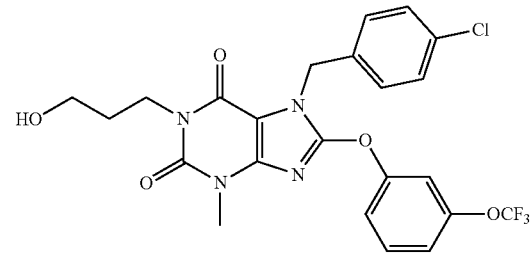 [SMILES: Cn1c(=O)n(CCCO)c(=O)c2c1nc(Oc1cccc(OC(F)(F)F)c1)n2Cc1ccc(Cl)cc1]

or a pharmaceutically acceptable salt thereof.

* * * * *